(12) United States Patent
Beckman et al.

(10) Patent No.: US 9,279,778 B2
(45) Date of Patent: Mar. 8, 2016

(54) APPARATUS AND METHOD FOR DETERMINING MOLECULAR STRUCTURE

(71) Applicant: Oregon State University, Corvallis, OR (US)

(72) Inventors: Joseph Beckman, Corvallis, OR (US); Wei Kong, Corvallis, OR (US); Valery G. Voinov, Corvallis, OR (US); William M. Freund, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 14/610,980

(22) Filed: Jan. 30, 2015

(65) Prior Publication Data

US 2015/0168318 A1    Jun. 18, 2015

Related U.S. Application Data

(63) Continuation-in-part of application No. PCT/US2013/052772, filed on Jul. 30, 2013.

(60) Provisional application No. 61/677,357, filed on Jul. 30, 2012.

(51) Int. Cl.
    *G01N 1/42*      (2006.01)
    *H01J 49/04*     (2006.01)
    (Continued)

(52) U.S. Cl.
    CPC ...... *G01N 23/2055* (2013.01); *G01N 23/20058* (2013.01); *H01J 49/0431* (2013.01)

(58) Field of Classification Search
    CPC .. G01N 15/0211; G01N 1/42; G01N 23/2055

USPC ........ 250/307, 251, 281, 290; 378/71; 850/63
See application file for complete search history.

(56) References Cited

U.S. PATENT DOCUMENTS 4,361,902 A * 11/1982 Brandt et al. ................. 378/152
5,019,775 A *  5/1991 Moulder et al. .............. 324/202
(Continued)

OTHER PUBLICATIONS

Bierau, "Trapping biomolecular ions in superfluid helium droplets," http://www.diss.fu-berlin.de/diss/servlets/MCRFileNodeServlet/FUDISS_derivative_000000010272/Dissertation_Frauke-Bierau.pdf?hosts=>pp. iii, 2, 3, 25, 64, 121, Nov. 15, 2011 (retrieved Dec. 5, 2013).

(Continued)

*Primary Examiner* — David A Vanore
(74) *Attorney, Agent, or Firm* — Klarquist Sparkman, LLP

(57) ABSTRACT

Certain disclosed embodiments concern a method and an apparatus for determining molecular structure. One embodiment comprises producing sample ions from a sample, cooling molecules of the sample ions by either embedding sample ions in superfluid droplets, such as superfluidic helium droplets, or subjecting sample ions in a cooled ion trap, to a selected temperature approaching absolute zero. Plural cooled sample ions confined in a diffraction zone are oriented using a laser, and a diffraction image is produced from oriented sample ions using an electron beam. Molecular structure is determined using collected images from different orientations obtained under different polarization directions of the orientation laser. Embodiments of an apparatus for determining molecular structure also are disclosed. The apparatus operation, data accumulation and processing are controlled by software. The software can directly calculate electron density maps without using heavy atom derivatives or multi-wavelength anomalous dispersion phasing methods.

30 Claims, 34 Drawing Sheets

(51) Int. Cl.
*G01N 23/205* (2006.01)
*G01N 23/20* (2006.01)

(56) References Cited

U.S. PATENT DOCUMENTS

| | | | |
|---|---|---|---|
| 5,087,815 A * | 2/1992 | Schultz et al. | 850/63 |
| 5,714,762 A * | 2/1998 | Li et al. | 250/559.2 |
| 6,040,653 A | 3/2000 | O'Neil | |
| 6,115,452 A * | 9/2000 | Marrs | 378/119 |
| 7,652,269 B2 * | 1/2010 | Bunton et al. | 250/491.1 |
| 7,683,318 B2 * | 3/2010 | Bunton et al. | 250/309 |
| 2003/0168593 A1 | 9/2003 | Hart | |
| 2005/0189485 A1 * | 9/2005 | McLean et al. | 250/287 |
| 2006/0262317 A1 * | 11/2006 | Doak et al. | 356/451 |
| 2007/0040113 A1 * | 2/2007 | Monroe et al. | 250/290 |
| 2008/0296483 A1 * | 12/2008 | McClelland et al. | 250/251 |
| 2011/0174973 A1 * | 7/2011 | DeWalch | 250/310 |
| 2011/0180696 A1 | 7/2011 | Gessner et al. | |

OTHER PUBLICATIONS

Spence et al., "Single Molecule Diffraction," *Physical Letters*, http://prl.aps.org/abstract/PRL/v92/i19/e198102>pp. 1-4, May 12, 2004 (retrieved Dec. 5, 2013).

International Search Report dated Jan. 13, 2014 from International Application No. PCT/US2013/052772.

Written Opinion dated Jan. 13, 2014 from International Application No. PCT/US2013/052772.

* cited by examiner

GFP

Top view of a distorted cylinder

Orientation laser

APPARATUS AND METHOD FOR DETERMINING MOLECULAR STRUCTURE

CROSS-REFERENCE TO RELATED APPLICATION

This is a continuation-in-part application of International Application No. PCT/US2013/052772, filed on Jul. 30, 2013, which was published in English under PCT Article 21(2), which in turn claims the benefit of U.S. provisional application No. 61/677,357, filed on Jul. 30, 2012. The provisional application is incorporated herein in its entirety.

ACKNOWLEDGMENT OF GOVERNMENT SUPPORT

This invention was made with government support the National Institutes of Health, under grant No. RC1 GM092054. The federal government has certain rights in the invention.

FIELD

The present disclosure concerns an apparatus and a method for determining the structure of molecules, fragments of molecules, clusters of molecules, nanostructures, or macromolecules such as biological macromolecules. Certain disclosed embodiments allow structure determination of macromolecules without first crystallizing the molecule.

BACKGROUND

The human genome has been known for a decade, but the information provided by the genome has had only a relatively modest impact upon understanding mechanisms of disease or how mutations affect function. While the DNA sequence from a genome provides information about the linear order of the amino acid constituents of proteins, limited tools are available to understand how proteins twist and fold into their functional forms. The folded shapes of proteins determine how they function in healthy tissue, how they misfold to cause disease, and how drugs bind to proteins to modulate function.

Billions of dollars have been invested to develop instrumentation to support structural determination of biological molecules. The successes are remarkable and the results are made available online through the Protein Data Bank. Currently, the gold standard of structure determination is x-ray crystallography. However, the method requires considerable technical prowess, needs high concentrations of pure protein, and frankly depends upon a fair amount of luck. Ultimately the success of crystallography is determined by the availability of a micrometer sized defect free single crystal. This barrier has posed a tremendous limitation on the progress of biological research. For example, more than half of all proteins and 95% of integral membrane proteins do not crystallize. Thus, their structures cannot be determined by crystallography. Other alternative methods including NMR, cryoelectron microscopy, and neutron diffraction, have had limited successes. Altogether, these methods have only contributed to ~10% of all the structures deposited in the protein data bank.

SUMMARY

Certain disclosed embodiments concern a method and an apparatus for determining molecular structures that do not require crystallizing a sample. One embodiment of the method may comprise, for example, producing sample particles, typically ions, from a sample (e.g., a solid or liquid solution), cooling the sample particles to a temperature of less than about 50 K, such as less than about 20 K, confining single or plural cooled sample particles in a diffraction zone, and orienting single or plural cooled sample particles using a laser. A diffraction image is produced from oriented sample particles using an electron beam. Molecular structure is determined using collected images.

The sample typically comprises macromolecules. Examples, without limitation, of macromolecules include biological molecules, such as proteins, nucleic acids, carbohydrates and lipids. Fragments, clusters, and nanostructures of organic and/or inorganic compounds are also possible. In certain disclosed embodiments, sample ions are produced using electrospray ionization, and the ions may be selected and hence purified by a mass analyzer. Cooling can be achieved by embedding the sample particles in superfluid droplets, such as superfluidic helium droplets, or by using a cooled ion trap. Doped droplets can be size reduced via collisions, such as with helium gases, for diffraction purposes, or the chilled ions can be removed from the droplet through resonant laser excitation via non-thermal ejection.

The laser for sample particle orientation is selected to generate wavelengths that do not significantly heat or perturb the structure of the sample ions. In certain working embodiments, the laser was an Nd-YAG laser that generates wavelength of 1064 nm to orient the molecules. The laser is capable of producing 50 μs pulses at 20 Hz with a peak power of 200 kW. The laser is focused into an area of 0.1 $mm^2$ with an electric field of up to 200,000 V/cm. For certain embodiments, the laser can orient individual sample particles or plural sample particles, such as from about 2 to about $10^5$ sample particles, or from about $10^2$ to about $10^4$ sample particles, within about 1° for a period of about 50 μs, or from 5 μs to 50 μs. Diffraction data is accumulated from multiple packets of sample ions that are oriented substantially identically. Radiation damage to sample ions is minimized by replacing sample ions, such as after every laser pulse, and cooling the sample molecules, such as to near absolute zero temperature.

Elliptical polarization of the laser is changed by a selected amount to rotate the sample particles to obtain diffraction from multiple orientations. In certain embodiments, a rotating polarization prism is used in combination with the alignment laser to rotate sample particles around a primary axis of polarizability. In certain embodiments, sample particles are rotated from 1° to any position up to 180°, and at any desired position in between, such as 1° increments. Sample particles can be modified to increase anisotropy if the inherent anisotropy is insufficient to allow laser orientation.

The apparatus can be operated in pulsed mode, continuous mode, or mixed mode of operation. In the pulsed mode operation, the laser beam, the electron beam, and the sample beam can be all in pulsed mode. For each orientation of the sample defined by the polarization of the laser, sample is extracted and purified, cooled to the appropriate temperature, oriented by the laser, bombarded by the diffraction source, and the resulting image recorded. The method steps can be repeated as desired such as 20 times per second. Repeating the method steps allows collecting sufficient diffraction data to produce a suitable diffraction image. Laser polarization can be changed to another selected angle, and recording from a new orientation can be performed. In the mixed mode of operation, the electron beam can be continuous but the recording camera needs to be synchronized with the pulsed laser beam so that only diffraction from the oriented sample can be recorded. The sample beam can be either continuous or pulsed, although pulsed mode saves the rate of sample consumption. The recording camera can also be synchronized with the pulsed laser during its off time so a background diffraction pattern of randomly oriented sample can be recorded. Thus, in certain embodiments, the method comprises orienting sample particle packets comprising from about $10^2$ to about $10^4$ macromolecules for a selected period of time, and continuously collecting electron diffraction images from these packets.

The coherent length of the diffraction source should be shorter than the average distance between two adjacent particles but longer than the desired largest interatomic distance of the sample. The resulting diffraction image is a simple sum of continuous images of scattering from each molecule in the diffraction zone.

Oversampling of the image and iterative algorithms may be used to extract both phase and intensity information. The software can directly calculate electron density maps without using heavy atom derivatives or multi-wavelength anomalous dispersion phasing methods.

Embodiments of an apparatus for determining molecular structure are also disclosed. One embodiment comprises a pulsed source of superfluidic helium droplets, a source of sample ions, an orientation laser for orienting ions doped in helium droplets, and an electron source for electron diffraction imaging of oriented sample ions in the diffraction zone.

Disclosed embodiments may comprise a cold head and associated cryogenic helium nozzle to generate helium droplets. Regulating the temperature of the helium nozzle using a standard temperature controller with a heater allows the temperature of a helium nozzle to be adjusted, which further determines the average size of the helium droplet. For certain embodiments, a pulsed helium droplet valve is used that has an opening time of about 10-20 microseconds, is capable of withstanding pressures up to about 100 atmospheres, and is capable of operating at frequencies of several thousand Hertz. At least one skimmer, and potentially plural skimmers, may be used to select a desired portion of a helium droplet beam. A diffusion pump may be coupled to the droplet source to withdraw helium droplets not selected by the skimmer.

The apparatus may, and typically does, include several mass analyzers, such as a quadrupole mass analyzer. In certain embodiments, an electrospray ionization source is used to produce ions of a selected sample for mass selection by the mass analyzer.

In one embodiment, sample ions from the source are directed to a mixing chamber that mixes sample ions with superfluidic helium droplets produced by the helium droplet generator. An ion bender may be positioned to turn sample ions that are emitted from the electrospray source for mixing with the superfluidic helium droplets in the mixing chamber. In some embodiments, a chilled ion trap is in place of the mixing chamber, and cooling is achieved via collisions of the trapped ions with the gases in the chilled ion trap. In another embodiment, sample ions directly outside the ion source are slowed down by an electrode to directly intercept with the droplet beam, and the resulting ion doped droplets are accelerated through a size reducing region formed by electrodes and low pressure helium gas.

Certain disclosed embodiments include an orientation and diffraction chamber. A series of focusing and acceleration/deceleration electrodes may be positioned upstream of the diffraction chamber. The electrodes have different applied voltages that may be pulsed in an appropriate sequence. The pulsed electron beam, pulsed laser beam, and pulsed ion beam are combined in the diffraction zone.

An orientation laser generates polarized infrared light and directs such light to interact with sample ions, particularly ions embedded in helium droplets, as such ions enter the orientation and diffraction chamber. For certain embodiments, the laser is an Nd-YAG Agilite 569 from Continuum Lasers, which can produce 50 µs pulses at 20 Hz with a peak power of 200 kW. The laser beam is focused into an area of 0.1 mm$^2$, which generates an electric field of 200,000 V/cm. The laser may further comprise a polarizer and several phase retarders. In some embodiments, the laser has two phase retarders. The laser beam controllably rotates to obtain diffraction data from different angles relative to the oriented sample ions.

A pulsed electron gun provides an electron beam. The electron beam is directed to impinge the oriented biological molecule ions in the diffraction chamber to produce an electron diffraction image. In certain embodiments, the electron gun is a Kimball Physics electron gun.

A recorder is associated with the diffraction chamber to record diffraction data. In certain embodiments, the recorder is a cooled staged camera to reduce noise. The camera may include plural cooling stages and/or a cooling chamber surrounding the camera, such as might contain dry ice, to further minimize camera noise.

Certain disclosed embodiments further comprise an analytical section downstream of the diffraction chamber. This section may include, for example, an ion bender and a mass detector to detect sample ions exiting from the orientation and diffraction chamber. The analytical zone also may include a helium droplet detector. The analytical section ensures that desired helium droplets and sample ions are proceeding through the apparatus.

The apparatus may further comprise an analytical wheel comprising plural receptacles. The receptacles are useful for housing at least one device selected from (i) a Faraday cup to determine the number of electrons included in an electron beam, (ii) a phosphor screen to align and detect electrons to time an electron beam and its intersection with the laser beam and the doped helium droplets, (iii) a TEM sample standard, and (iv) a beam size and position measurement device, (v) a laser ionization time-of-flight mass spectrometer for timing determination of the sample molecule.

The foregoing and other objects, features, and advantages of the invention will become more apparent from the following detailed description, which proceeds with reference to the accompanying figures.

DETAILED DESCRIPTION

I. Introduction

Figure 1:
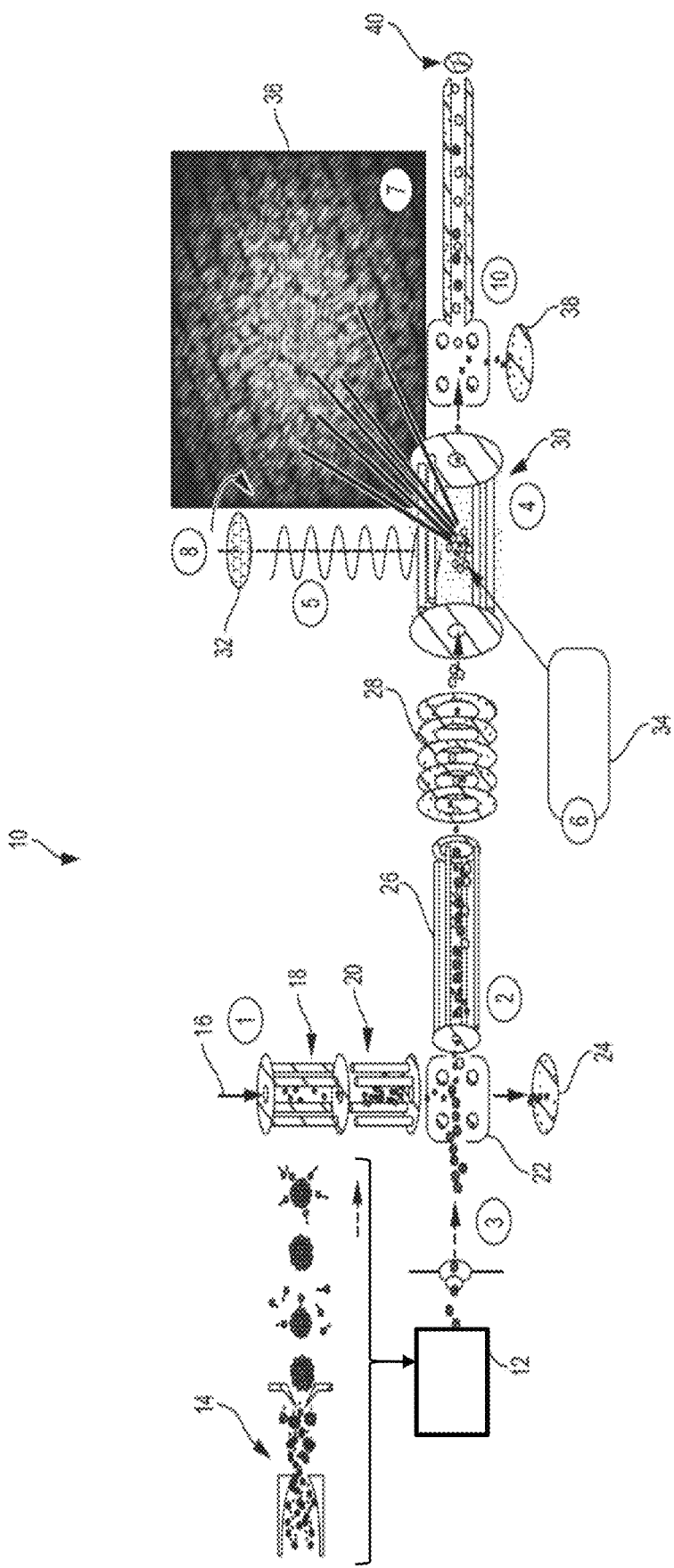
FIG. 1 is a schematic drawing illustrating certain components of a disclosed embodiment of an apparatus for determining molecular structure, along with a sequence for one disclosed embodiment of a method for producing a diffraction image of a protein.

More than half of all proteins, including 95% of integral membrane proteins, do not crystallize and thus their structures cannot be determined by crystallography. Disclosed embodiments of the present apparatus and method address this problem by combining technologies derived from mass spectrometry, laser induced alignment and orientation, electron diffraction and cryogenic helium systems to allow atomic resolution of structures of individual macromolecules to be directly determined without crystallization.

II. Definitions

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Although methods and apparatus components similar or equivalent to those described herein can be used, suitable methods and components are described below.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Carbohydrate: Organic compounds made of carbon, hydrogen, and oxygen atoms, comprising monosaccharides (single sugars) linked together to form polymeric structures. An example is starch, which comprises many linked glucose molecules.

Infrared: Infrared is a specific region of the electromagnetic spectrum that is just beyond the light region that spans from 1,000 nanometers to $10^6$ nanometers (1 micron to 1,000 microns), with near infrared ranging from about 500 nanometers to about 2,000 nanometers (0.5 to about 2 micrometers).

Lipids: Molecules, typically nonpolar molecules including, by way of example, fats, phospholipids, and steroids, and waxes.

Macromolecule: A macromolecule is a molecule with a relatively large number of atoms, such as greater than about 50 component atoms, and having a molecular weight of up to at least one million daltons (1 megaDalton). Examples of biological macromolecules include, without limitation, nucleic acids, such as DNA and RNA, proteins, carbohydrates, and lipids. Disclosed embodiments of the present apparatus and method are useful for analyzing any molecule, particularly macromolecules, that are asymmetric.

Nucleic Acid: An overall term that includes DNA and RNA biopolymers, and is synonymous with polynucleotide. Nucleic acids can vary in size, but are generally very large molecules, and typically range from about 20 nucleotides to large chromosomes that contain millions of base pairs.

Polypeptide: A polymer in which the monomers are amino acid residues that are joined together through amide bonds. When the amino acids are α-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

Protein: A molecule, particularly a polypeptide, comprised of amino acids.

Residue or amino acid residue: An amino acid that is incorporated into a protein, polypeptide, or peptide.

Nanostructure: A microscopic object having a largest physical dimension smaller than one micrometer.

III. General Discussion of Method for Determining Structure of Sample Molecules Certain embodiments of the disclosed apparatus produce intense electrical fields generated by elliptically polarized infrared laser light. These electrical fields are used to precisely orient thousands of sample ions simultaneously without otherwise heating or exciting the sample ions. For example, laser technology allows orienting macromolecules for as long as 50 microseconds. Sample ion orientation is timed with an impinging electron beam for a time period sufficient to collect continuous diffraction images. The sample ions can comprise, for example, ions of macromolecules, nano-crystals of macromolecules, fragments of macromolecules, clusters of macromolecules, complexes of macromolecules, nanostructures of organic compounds, nanostructures of inorganic compounds, or combinations thereof.

The ions typically are cooled to near absolute zero, such as within 50 K of absolute zero, within 10 K of absolute zero, or within 1 K of absolute zero. This can be achieved using, for example, superfluidic helium droplets to chill the ions to about 0.37 K. Helium droplets provide an exceptionally gentle matrix that is very different from that provided by a solvent. Superfluid helium does not interact with the embedded macromolecules; rather it cools the embedded molecules, typically in microseconds or less, removing heat from individual macromolecule ions. This helps protect ions from both denaturation and radiation damage. Alternatively, the macromolecule ions can be cooled by a cryogenic trap via collisions with helium atoms in the trap. The resulting temperature of the macromolecule ions typically will be lower than 50 K, such as lower than 20 K.

Certain disclosed embodiments gently ionize, entrap and orient packets of plural macromolecules for diffraction, and the cycle can repeat at fast intervals, such as 20 times per second. Continuous electron diffraction images are collected from these packets. Initial calculations indicate that an image of approximately $10^8$ diffracted electrons can be accumulated each minute from a small protein. By changing the elliptical polarization of the laser, packets of individual macromolecules can be rotated to obtain diffraction from multiple projections. Collection of continuous diffraction images from these multiple projections provides sufficient information to overcome phase problems that confound crystallography. Thus, electron density maps can be directly calculated without the need for heavy atom derivatives or MAD (multiwavelength anomalous dispersion) phasing methods.

The sequence to produce a diffraction image for one orientation of a sample, such as a protein, is shown in FIG. 1. Certain disclosed embodiments involve three steps: (A) chilling packets of sample to near absolute zero, such as by using superfluidic helium droplets or a cooled ion trap; (B) orienting packets of individual macromolecules in three dimensions with an elliptically polarized laser; and (C) continuous or pulsed collection of diffraction patterns from multiple projections of the macromolecules from a pulsed or continuous beam of electrons or of x-rays. The image labeled 7 in FIG. 1 is the calculated continuous diffraction pattern from a 0.05 Å electron wavelength of one orientation for the 16 kDa protein Cu,Zn SOD1. Additional components (D) are used to align and optimize the operation of the instrument.

A. Electrospray Ionization and Freezing Packets of Molecules

1. Preparing Macromolecular Ion Packets

In certain disclosed embodiments, electrospray ionization is used to introduce molecular ions into a vacuum system. Ions produced by this method are substantially free from solvents, including water. By carefully choosing the physical conditions of the ionization source, some proteins and macromolecules can retain their structure in vacuo, even when desolvated or dehydrated. The field of native protein mass spectroscopy has made remarkable progress in generating native or near native protein ions from electrospray ionization and also in understanding the conditions that induce unfolding. Mass spectrometry is now routinely used to measure ligand affinities for proteins. Multimeric proteins including entire viruses, the 800 kDa GroEL prokaryotic chaperone and the 20S proteasome have been probed by mass spectrometry and ion mobility. Membrane proteins have recently been shown to ionize as intact complexes with careful choice of nonionic detergents. Newer approaches are being developed that may be even gentler, such as laser desorption of aqueous macromolecules into electrospray plumes or matrix assisted laser desorption ionization. Disclosed embodiments of the present apparatus can utilize all of these advances to stabilize structures during ionization.

In certain embodiments, ions are purified by a mass selector based on their mass-to-charge ratios and by other physical properties such as permanent dipole, geometric size or volume, or polarizability. A packet of macromolecular ions is accumulated in an ion trap. A detector is used to quantify macromolecular ion packets from the ion trap. A challenge for both NMR and crystallography is the need to prepare high concentrations of pure samples. In contrast, disclosed embodiments of the present instrument work best with dilute ions, and the biological molecule ions do not need to be highly purified. Because a mass selector is incorporated downstream from the ion source, impurities can be removed from the sample as part of the process. Other types of mass analyzers, ion mobility devices or deflective type devices can be used to provide further mass and conformation resolutions as needed.

Macromolecular ions may be rapidly cooled, such as within a few microseconds, using a superfluidic fluid, such as superfluidic helium droplets, or in a cryogenic ion trap. Helium atoms evaporating from these droplets carry away heat from internal motions of the macromolecular complex, allowing it to settle into its most stable conformations. Cooling can also take place prior to and/or during ionization.

Figure 2:
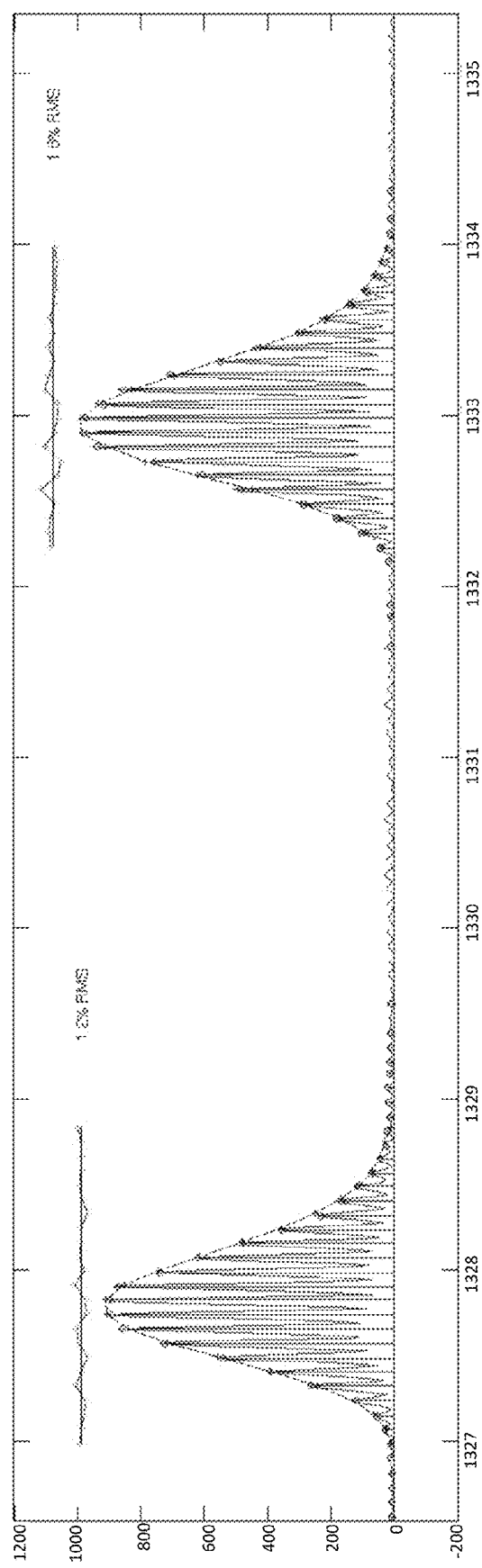
FIG. 2 is an isotope-resolved mass-to-charge spectrum of human Cu,Zn superoxide dismutase (SOD1) where the dotted envelop line with plus signs shows the predicted isotopic distribution calculated using only the empirical formula of SOD and deviations between the observed and theoretic spectra are plotted above with the root mean square, illustrating the ability to purify proteins "on-the-fly" directly from tissues and entirely free of residual waters or salts.

FIG. 2 illustrates how an abundant protein can be "purified" directly from tissues in a mass spectrometer free of residual sodium or water adducts, and still retain its two metal ligands copper and zinc. The electrospray mass spectrum represents the $12^{th}$ charge state of a mutant human superoxide dismutase (SOD1) overexpressed in transgenic mice that causes the mice to develop ALS. The isotope-resolved spectrum was collected with a ThermoFisher FTICR within 2 minutes of a 100-μg tissue punch taken from the mouse spinal cord. Since both copper and zinc are positively charged and positioned close to each other, denaturation would cause the loss of these metals. These spectra were collected by averaging packets of about $10^5$ SOD molecules with each injection taking about 50 milliseconds. These data establish that disclosed embodiments of the present apparatus and method can be used to generate protein packets of high purity, and protein packets can even be isolated directly from tissues. The disclosed method can work with low concentrations of proteins found in vivo.

The data in FIG. 2 intentionally shows two forms of SOD differing only by the absence of zinc in the left peak as isolated from brain. FIG. 2 illustrates that even a low-resolution quadrupole mass selector can easily separate proteins differing by a single heavy atom for image collection. A significant variable in crystallography is estimating the unknown and variable extent of occupancy for ligand binding. The mass selector can choose only those proteins with ligand for further examination to make occupancy a controlled parameter. This provides a new tool for structure-based drug screening because structures may be determined from only those macromolecules selected to retain ligands.

2. Delivering Ion Packets

Figure 21:
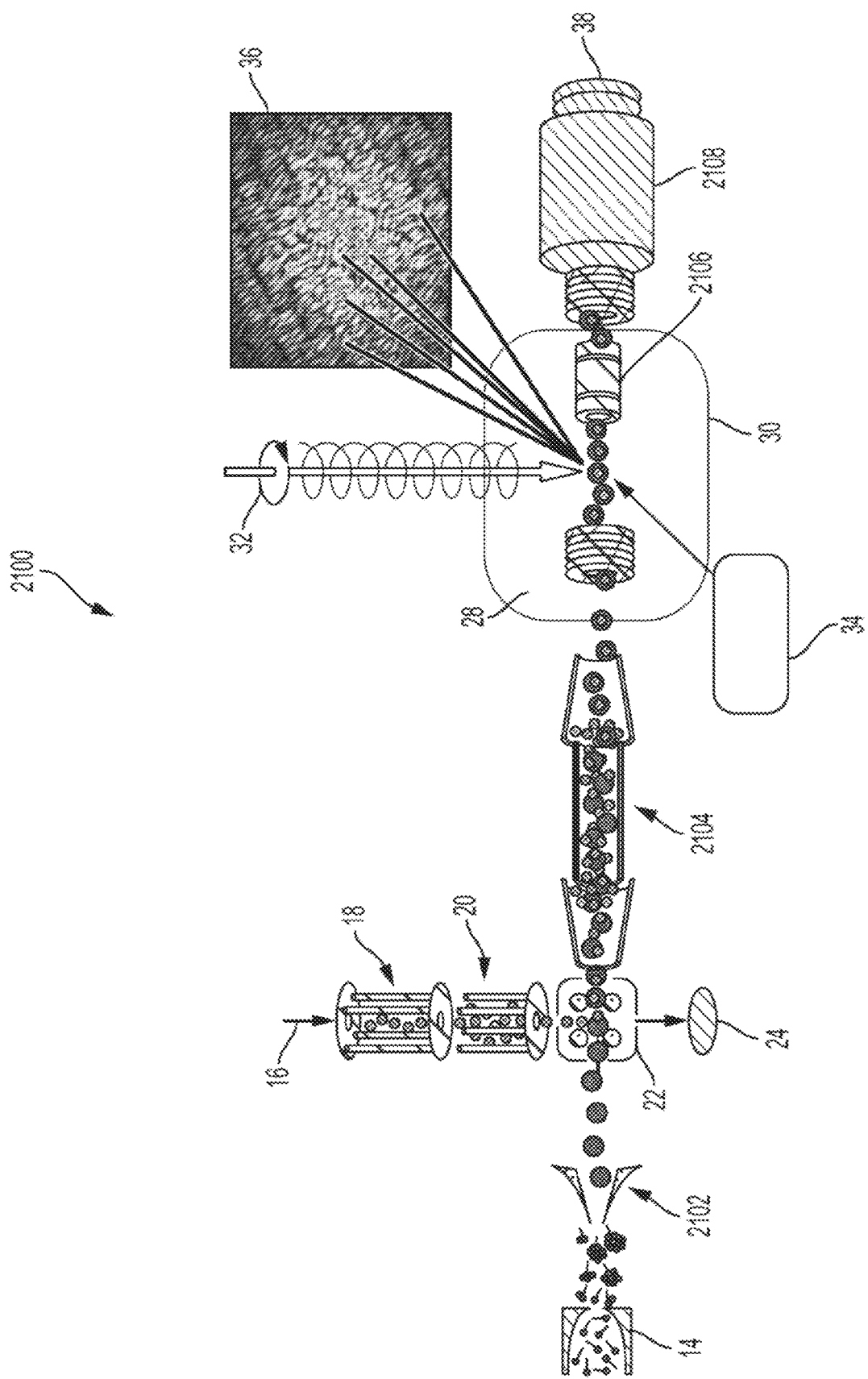
FIG. 21 is a schematic drawing illustrating certain components of a disclosed embodiment of an apparatus for determining molecular structure.

A packet of molecular ions is pulsed through for mixing with the droplet beam. The molecular ions are directed through a long axis of the instrument and focused with an ion trap (labeled as component 2) in FIG. 1. This guide can be a multipole ion trap, as shown in FIG. 1, or an electrostatic ion trap, as illustrated in FIG. 21. Suitable ion traps include, but are not limited to, electrostatic, quadrupole, hexapole, octapole, and Paul-type ion traps. Alternatively, the ions can be slowed down by an electrode facing the ion source and be picked up in the path of the droplet beam, as in FIG. 25. Downstream, collisions with low pressure helium gases reduce the size of the doped droplets to the desired number of helium atoms per droplet.

3. Superfluidic Helium Droplets

As the packet of ions is accelerated into the long axis, a pulsed stream of fluid, typically a superfluidic fluid, such as superfluid helium droplets (containing from about $10^4$ to about $10^{12}$ helium atoms each) is released to mix with the packet of macromolecules in the ion trap. A certain portion of the ions are captured by the droplets, and these captured ions are cooled by fluid evaporation. This process has the ability to cool captured ions to a temperature approaching 0.37 K. This cooling effect facilitates precise laser-induced alignment of the ions and minimizes radiation damage during diffraction. Fluid droplets are provided in substantial excess relative to the biological molecules to maximize the number of biological molecule ions that will be embedded in a fluid droplet. Charge repulsion prevents two macromolecular ions from embedding in one droplet.

In another embodiment, the ion trap can be cryogenically cooled (cryogenic ion trap), and the helium gas in the trap facilitates cooling of the ions. The macromolecular ions reach thermal equilibrium with the ion trap, which is typically less than 50 K, and desirably is less than 20 K.

B. Laser-Induced Orientation

1. Trapping and Focusing Packets of Chilled Macromolecular Ions

After electrostatic focusing, macromolecular ions embedded in a fluid, typically superfluidic helium, or bare ions from the cryogenic ion trap, are guided into the orientation/diffraction chamber. Optionally, a specially designed Digital Ion Trap can be used to confine the ions in the diffraction region. The macromolecular ions embedded in a fluid are constrained in a region in the crossing path of an orientation laser beam and an electron beam. A digital trap uses square electrical pulses rather than sine waves and is far more effective at guiding and focusing high mass ions. The same electrical field can be used to align the permanent dipole moment of the biological molecule ions to establish an initial "head-to-tail"

orientation. This initial orientation can be slight. In embodiments where the digital ion trap is not included, the electrodes upstream of the orientation/diffraction chamber can be used to establish the same initial "head-to-tail" orientation.

This preliminary orientation by either method simplifies the subsequent complete orientation by the elliptically polarized laser light.

2. Elliptically Polarized Laser Alignment of Macromolecules in the Packet.

The sample beam is intercepted by an elliptically polarized laser pulse. The laser field orients thousands of sample particles for a period of time for further diffraction. The intense electric field of the laser induces alignment to within one degree for all three Euler angles in a few nanoseconds. See FIGS. 3 and 6. The laser frequency is specifically chosen where biological molecules typically have negligible absorbance. As a result, the laser does not appreciably heat or perturb the macromolecular structure.

Figure 3:
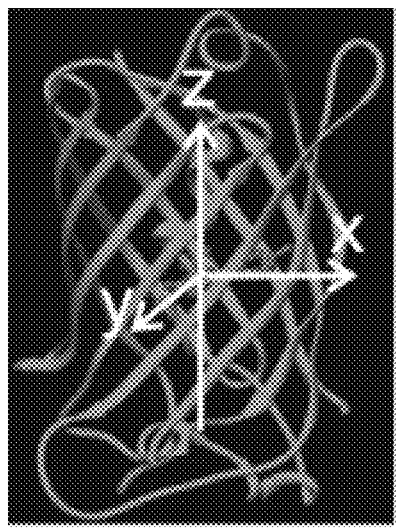
FIG. 3 illustrates the concept of field-induced alignment. Using linear polarized light in the vertical direction, where an alignment field $E_O$ generates a torque as it interacts with the longest z-axis of the β barrel of GFP. Using elliptically polarized light with two alternating unequal fields $E_H$ and $E_V$, three dimensional alignment including both the long and short axes of GFP can be achieved.
Figure 3:
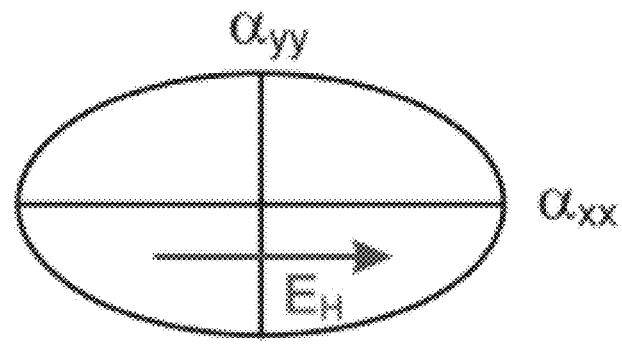
Figure 3:
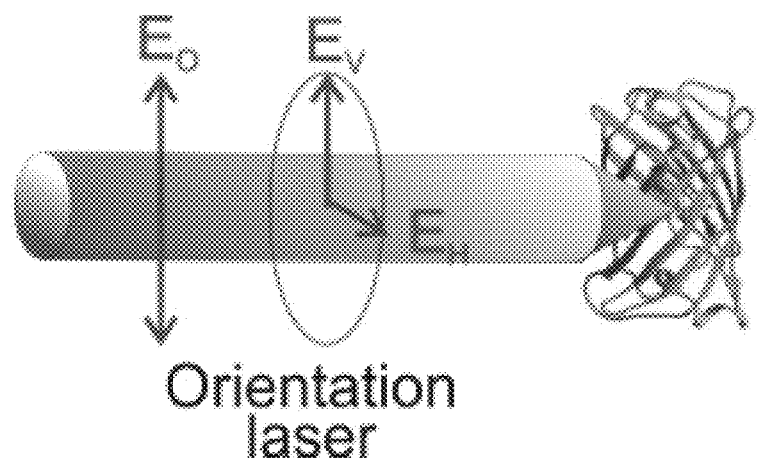

The field of laser-induced alignment is a quickly evolving field, from one-dimensional alignment of small gas phase molecules to three-dimensional alignment of polyatomic molecules, and now to complete orientation of gas phase species. The torque generated by laser light on a macromolecule is determined by its polarizability tensor, which results from shifts of electron density (an induced dipole) within a molecule in response to an electric field. Polarizability scales with the geometrical size of a molecule as illustrated by the elongated β barrel of green fluorescent protein (GFP) (FIG. 3). To provide sufficient torque to orient macromolecular complexes as large as 1 megaDalton, certain disclosed embodiments use a ND-YAG scientific laser (Nd-YAG Agilite 569 from Continuum Lasers). The electric field should be strong enough to orient biological molecules, but insufficient to cause other physical effects such as modifying the internal structure of the sample particles or affecting the incoming high energy electrons during diffraction.

In certain embodiments, particular steps allow an instrument to orient a macromolecule completely. With reference to proteins as examples of biological molecules, a first step is to orient the proteins "head-to-tail" in one direction using their permanent dipoles. Most proteins have significant permanent dipoles on the order of hundreds of Debyes. At a temperature of 0.37 K, a field of 100 V/cm provides initial alignment for the laser to generate a "heads up" orientation. A DC electrical field produced either by a Digital Ion Trap (component 4 in FIG. 1) or the field from the electrodes upstream from the diffraction chamber can orient ions via their permanent dipole just prior to the arrival of the laser pulse.

Figure 4:
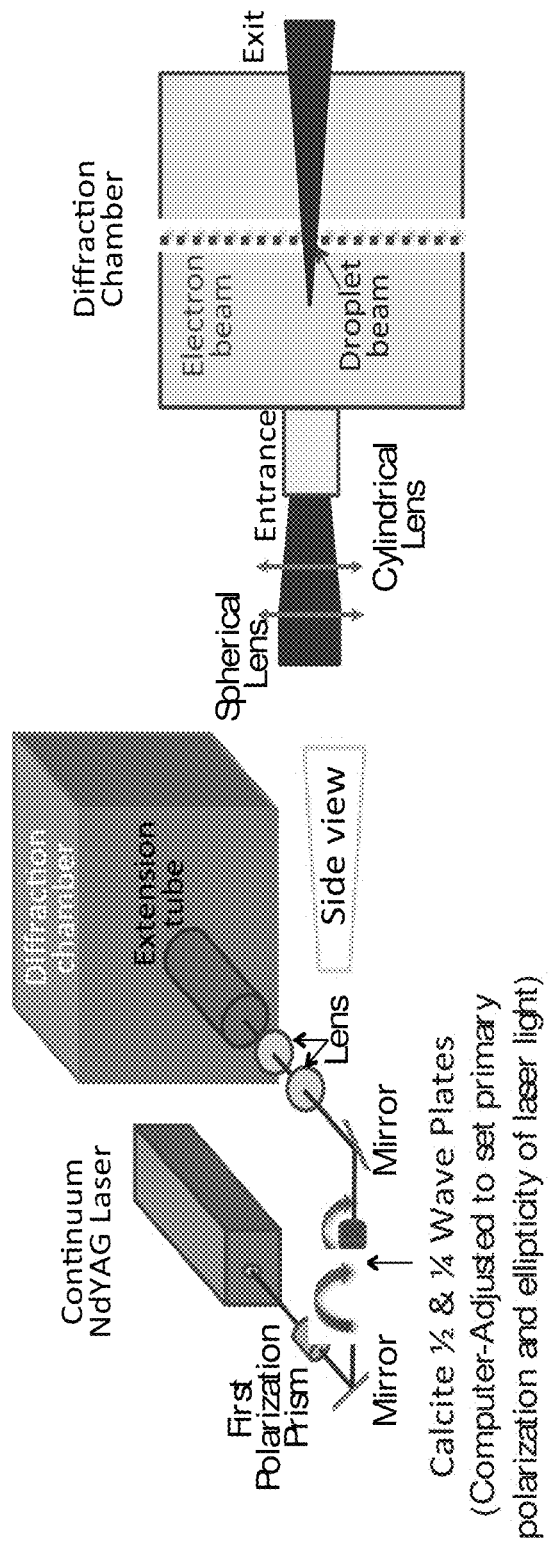
FIG. 4 illustrates that, by rotating the retardation waveplates, the macromolecule can be rotated 180° around its primary axis of polarizability. For certain embodiments, a laser beam will be focused into an area of 0.1 mm², which generates an electric field of 200,000 V/cm that can orient a protein in a few nanoseconds.

Macromolecules chilled to near absolute zero are effectively rigid bodies. Laser-induced alignment is based on the anisotropic shape of a sample ion that generates an induced dipole in an external electric field. FIG. 3 illustrates the concept of field-induced alignment. For simplicity, FIG. 3 first illustrates alignment using just linear polarized laser light in the vertical direction. The alignment field $E_O$ generates a torque as it interacts with the longest z-axis of the β barrel of GFP. By rotating the polarization prism (FIG. 4), the macromolecule is rotated 180° around its primary axis of polarizability.

The disclosed "molecular goniometer" results from using elliptically polarized laser light to produce two controllable orthogonal electrical fields that can orient a macromolecule in 3D. FIG. 3 illustrates how GFP, which like most protein ions is not truly cylindrically symmetric, has two unequal polarization axes that generate torque to rotate the protein in response to two orthogonal electric fields induced by elliptically polarized laser light. As a result, a protein's orientation can be controlled by changing the elliptical polarization of the laser light with two phase retarders developed to withstand the intense laser irradiation. In certain disclosed embodiments, this is achieved by using a calcite half-wave plate and a second calcite quarter-wave plate, both of which are moved under computer control, to produce a precisely controllable degree of elliptical polarization. This causes the laser light to have both a vertical $E_V$ and a horizontal $E_H$ component. The two components of the electric field $E_V$ and $E_H$ interact independently with the macromolecular ion at alternating times, because they do not have the same phase.

The degree of alignment is determined by the ratio of two energies:

1) the interaction (orientation) energy between the polarizability anisotropy with the laser field; and
2) the thermal energy of the macromolecule.

Thus one method to facilitate orientation is to cool the macromolecule. For a small protein such as GFP with a polarizability volume of about 50 nm³, within the laser field of $10^8$ W/cm² generated by the alignment laser, the resulting angular deviation is calculated to about 37° at room temperature, 19° at 77 K, and 1° at 0.37 K. Thus, most proteins are oriented by using their endogenous dipole moment to provide initial head-to-tail orientation and then by using their intrinsic polarizability to rotate the molecules to any desired orientation by the polarization of the laser light. If a macromolecule is too symmetric for effective orientation, certain modifications of the protein may be incorporated in the sample to provide a handle for laser field manipulation. Laser-induced orientation is particularly effective for larger multimeric complexes, which will generally have greater asymmetry.

FIG. 1 illustrates the processes of formation and doping of superfluid helium droplets. A technique for producing superfluid helium droplets was invented in the early-1990s by the Toennies group (*Phys. Scr.* 76 (2007) C15) through the supersonic expansion of precooled (1-20 K) helium gas at high pressure (10-40 atm). Helium droplets are a gentle matrix and are optically transparent. The helium droplets do not interact or perturb the sample ions, nor do they denature biomolecules. Helium droplets are superfluids and behave independently from the ions they enclose. They do not distort the structure; they only reduce the molecular vibrations as a consequence of cooling. The extreme cooling action plus frictionless environment have made superfluid helium droplets an ideal medium for field-induced orientation. This has been used to perform linear dichroism spectroscopy of small biological molecules in the gas phase, such as DNA bases and amino acids.

Superfluidic helium droplets are the ultimate cryostat and have a pickup efficiency upon collision with small molecules approaching 100%. When a droplet and a dopant molecule collide, some helium atoms from the droplet evaporate to remove the kinetic and internal energy of the dopant to reach 0.37 K. Evaporation of one helium atom carries away 0.06 kJ/mol of energy and thus the heat capacity of a droplet containing $10^7$ helium atoms is on the order of $6 \times 10^5$ kJ/mol. At room temperature, each atom in a molecule carries a thermal energy of about 4 kJ/mol; hence a single helium droplet in disclosed embodiments of the present system can remove the thermal energy from a molecule containing as many as $10^5$ atoms. Without being limited to a theory of operation, the corresponding upper size limit of the protein is therefore on the order of a megaDalton.

Helium droplets are vastly different than organic solvents. Organic solvents disrupt the hydrophobic internal packing of a protein favoring its denaturation, whereas the superfluidic properties of helium in droplets minimize interactions with the protein. Protein motions simply cause the evaporation of helium.

C. Electron Diffraction

Oriented sample ions are electrostatically focused in the diffraction area. The sample ions are then exposed to a coherent high-energy electron beam. Electron diffraction patterns are accumulated with an appropriate imaging system and recording device, for example, a set of multichannel (MCP) plates with a phosphor screen and a camera, such as a charge-coupled device (CCD) or intensified CCD (ICCD) camera, or a phosphor screen with an image intensified camera. Each pixel has the sensitivity to detect a single scattered electron. Only low angle (such as <3°) diffraction will be collected for the necessary resolution. For example, with 40 keV electrons, the wavelength is 0.05 Å and the data for 1 Å resolution will diffract at 1.9°. This energy is lower than that used in most electron microscopes, allowing the electrons to be scattered more efficiently while minimizing inelastic scattering that would complicate the analysis.

Electron diffraction becomes practical with oriented individual macromolecules. Electron diffraction of small molecules in the gas phase can measure bond distances to less than 0.01 Å, because the wavelength is only 0.05 Å for electrons accelerated to 40 keV. Furthermore, electrons are scattered approximately $10^4$ times more efficiently than x-rays. Disclosed embodiments of the present invention therefore use electron diffraction to derive high-resolution structures from far fewer molecules than are present in a crystal used for x-rays (a small macromolecular crystal for x-ray diffraction contains at least $10^8$-$10^{11}$ molecules). On the other hand, the diffraction source could also be a coherent x-ray source if the flux of the x-ray is sufficiently large and if sufficient sample particles are available.

In the past, two factors have limited the approaches of electron diffraction in macromolecular structure determination. Because electrons are so effectively scattered, they can only be used on extremely thin samples (roughly 100 nm) and the 3D crystals used for x-ray diffraction are too opaque. The high scattering efficiency also imparts severe radiation damage by electrons before complete images can be collected from suitably thin samples. Thus, electron diffraction has a reputation for yielding low-resolution macromolecular structures and is generally restricted to 2D crystalline arrays of protein or other special cases. But there are notable successes, such as the 2.5 Å resolution of tubulin assembled in microtubules.

Disclosed embodiments address these two factors that traditionally limit electron diffraction. First, the high scattering efficiency of electrons is ideal for working with individual macromolecules that are precisely and controllably oriented. Second, radiation damage on image quality is minimized because the macromolecules are replaced with every laser pulse and because macromolecules are cooled to near absolute zero. Cooling also reduces the temperature-dependent component Debye-Waller factors (also known as B factors or temperature factors) that diminish resolution.

D. Diffraction Data Accumulation and Processing

Crystal-free diffraction offers several advantages. The flow of the fluid droplet beam refreshes the sample particles every pulse, allowing repeated signal accumulation of diffraction for a chosen orientation of the sample particles. While space-charge repulsion ultimately limits the number of macromolecules to a few thousand constrained in the diffraction region in one pulse, this is overcome by accumulating data from multiple packets that are identically oriented. Moreover, the resulting continuous diffraction patterns allow for direct calculation of phases by well-established oversampling methods.

Within the diffraction region, the macromolecules undergo translational motions, but rotational motions are prevented by the laser-induced orientation. As long as the coherent length of the diffraction source is shorter than the spacing between adjacent sample particles, the diffraction image is the simple sum of the continuous images from each sample particle in the diffraction zone.

The theoretical foundation of single molecule structure determination is the phase retrieval algorithm via oversampling. Single molecules do not generate discrete Bragg diffraction lattice points but instead produce continuous Fraunhofer diffraction patterns. These continuous patterns can be sampled more completely to yield additional intensity information. If one samples at twice the Nyquist frequency, thereby doubling the number of equations to $2 \cdot 1 \cdot m \cdot n$, there are unique solutions to the phases of the scattering waves. Two additional constraints introduced by Miao and Sayre (*Acta Crystallogr., Sec. A: Found. Crystallogr.* A 56 (2000) 596) allow the phases to be extracted: 1) the sample ion is surrounded by a near vacuum with little electron density; and 2) the electron density within the macromolecule is real and positive. These two constraints allow the phases to be solved iteratively in a few hours on a desktop computer. The algorithm used for certain disclosed embodiments can also accounts for the liquid helium surrounding the macromolecule rather than a pure vacuum.

Such oversampling techniques are currently used in reconstructions of 3D structures of sub-micron crystals fixated on a thin substrate and even for images of proteins embedded in frozen cells. For non-biological samples, extreme dosages can sometimes be tolerated and results in a high quality diffraction pattern, for example sub-angstrom resolution have been reported for semiconducting and metallic nanocrystals as well as carbon nanotubes. These successes support the potential for electron diffraction in disclosed embodiments of the present apparatus to yield high-resolution structures.

E. Reorientation of Ion Packets to Collect New Diffraction Projections

The elliptical polarization of the alignment laser is controllably changeable. For certain working embodiments, the elliptical polarization of the alignment laser is changed by a computer-controlled shifting of polarizing calcite half-wave and quarter-wave plates. After sufficient data have accumulated from one orientation of the sample particles, the polarization is changed to reorient the sample particles by a predictable amount. New diffraction data is then collected from a new orientation of the sample particles, before the cycle is repeated. Changing the laser polarization accomplishes the same function as a goniometer rotating a crystal in x-ray crystallography. In some embodiments the sample ions are introduced into the diffraction zone, and may be introduced at a constant rate, such that with each change in polarization of the alignment laser a new packet of sample ions is introduced. This ensures that the sample ions are not damaged by constant or repeated exposure to either the alignment laser or the electron beam or x-rays of the diffraction imaging system.

F. Alignment and Timing Tools

Several detectors are used to provide information needed for optimizing the fluid droplet formation and for delivering differing types of ions that can be probed in disclosed embodiments of the apparatus. Standard MCP plates can detect non-embedded ions, but cannot detect some exceedingly heavy ions embedded in superfluidic helium. Hence, for certain working embodiments, a current detector will be used to measure the helium-embedded ions in a time-of-flight system. In another embodiments, a Daly dynode biased at high voltage with a channeltron can be used.

IV. General Discussion of One Embodiment of an Apparatus

One aspect of certain disclosed embodiments concerns optimizing cooling of macromolecular ions with superfluidic helium droplets and delivering the ions to an orientation/diffraction zone. The objective is to focus as many macromolecular ions into a diffraction zone with the least amount of residual helium. This involves determining the best operating conditions that allow the complete cooling of macromolecular ions while minimizing the residual superfluidic helium surrounding embedded macromolecular ions to fewer than $10^4$ helium atoms per macromolecule entering the diffraction zone. Minimizing the residual helium both reduces the momentum of embedded ions entering the diffraction chamber and minimizes electron scattering from the helium. Diffraction of the surrounding helium of a doped protein ion can be limited to a manageable degree if the total number of helium atoms is below $10^4$. In an electron beam of 60 keV, the total scattering cross section of a helium atom is 0.08 megabarn, about 7% of a carbon atom (1.2 megabarn). The concentric background of the helium atom diffraction can also be removed through background subtraction during data processing.

Limiting the mass and momentum of the helium droplets containing macromolecular molecules also simplifies the focusing and accumulation of ions into the diffraction zone. The first and only report of trapping proteins in helium droplets estimated the droplet size to be $\sim 10^{11}$ helium atoms moving at a velocity of 207 meters per second. To stop such a massive droplet containing a 20 kDa protein with 10 positive charges would require an impractical stopping voltage of 5,000,000 volts. However, if the helium droplet contains $10^4$ helium atoms, the stopping voltage is only about 5 volts. This allows the embedded ions to be effectively steered and focused by standard mass spectrometric methods and permits many more macromolecules to be held in the diffraction zone for longer.

Disclosed embodiments have been designed to facilitate more efficient mixing and transport through the system while selecting for appropriately sized droplets to be trapped in the diffraction zone. This is achieved using components 1 to 4 in FIG. 1. The design offers considerable flexibility to control the embedding process of macromolecular ions by controlling the following:

The cryostat temperature of the helium nozzle determines the size of the helium droplets (FIG. 1 insert). With a source temperature set to 12 K, the resulting droplets contain approximately 5,000 helium atoms capable of chilling relatively small ions from the ESI source. With certain cryostats, the source temperature may be adjusted to as low as 6 K (or 1 K), which will generate droplets increasing in size to as large as $10^8$ (or $10^{12}$) atoms. Larger droplet sizes are needed to chill bigger macromolecular complexes, with $10^8$ atoms necessary to chill macromolecular ions on the megaDalton scale. Thus, the droplet size is scaled to the macromolecular mass being investigated to provide sufficient helium for chilling.

Pulses of helium droplets are sent down the main axis of the instrument to intercept macromolecular ions confined by the ion trap (component 2 in FIG. 1). The helium droplets have characteristic velocities imparted during their formation that range from 200 to 420 meters per second depending upon their size. The droplet momentum carries droplets down the long axis of the instrument. Charge repulsion between macromolecular ions prevents more than one ion embedded per droplet, but there are an excess of droplets without an embedding ion. Both non-chilled ions and non-doped helium droplets are removed by mass selection, as discussed below.

Helium droplets are then mixed with sample particles where the sample particles are confined by the electric field in the ion trap (component 2 of FIG. 1). The field along the long axis of the ion trap can be adjusted to maximize ion embedding in the helium droplets.

Embedded ions with the desired amount of helium atoms are selected by their mass. If necessary, these ions are accelerated into a size reducer comprised of a set of electrodes and low pressure helium gases. Collisions with the helium gases can strip off the extra helium atoms of an embedded ion. Alternatively, the ions could be ejected from the droplet by resonant laser excitation and non-thermal ejection. The electrodes at the exit of the ion trap or the size reducer can provide a pulsed electrical field to focus the exit ions in space and direct them into the diffraction region. The field from these electrodes and the electrodes downstream from the diffraction region can also slow macromolecular ions embedded in helium to a velocity of 2 meters per second if desired, while empty helium droplets continue moving at >200 meters per second through the system and bare ions are stopped under the same deceleration voltage. By adjusting the magnitude and duration of the electrical pulse, only macromolecular ions containing the appropriate amount of helium enter the diffraction zone during orientation and data collection. Slowing the embedded ions to approximately 2 meters per second allows these ions to remain within the 0.1 mm diffraction zone for the duration of a 50-µs laser orientation pulse.

Figure 5A:
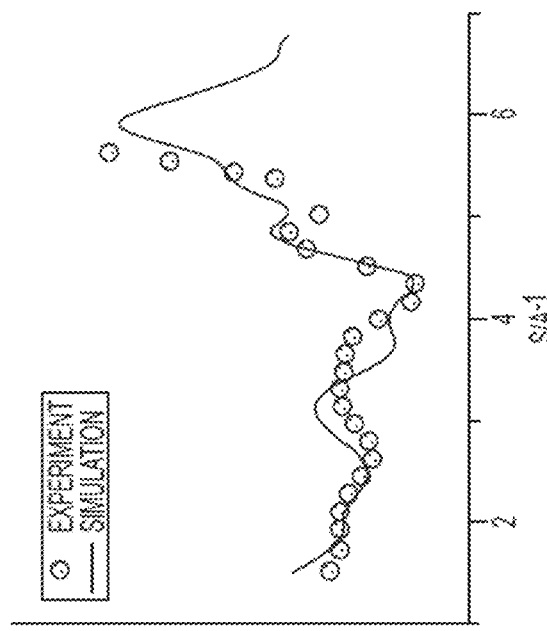
FIG. 5A provides electron diffraction data from pure superfluid helium droplets illustrating the effect of pure superfluid helium droplets on the structure factor: larger droplets with more interior atoms have narrower scattering profiles due to higher packing fractions.
Figure 5B:
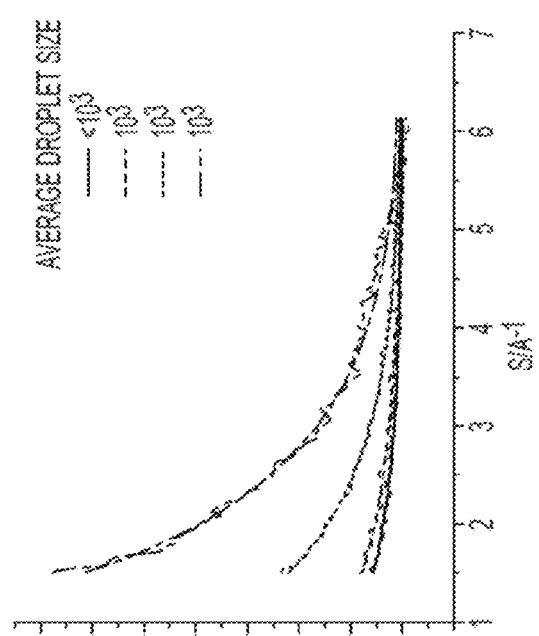
FIG. 5B provides electron diffraction data from PcGaCl embedded in helium droplets. The radial profile of electron diffraction from non-oriented phthalocynine gallium chloride (PcGaCl) embedded in superfluid helium droplets shows the interference rings due to neighboring atoms in the molecule. No laser field was introduced for sample alignment.
Figure 5C:
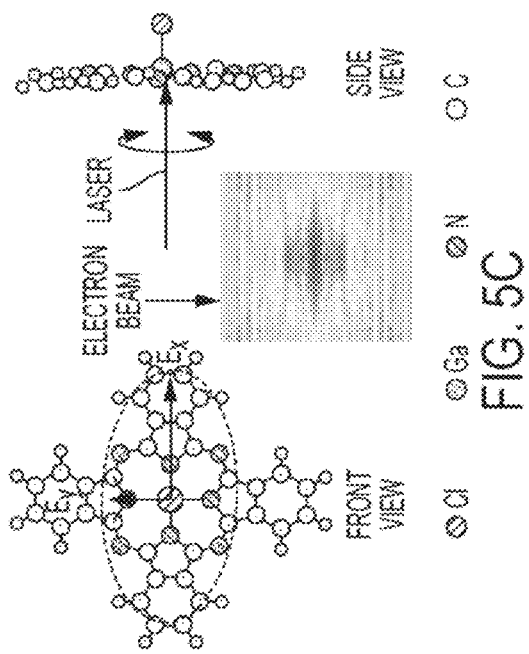
FIG. 5C shows a predicted diffraction pattern for PcGaCl that will be introduced by the laser alignment. The calculated diffraction pattern of laser-aligned PcGaCl shows interference lines instead of rings when the coherent electron beam passes through the spatially defined molecular object. The orientation of the molecular frame is shown relative to the polarization direction of the alignment laser and the electron beam.

Initial alignment is accomplished using small electrosprayed ions such as $Ag^+$ to tune and calibrate the timing of the mass analyzers, ion trap, ion bender and the ion trap. Using a calibrated ion detector, $10^5$ $Ag^+$ ions are routinely trapped for helium embedding at 20 Hz. This provides a simple standard method to troubleshoot the instrument. Once ion transmission has been established, a reference molecule, such as bovine superoxide dismutase (SOD1), can be used because its electrospray characteristics are known (FIG. 2), it is plentiful and it is extremely stable. Operating parameters will be set for SOD1 ions through the system before turning on the helium droplets. One disclosed embodiment of a diffraction chamber is illustrated as components 4-8 in FIG. 1. This system has been used to record the electron diffraction data from pure superfluid helium droplets (FIG. 5A) and from PcGaCl embedded in helium droplets (FIG. 5B) The diffraction data in FIG. 5A are in agreement with neutron diffraction experiments. The data of FIG. 5B establishes that the helium embedding works with the electron diffraction system (*J. Phys. Chem. Lett.*, 5 (2014) 1801). FIG. 5C shows the predicted diffraction pattern for PcGaCl that will be introduced by the laser alignment, which is used to refine the instrument's operation.

Certain disclosed embodiments comprise an orientation and diffraction chamber that incorporates a pulsed electron gun, from about 40 keV to about 60 keV, with a lanthanum boride emitter. Incorporating this gun requires a design that minimizes the generation and exposure of operators to x-rays. Certain disclosed embodiments include a thick platinum aperture to prevent x-ray transmission along the electron path above the diffraction region. Extra shielding also is added around the diffraction chamber to prevent operator exposure.

Certain embodiments concern a diffraction chamber measuring 18 inches in diameter by 30 inches in length. Cold fingers are inserted to improve the vacuum in the diffraction chamber 10-50-fold. In addition, narrow apertures are used to connect the diffraction chamber to the other parts of the instrument to allow differential pumping. The turbo pumps are mounted on extension tubes away from the chamber to prevent the magnetic fields from the spinning blades interfering with the diffracted electrons. A CCD camera having an operating temperature of −90° C. is used in certain embodiments to further reduce the thermal noise of the camera used to collect diffraction images. Several excellent technologies are available for detecting diffraction of single electrons with incredible signal-to-noise ratios. For example, a mid-level intensified CCD camera from Princeton Instrument with fast gating and a two-stage thermoelectric cooler can be used. Other camera systems with greater resolution and lower signal-to-noise can further improve data collection efficiency, particularly for larger protein complexes.

Combining the features described above allows electron diffraction images to be accumulated in less than a minute from plural macromolecules, typically $10^2$-$10^4$ macromolecules, captured per laser pulse. The arrival of the molecule ion packets is spatially aligned and timed within a microsecond of the firing of the laser pulse and the electron beam. Moreover, all beams intersect in a region 0.1 mm$^3$ in size. Timing is controlled by a master clock that triggers four variable timing pulses controlling the release of helium droplets, sample ions and firing of the laser and electron beams. Certain disclosed embodiments are equipped with a variety of sensors, such as a photodiode with a nanosecond response-time, to detect the orientation laser beam, and a current detector in the beam stop to confirm the timing of the electron gun.

Calibration and alignment tools are used to optimize operation without breaking the vacuum; all can be mounted on a rotatable wheel comprising plural receptacles. One alignment tool is a movable phosphor screen that can be positioned 45° to all three beams and that is responsive to macromolecular ions, high-energy electrons and infrared laser light. In addition, both silver and aluminum diffraction specimens are inserted by remote control into the diffraction zone to provide a well-defined diffraction pattern from the electron beam. This allows the atomic dimensions for diffraction on the detector to be precisely and quickly calibrated. A small time-of-flight mass spectrometer can also be fit into one of the receptacles, and with a laser directed in between the ionization region of the mass spectrometer, the exact timing of the ion doped droplets can also be determined independent of the phosphor screen.

By appropriate adjustment of all three beams (doped helium beam, orientation laser beam and the electron beam), several hundred macromolecules can be focused into a diffraction region. This is sufficient for the instrument to work. However, a Digital Ion Trap can also be used within the diffraction chamber (component 4 in FIG. 1) that allows many helium-chilled macromolecules to be trapped in the diffraction chamber. Because square waves raise and hold the electrical field to its maximum much faster and longer than a sine waveform traditionally used in radiofrequency ion traps, the digital trap will more efficiently focus chilled macromolecules to the space-charge limit within the diffraction zone. The waveform and duration of digital square waves of the digital trap can be tailored under computer control and be turned off precisely during the electron beam pulse when diffraction data is being collected. As many as $10^4$ macromolecular ions can be trapped in a 0.1 mm$^3$ diffraction zone. With the high efficiency of electron scattering relative to x-rays, the high level of trapping makes data accumulation extremely rapid. The average distance between macromolecules even at the higher levels of trapping is 12 micrometers, longer than the coherent length of electron sources, thus each macromolecule diffracts independently of the others without multiple scattering events that confound solid samples in electron microscopy. Alternatively, small anions like formate can be injected into the diffraction zone to counter the repulsion of the protein cations to trap more molecules. While entrapping more proteins is desirable, the instrument should work well even if entrapping 100 molecules or fewer per pulse as indicated by the following calculations.

FIG. 6 illustrates how continuous electron diffraction images will appear in reciprocal space. The central axis where the image planes intersect is determined by the direction of the laser beam. The orientation of the diffraction image plane around this axis is controlled by physically rotating macromolecules, which is achieved by changing the elliptical polarization of the laser, i.e., the relative strength of the two electrical fields $E_v$ and $E_h$ (see also FIG. 3).

Figure 6A:
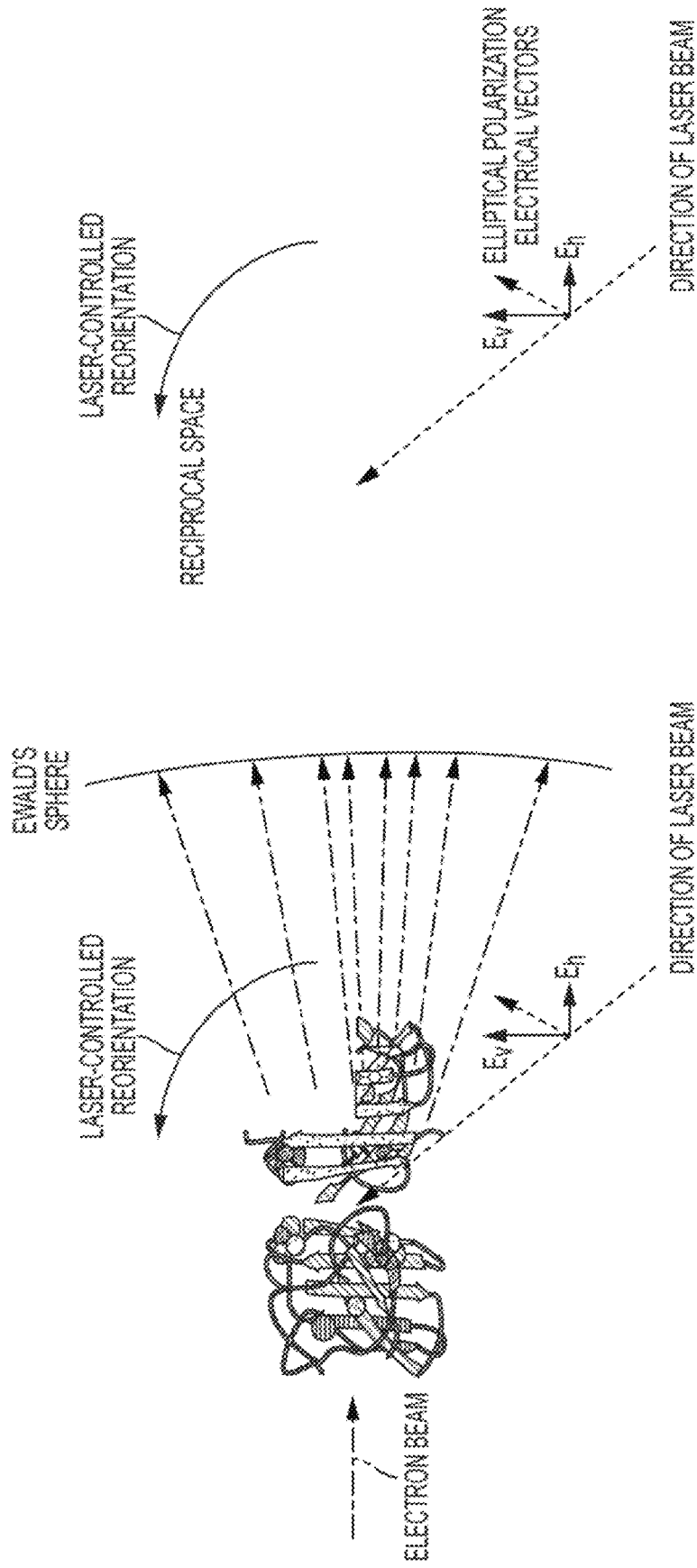
FIG. 6A is a schematic drawing illustrating how continuous electron diffraction images appear in reciprocal space. The central axis where the image planes intersect is determined by the direction of the laser beam. Orientation of the diffraction image plane around this axis is controlled by physically rotating macromolecules by changing the elliptical polarization of the laser, which changes the relative strength of the two electrical fields $E_v$ and $E_h$.
Figure 6B:
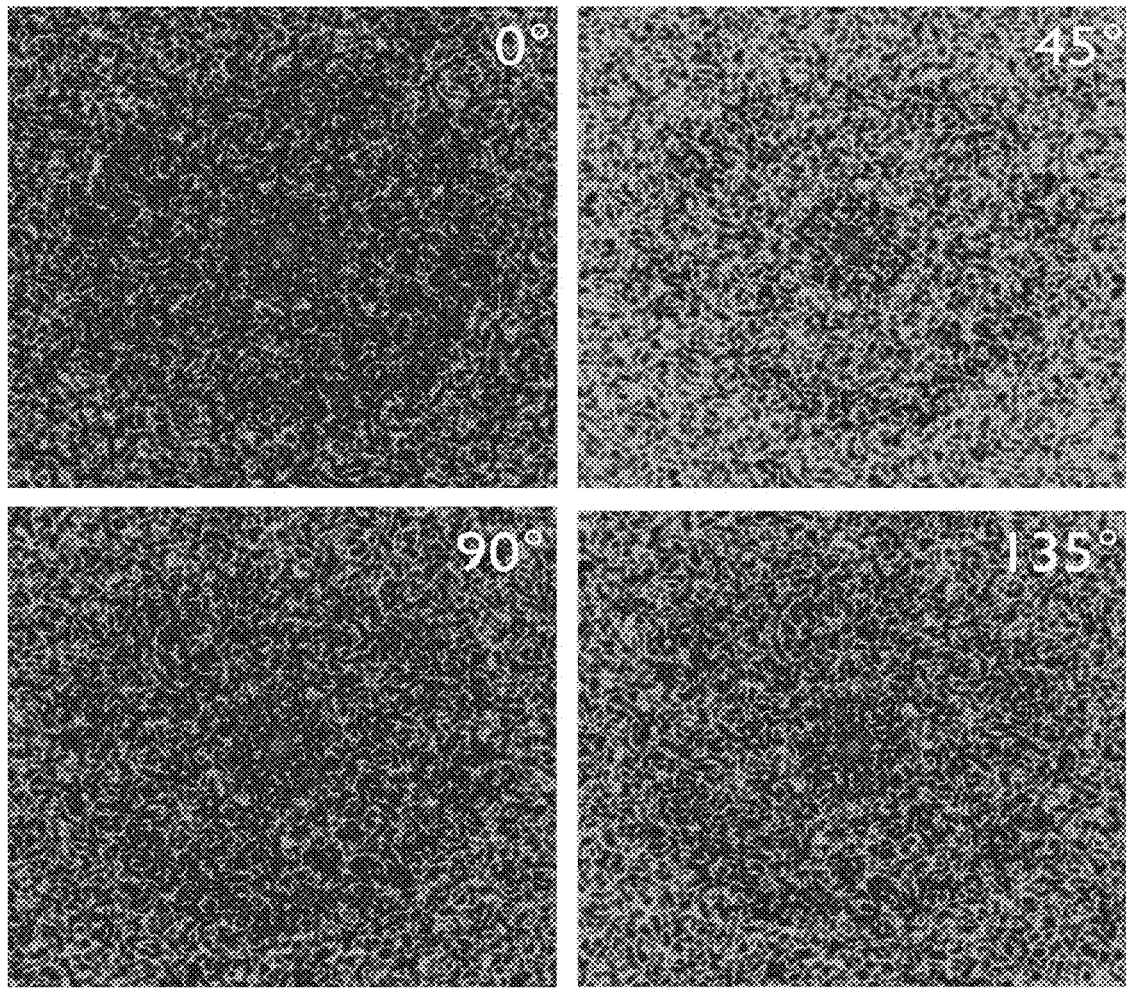
FIG. 6B provides four diffraction images at 45° orientations for SOD1 with intensities colored on a log scale.

Changing the primary polarization of the orientation laser causes the macromolecules to rotate and allows a new continuous diffraction image to be collected that corresponds to the surface of Ewald's sphere that corresponds to elastic electron scattering (FIG. 6A). The wavelength of electrons is sufficiently short that Ewald's sphere (whose radius is set by the reciprocal of wavelength) is nearly flat for scattering out to 1 Ångstrom resolution. The two electrical vectors set by elliptical polarization generate the torque needed to orient the macromolecular ions in a new projection. Hence, the continuous images collected at different orientations will form a pinwheel of image planes rotated in reciprocal space (FIG. 6B). In FIG. 6B, four diffraction images at 45° orientations are calculated for SOD1 with intensities colored on a log scale. A Bayesian statistical approach is used to infer the scattering intensities at a rectangular grid in reciprocal space to extract the phases and solve the structure. Each plane wiggles due to the variation of macromolecular orientation.

Three dimensional phase extraction algorithms have been completed in Matlab™ based upon oversampling methods of Fienup (*Appl. Opt.* 21 (1982) 2758) modified by Miao and Sayre (*Acta Crystallogr., Sect. D. Biol. Crystallogr.* D56 (2000) 1312). The algorithm samples a 3D grid of reciprocal space shown in FIG. 6B. The complete phase extraction algorithm converges within 3-4 hours on an ordinary desktop computer and is robust as reported.

The maximum duration of the orienting laser pulse is 50 microseconds in a current working embodiment, which determines the length of each diffraction experiment. The electron gun can produce 31 electrons per nm$^2$ per 50 μs pulse (this is 30% of the gun's maximum current). As an example, about 378 of these electrons will encounter an SOD1 dimer, based upon its cross section of approximately 12.2 nm$^2$. Scattering from 100 SOD1 molecules in the diffraction region should result in the scattering of approximately 37,800 electrons per laser pulse. In one minute, 1,200 images can be statistically processed to generate a 1 megapixel image from 45 million electrons. The dark current background of the detector will be measured between pulses (data collection occupies only 0.1% of the duty cycle) and thus provide an excellent estimate of the background to correct for noisy pixels.

A single protein tolerates 80 electrons per nm$^2$ before radiation damage is too severe for structure determination by electron microscopy. For disclosed embodiments, the exposure rate is 40% of this dosage. Operating conditions can be adjusted to expose the macromolecules to less radiation and accumulate data longer to assess the impact of radiation damage.

In 3 hours, 180 different images at 1° increments (see FIG. 6) can be collected to fill the reciprocal space with data extending to 1 Å resolution. Once the instrument is tuned to work for a particular sample, little further intervention should be required to produce the initial electron density maps so long as the oversampling phasing algorithms converge. If the instrument is used to determine modifications of known structure, such as ligand binding, data collection and phase solution can proceed even faster. Thus, the instrument might be used for screening large numbers of drug interactions or analyze the effects of many mutations on structure.

Thirty nanomoles of protein at a 1 micromolar concentration are sufficient to collect data for an entire day. Using nanospray interfaces could reduce the protein usage a hundred fold without significantly diminishing the numbers of macromolecular ions in each packet.

V. Working Embodiments of the Disclosed Apparatus

FIG. 1 illustrates one embodiment of an apparatus 10 for determining molecular structure. Apparatus 10 includes a pulsed helium droplet jet generator 12 that produces superfluid helium droplets. Droplet generator 12 includes a low temperature nozzle 14 for generating droplets of a selected size range useful for doping biological molecules. The droplets may move at a speed of from 100 to 300 meters per second, such as about 200 meters per second. Typically, the droplet generator 12 operates at a pressure of greater than 5 bar, such as from 5 to 100 bar. In some embodiments, the pressure is greater than 20 bar, such as from 20 to 100 bar. Also, the droplet generator 12 operates at a temperature of less than 20 K, such as from 1 to less than 20 K. Apparatus 10 further comprises an electrospray source 16 for producing ions of a selected sample. Electrospray ionization is used in mass spectrometry to produce ions, and is particularly useful for producing ions from macromolecules because it can reduce the propensity of such molecules to unfold or denature by adjusting the spray conditions. Biological molecules that are ionized by the electrospray source 16 are then directed to a quadrupole mass analyzer 18, which is coupled in series to a collisional cooling ion trap 20. Cooled sample ions from collisional cooling ion trap 20 are directed to another ion trap 26 for mixing with superfluidic helium droplets produced by helium droplet jet generator 12.

An ion bender 22 is positioned to turn sample ions that are emitted from electrospray source 16 90° prior to mixing with the superfluidic helium droplets. The helium droplets and sample ions then enter the helium-ion trap 26. The helium-ion doped molecules are then focused by electrodes 28 that are coupled in series to helium-ion trap 26.

Doped biological molecule ions and helium droplets are then directed to an orientation and diffraction chamber and ion trap 30, which is coupled in series to the helium-ion trap 26. An alignment laser 32 generates polarized infrared light and directs such light to interact with sample ions embedded in helium droplets as such embedded ions enter the ion trap 30. The combination of DC fields from the ion trap and AC fields from the laser 32 orients biological molecule ions within the ion trap 30. In some embodiments, laser 32 is a Nd-YAG orientation laser with a polarizer and phase retarder. A pulsed electron gun 34 provides electrons that impinge the oriented ions. This results in an electron diffraction image, indicated in FIG. 1 as 36.

Embedded sample ions and helium droplets then exit orientation and diffraction chamber 30 and enter an analytical section of a disclosed embodiment. Embedded sample ions and helium droplets first encounter a second ion bender and mass detector 38. Mass detector 38 detects sample ions exiting from the orientation and diffraction chamber and ion trap 30. Neutral undoped helium droplets are directed to a helium droplet detector 40. During operation the various sections may be independently maintained under a vacuum from about $10^{-4}$ torr to about $10^{-9}$ torr.

Another embodiment of the apparatus, apparatus 2100, is illustrated in FIG. 21. With reference to FIG. 21, the helium droplets pass through a skimmer 2102, which directs only a desired portion of the helium droplet beam to enter ion bender 22. The helium droplets and sample ions are mixed in an electrostatic cone trap 2104 before being focused by pulsed electrodes 28. Apparatus 2100 also includes an analytical section, which includes a focusing lens 2106 connected in series to a time-of-flight component 2108 upstream of a multichannel plate (MCP) detector 38.

Figure 7:
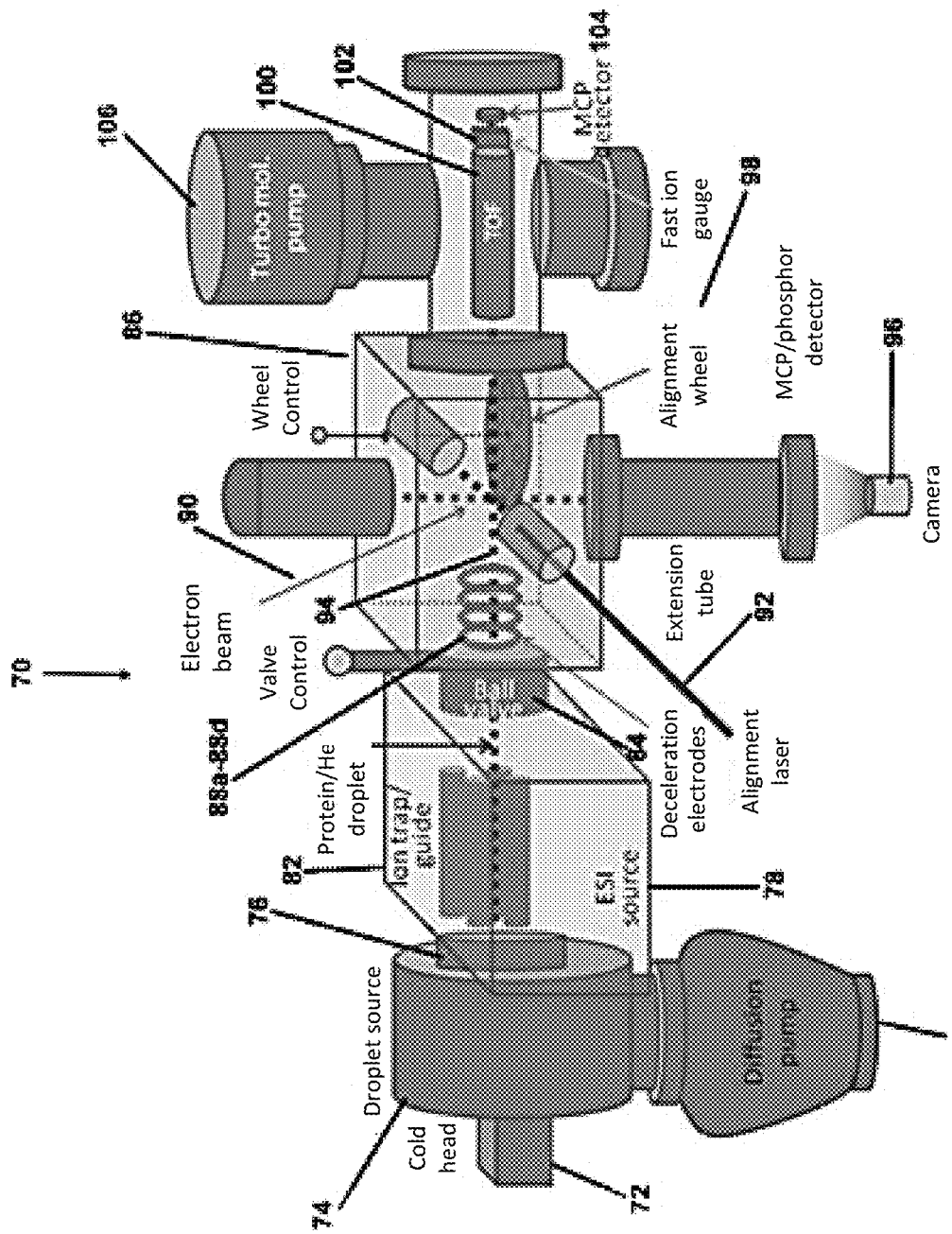
FIG. 7 is a schematic drawing of one disclosed embodiment of an apparatus useful for determining molecular structure, particularly structures of macromolecules, without crystallizing the molecule.

FIG. 7 is a schematic drawing of an apparatus 70 similar to the apparatus of FIG. 1. With reference to FIG. 7, apparatus 70 includes a cold head 72 that is inside to a droplet source 74. Cold head 72 cools high-pressure helium gas in the droplet source to a desired temperature, such as a temperature of about 18 K. A skimmer located inside 76 is mounted between the interface of droplet source 74 and the ESI source 78. Skimmer 76 is essentially a collimator that allows only a desired portion, e.g. a center portion, of a helium droplet beam to enter into an ion trap 82. Diffusion pump 80 is coupled to the droplet source and pumps away helium droplets not selected by skimmer 76. When the apparatus is processing samples, the vacuum in the droplet source 74 is approximately $10^{-5}$ torr.

ESI source 78 generates sample ions that are mixed with helium droplets from droplet source 74. Sample ions are traveling at a direction perpendicular to the direction of travel of the helium droplets from the droplet source 74. Accordingly, an ion bender (not shown in FIG. 7) is positioned downstream of the ESI source 78. The ion bender turns ions 90° from the direction of travel so that they are then traveling in the same direction as helium droplets from droplet source 74. Thus, the helium droplets and the biological molecular ions are fed in-line of ion trap guide 82, and the helium droplet beam merges with the sample ion beam. A portion of the helium droplets merge with the ion beam to form doped droplets comprising helium and sample ions. These doped droplets then travel downstream.

In FIG. 7, helium droplets, molecular ions, and helium droplets doped with sample ions then move through ball valve 84. Ball valve 84 is used to isolate ESI source 78 and ion trap guide 82 from the diffraction chamber 86. Valves such as valve 84 are used to isolate certain sections of the apparatus 70 to allow tuning within each separate section, and further to facilitate maintaining an appropriate vacuum in each section of the apparatus 70.

Helium droplets, molecular ion droplets, and helium droplets doped with sample ions then proceed through a series of electrodes 88a-88d. Electrodes 88a-88d are used to separate helium droplets, molecular ions, and helium droplets doped with sample ions before each proceeds into diffraction chamber 86, and to focus the ion doped droplets into the diffraction region. Pure helium droplets are neutral and are not affected by the electrodes; they move at a constant speed of from about 200 to 400 meters per second across the diffraction chamber. Pure bare ions and ion-doped droplets have very different masses, and thus electrodes 88a-88d have different acceleration effects on these two types of charged particles, which results in different arrival times at the diffraction region. In diffraction chamber 86, pulsed electron beam 90, pulsed laser beam 92, and pulsed ion beam 94 are combined. One aspect of the disclosed embodiments is to accurately time electron beam 90, laser beam 92 and ion beam 94 as they intersect in diffraction chamber 86. The laser beam 92 orients sample ions embedded in helium droplets just prior to electron beam 90 impinging upon the oriented sample ions. As a result, an electron diffraction pattern is produced from the oriented biological molecules.

Camera 96 collects image data from the electron diffraction patterns produced by the electron beam 90 passing through the oriented sample ions 94 in diffraction chamber 86. In one embodiment, camera 96 is a cooled staged camera, whereby in a first stage the camera can be cooled by approximately 30° C. below the ambient working temperature for reducing the detection noise. In another embodiment, camera 96 has a dual stage, whereby the camera is cooled in two stages, with each stage cooling the camera approximately 30° C. below the ambient working temperature. Moreover, camera 96 may be cooled by surrounding the camera with dry ice to further reduce noise received and detected by camera 96.

Apparatus 70 is used to analyze a number of packets of ions as they proceed through the diffraction chamber 86. A sufficient number of packets are processed into diffraction chamber 86 such that an effective electron diffraction pattern image can be achieved at a particular orientation angle based upon the polarization of the laser. Once an effective electron diffraction image is produced at the chosen orientation, then the polarization of the laser beam 92 is changed. A second series of ions is then processed by the apparatus until a second electron diffraction image is recorded. This process is repeated through 180 degrees, thereby producing a series of diffraction images that are processed by software into a final image of the sample molecule.

Apparatus 70 also includes an analytical section at the end of the device. The analytical section is used to ensure that appropriate helium ions and appropriate sample ions are proceeding through apparatus 70. Apparatus 70 includes a time-of-flight component 100 upstream of a fast ion gauge 102 and a multichannel plate (MCP) detector 104. Also coupled to these components is a turbo pump 106, which is used to maintain a suitable vacuum in the analytical section of apparatus 70. These components allow back-end analysis to determine that helium droplets and helium droplets doped with sample ions are proceeding through apparatus 70 as desired. Helium ions are neutral, and cannot be manipulated by any of the ion optics. Helium droplets also do not generate a signal on MCP detector 104. Thus, an ion gauge 102 ionizes the neutral helium droplets. The ionized helium droplets are then detected by the MCP detector 104. Fast ion gauge 102 can be upstream or downstream of the time-of-flight component 100.

Figure 8:
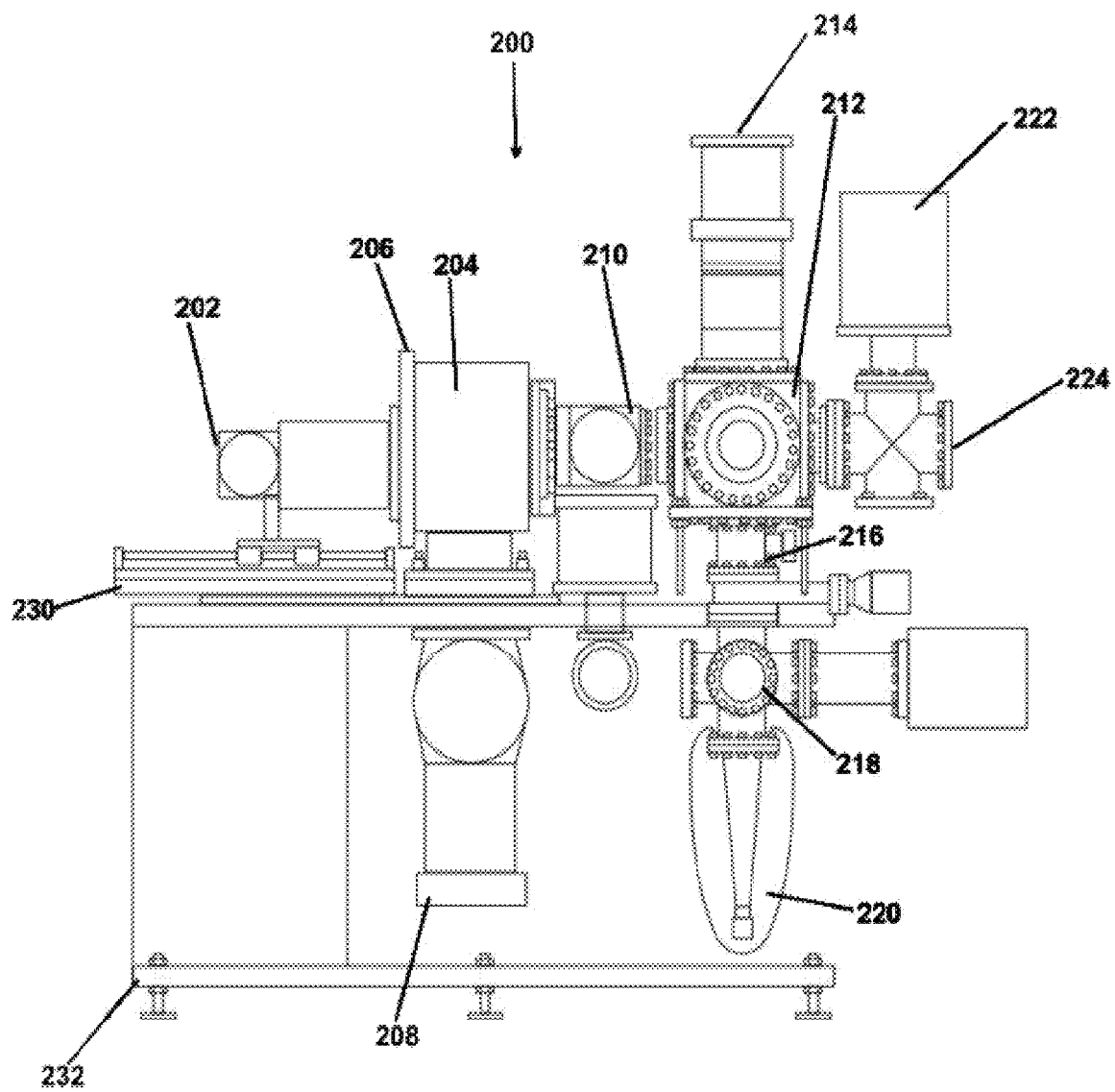
FIG. 8 is a side view of one disclosed embodiment of an apparatus useful for determining molecular structure, particularly structures of macromolecules, without crystallizing the molecule.

FIG. 8 is a side view of apparatus 70 of FIG. 7. With reference to FIG. 8, apparatus 200 includes a cold head 202 that is coupled to a helium droplet source chamber 204. Diffusion pump 208 is coupled to the helium droplet source chamber 204 and draws helium droplets not selected by skimmer into pump 208.

An ESI source 210 (partially shown) is downstream of and coupled to droplet source chamber 204. An ion bender is positioned downstream of the ESI source. The ion bender deflects biological molecule ions, which then mix with the helium droplets from droplet source 204. A portion of the helium droplets merge with the ion beam to form doped droplets comprising helium droplets and sample ions. These doped helium droplets then travel downstream.

Helium droplets, molecular ions, and helium droplets doped with sample ions then move through ball valve 210. Ball valve 210 isolates ESI source and ion trap guide from the diffraction chamber 212.

Coupled to diffraction chamber 212 is an electron gun 214. In the embodiment of apparatus 200 as illustrated in FIG. 8, the electron gun is a Zeiss TEM electron gun. In other embodiments, and as discussed in more detail below, the Zeiss electron gun is replaced with a Kimball Physics electron gun, such as Model No. EGH-6210. Below the diffraction chamber 212 is an isolation gate valve 216 to isolate the diffraction chamber from manipulator 218. Manipulator 218 is attached to a retractable fluorescence screen to assist with electron beam alignment. Camera 220 obtains data from the electron diffraction that occurs when a pulsed electron beam, a pulsed laser beam, and a pulsed ion beam combine in the diffraction chamber 212.

Apparatus 200 also includes an analytical section at the end of the device, as discussed above for apparatus 70. The analytical section includes turbo pump 222 and analytical section 224. Certain disclosed embodiments of apparatus 200 include in the analytical section 224 a time-of-flight component, a fast ion gauge and an MCP detector.

FIG. 8 also illustrates that the apparatus 200 is positioned on a support system. The support system of the illustrated embodiment comprises a top cart rail 230 and a bottom cart rail 232.

Figure 9:
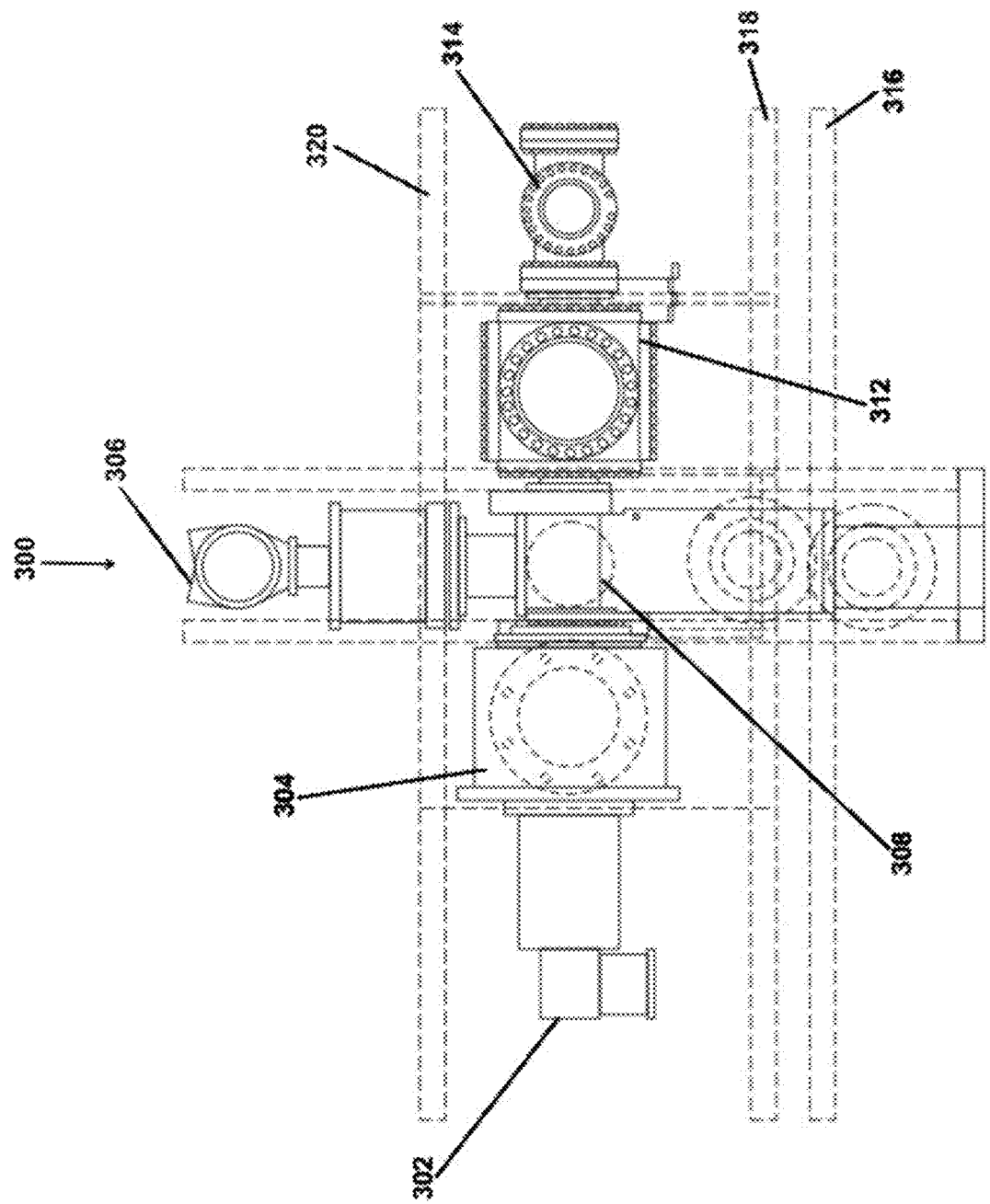
FIG. 9 is a top view of one disclosed embodiment of an apparatus useful for determining molecular structure, particularly structures of macromolecules, without crystallizing the molecule.

FIG. 9 is a top view of an apparatus similar to that illustrated in FIG. 8. Apparatus 300 includes a cold head 302 that is coupled to a helium droplet source chamber 304. A diffusion pump is coupled to the helium droplet source chamber 304.

The embodiment of FIG. 9 does not include the components of an ESI source, as it is designed for use with small neutral molecules. The vacuum chamber of the ESI source 308, on the other hand, is used to house the neutral sample. Accordingly, the device 300 includes a cryopump 306 that is coupled to the ESI chamber 308. Downstream of the ESI chamber 308 is a diffraction chamber 312. An electron gun is coupled to the diffraction chamber. Again, as with previous embodiments, apparatus 300 includes an analytical section 314 at the end of the device. FIG. 9 illustrates that the support system comprises support rails 316, 318 and 320.

Figure 10:
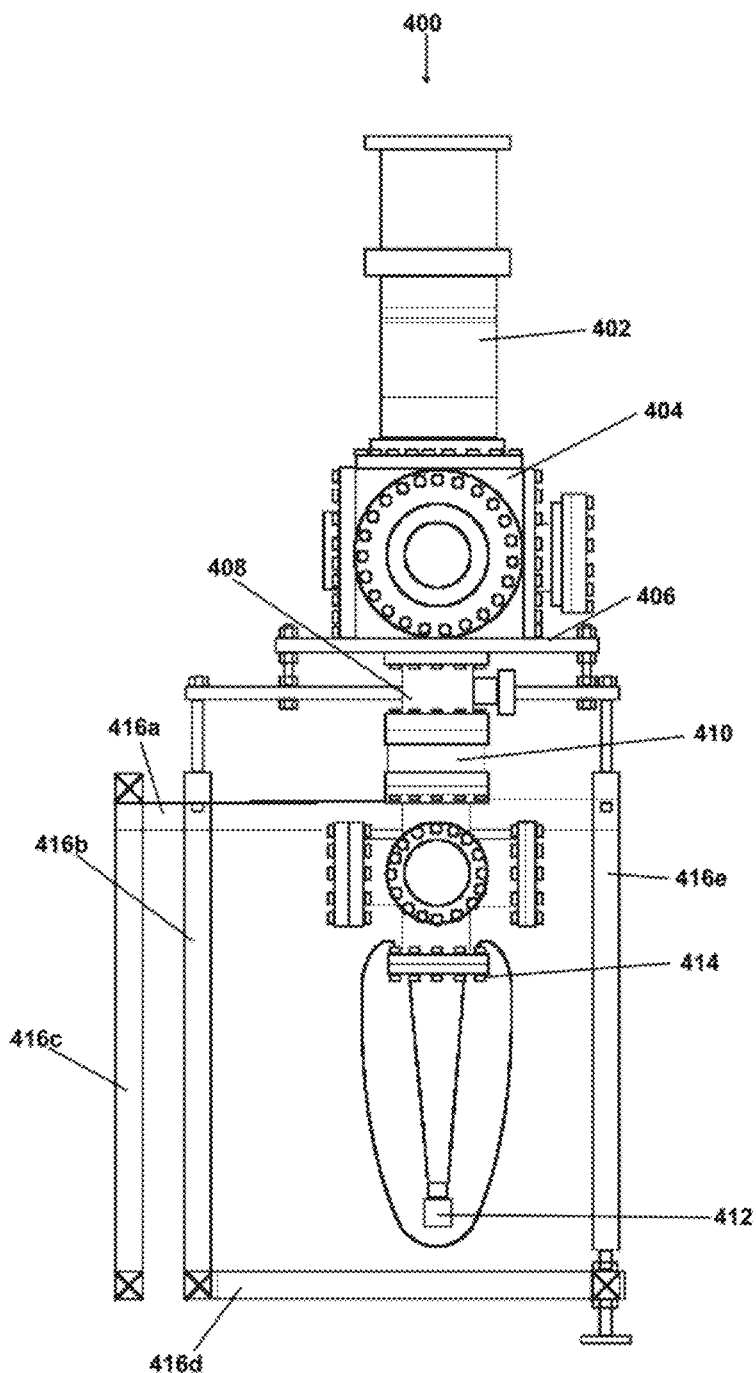
FIG. 10 is an end view one disclosed embodiment of an apparatus useful for determining molecular structure, particularly structures of macromolecules, without crystallizing the molecule.

FIG. 10 is a cross section of a portion of the device illustrated in FIG. 8. An electron gun 402 is coupled to a diffraction chamber 404 mounted on plate 406. A T-adaptor 408 is positioned below plate 406. Gate valve 410 isolates diffraction chamber 404 from MCP detector 414, and camera 412 is enclosed in a light-tight shroud. FIG. 10 also illustrates support members 416a-e for supporting components of apparatus 400.

Figure 11:
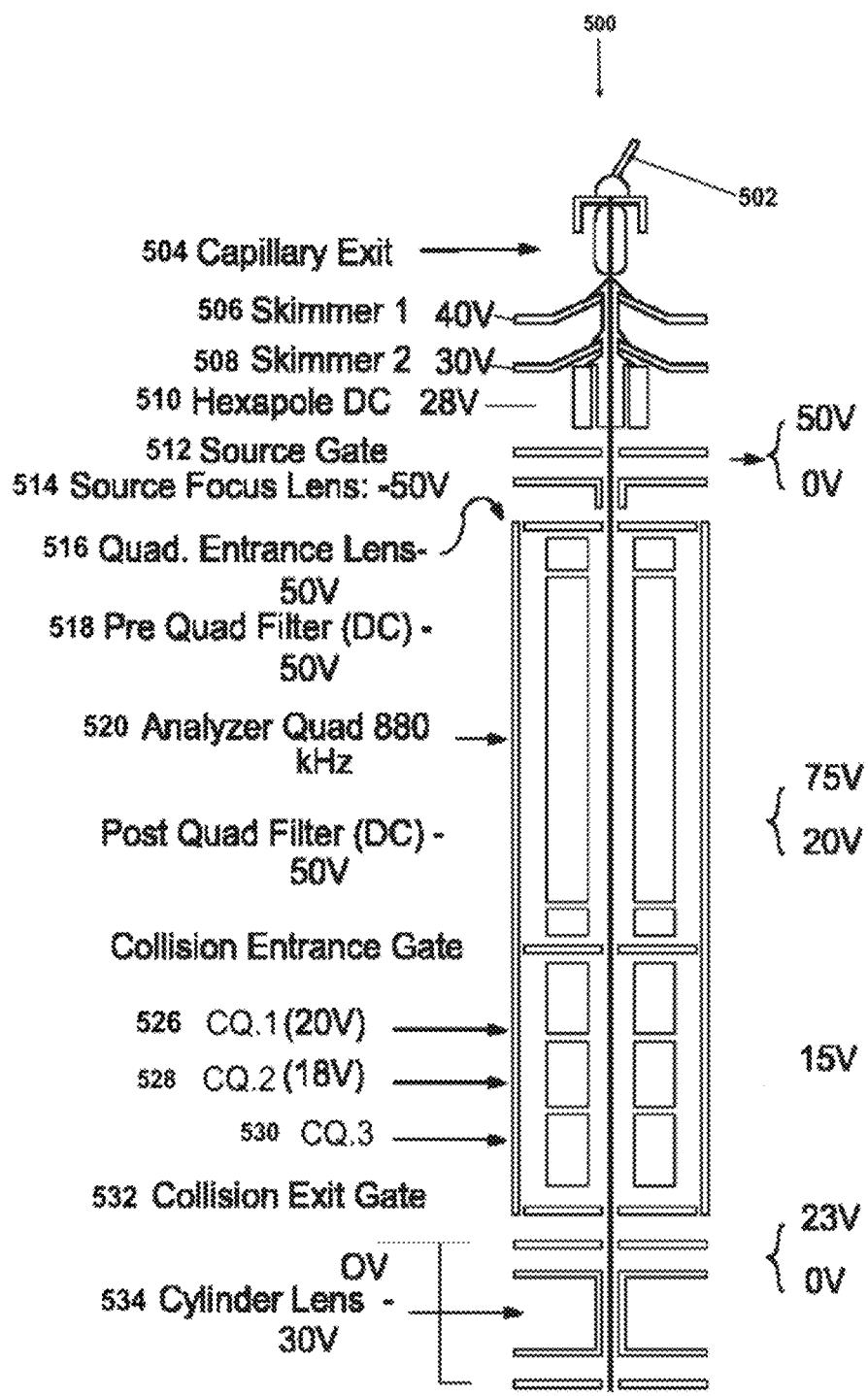
FIG. 11 is a schematic cross sectional drawing of one embodiment of an electrospray ionization source.

FIG. 11 is a schematic cross section of one embodiment of an electrospray ionization injection system 500, which is available commercially, such as from Bruker. System 500 includes an injector 502 for injecting ions into the system through capillary exit 504. At least one skimmer, and perhaps plural skimmers, is used to select ions injected into the system 500. The embodiment 500 includes a first skimmer 506 and a second skimmer 508. Downstream of skimmers 506 and 508 is a 28 volt hexapole guide 510.

An ion source gate 512 is positioned downstream of hexapole 510. Source gate 512 is either at 0 volts or 50 volts to allow ions to either pass through or not. Ions passing through source gate 512 enter analyzer quad 520 by first passing through a source focus lens 514, a quad entrance lens 516, and prequad filter 518.

Ions in the system 500 are moving quite fast. In certain embodiments, an inert gas, such as nitrogen, is introduced into system 500. Traveling ions collide with the inert gas and lose some of their kinetic energy. Ions can be continuously introduced into the system, and can be stored in areas 526, 528 and 530. Eventually, ions exit through collision gate 532. Collision gate exit 532 thereby acts as a timing control for ions entering the diffraction chamber.

System 500 includes an einzyl lens 534. The top and bottom of einzyl lens 534 are at 0 volts. The center of einzyl lens 534 is at 30 volts. Einzyl lens 534 focuses ions on the center axis of the system so that ion spread is minimized without affecting the kinetic energy of the ions. Ions departing system 500 through einzyl lens 534 enter an ion bender (not shown in FIG. 11), which turns the ions 90°. The ions are then mixed with helium droplets prior to entering the diffraction chamber.

Figure 12:
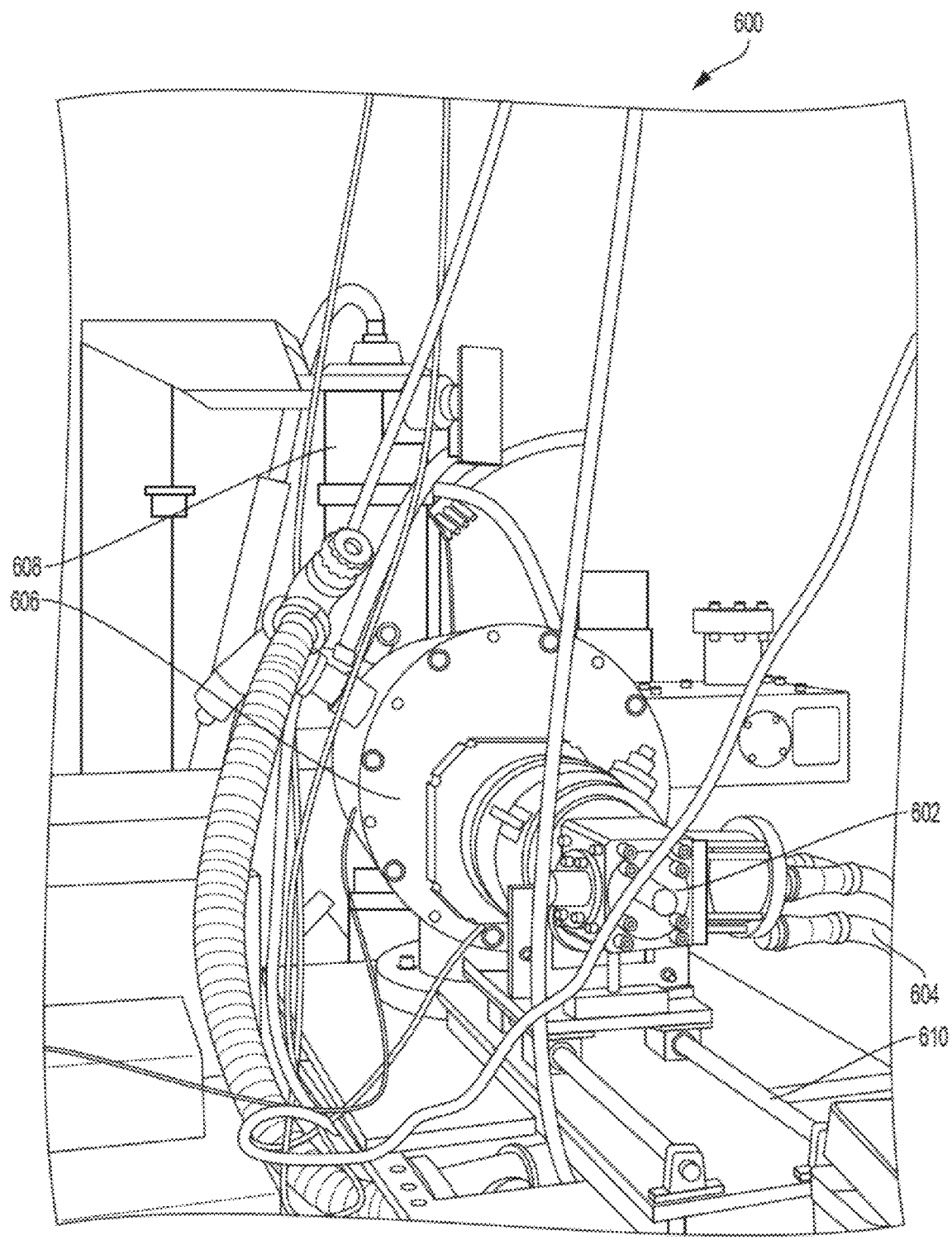
FIG. 12 is a photograph of one disclosed embodiment of an apparatus useful for determining molecular structure, particularly structures of macromolecules, without crystallizing the molecule.

FIG. 12 is the image of one embodiment of an apparatus shown in FIGS. 8-10 for determining structures of neutral samples. Apparatus 600 includes a cold head 602, which is coupled to a compressor (not shown) by compressor lines 604. Apparatus 600 includes a helium droplet source high vacuum chamber 606. Apparatus 600 also includes electron gun 608. Components of apparatus 600 are supported on rail system 610.

Figure 13:
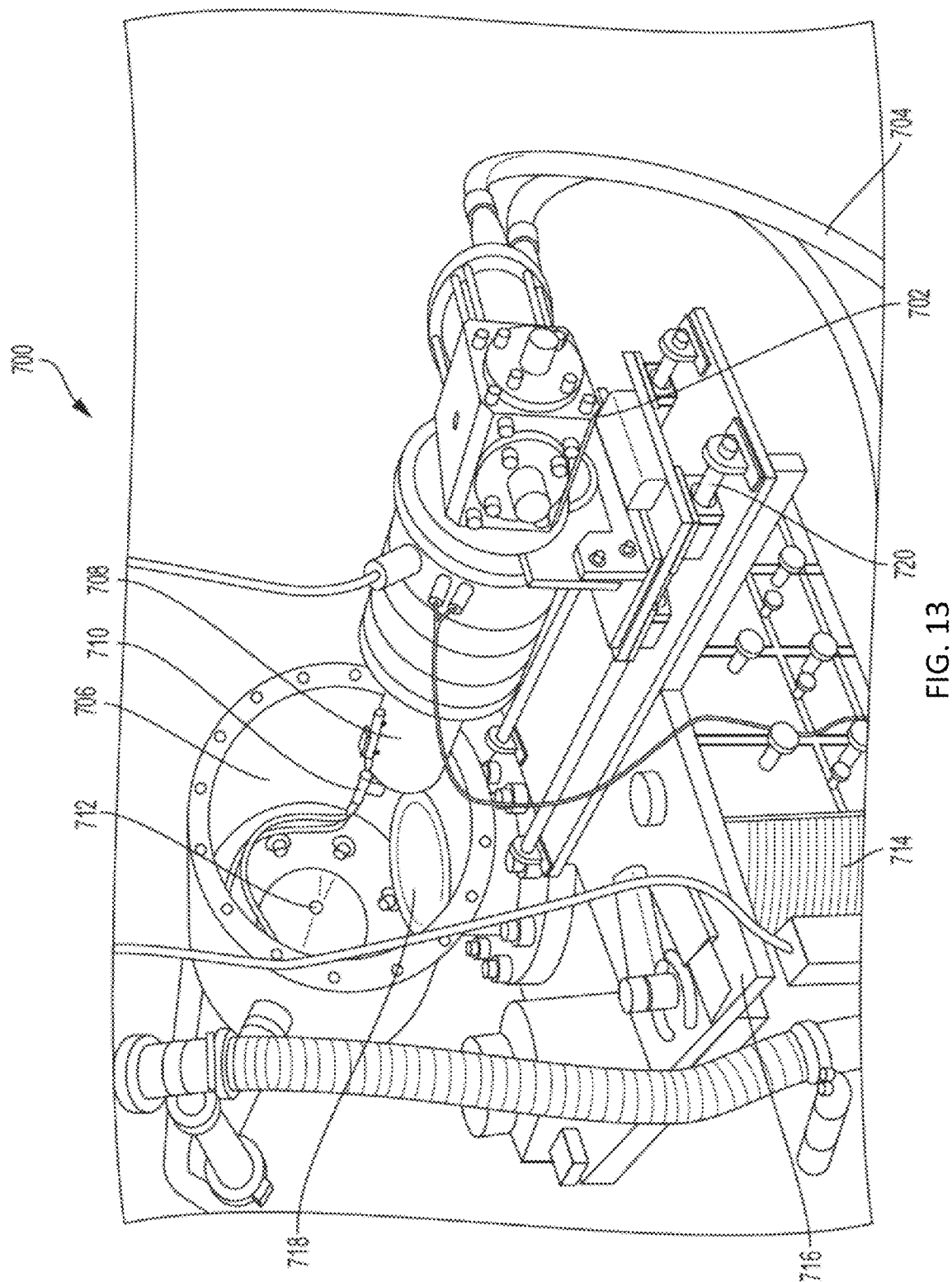
FIG. 13 is a photograph of the inside of a one disclosed embodiment of an apparatus useful for determining molecular structure, particularly structures of macromolecules, without crystallizing the molecule.

FIG. 13 is an image of one embodiment of an apparatus 700 for determining structure of samples according to the present invention. FIG. 13 shows the interior of the helium droplet source chamber 706. Apparatus 700 includes a cold head 702, which is coupled to a compressor (not shown) by compressor lines 704. Apparatus 700 also includes cold shield 708 for a cold head (not shown), which is cooled to a desired temperature, such as 20-50 K. Pulsed valve 710 provides pulses of helium gases at 10-80 atmospheres of pressure. Skimmer 712 selects portions of the helium droplets introduced into the system 700 by pulsed valve 710 for mixing with sample ions.

Diffusion pump 714 is positioned beneath support table 716. Diffusion pump 714 is a hot oil pump, and can introduce oil into the diffraction chamber. Accordingly, apparatus 700 also includes a cooling coil 718 to condense oil and prevent it from entering the diffraction chamber. Apparatus 700 also includes support rail system 720.

Figure 14:
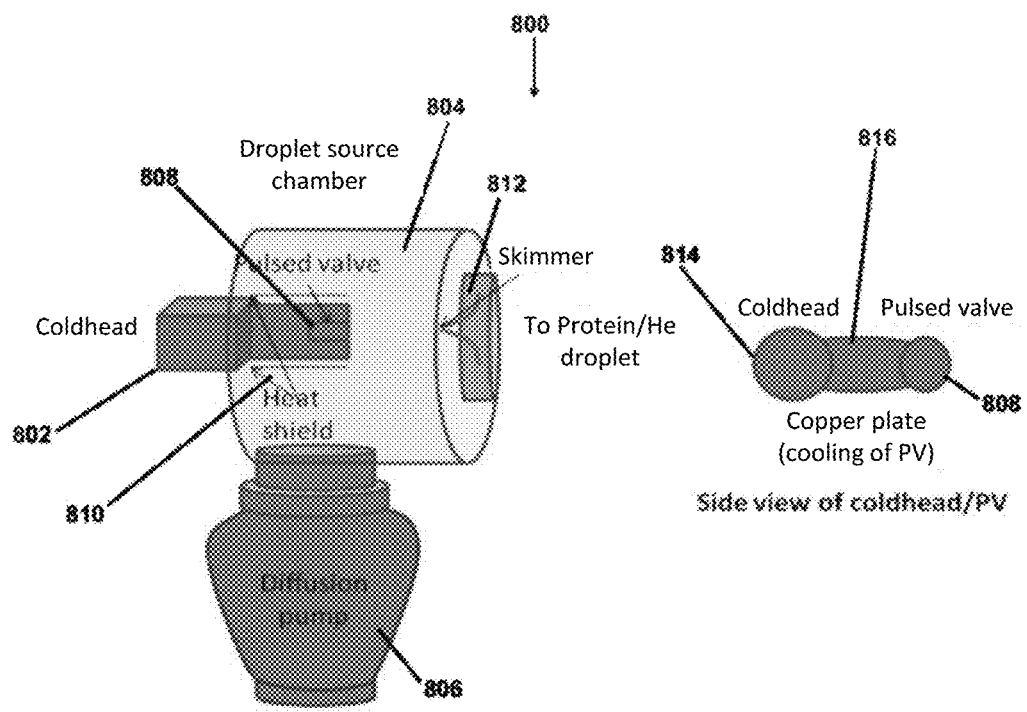
FIG. 14 is a schematic drawing of a superfluid helium droplet source used in one disclosed embodiment.

FIG. 14 is a schematic drawing illustrating one embodiment of a droplet source 800. Source 800 includes cold head 802 and chamber 804. Diffusion pump 806 is effectively coupled to the chamber 804. Positioned inside chamber 804 is pulsed valve 808. Heat shield 810 is used to keep the low temperature of the pulsed valve within the chamber 804. Helium droplet skimmer 812 selects portions of helium droplets emitted by actuation of pulsed valve 808.

Cold head 802 includes mounting flange 814. Cold head 802 is coupled to pulsed valve 808 by a copper plate 816, which cools the pulsed valve 808.

Figure 15:
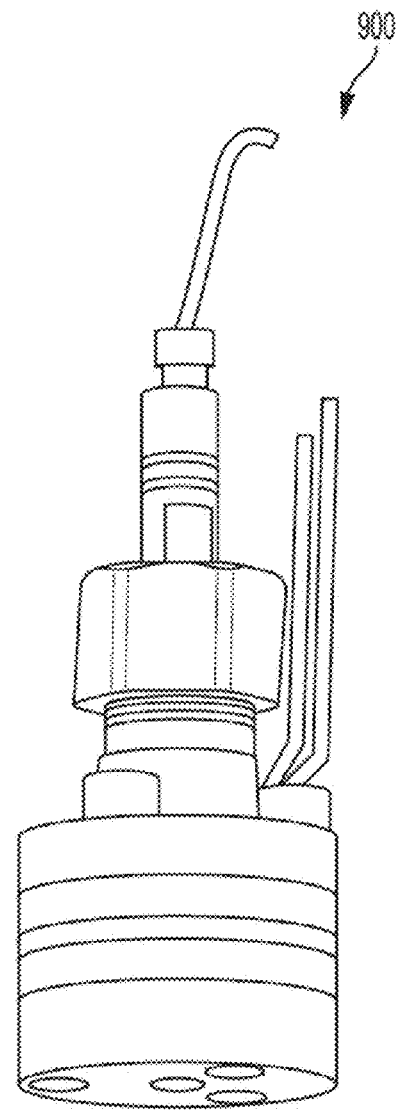
FIG. 15 is a schematic drawing of a pulsed valve used in one disclosed embodiment.

FIG. 15 is a schematic illustration of one embodiment of a pulsed valve 900. Valve 900 has a short duration opening time of about 10-20 microseconds. Valve 900 also can withstand substantial pressures, such as pressures ranging up to at least about 100 atmospheres. Valve 900 also can operate at high frequencies, such as several thousand Hertz.

Figure 16:
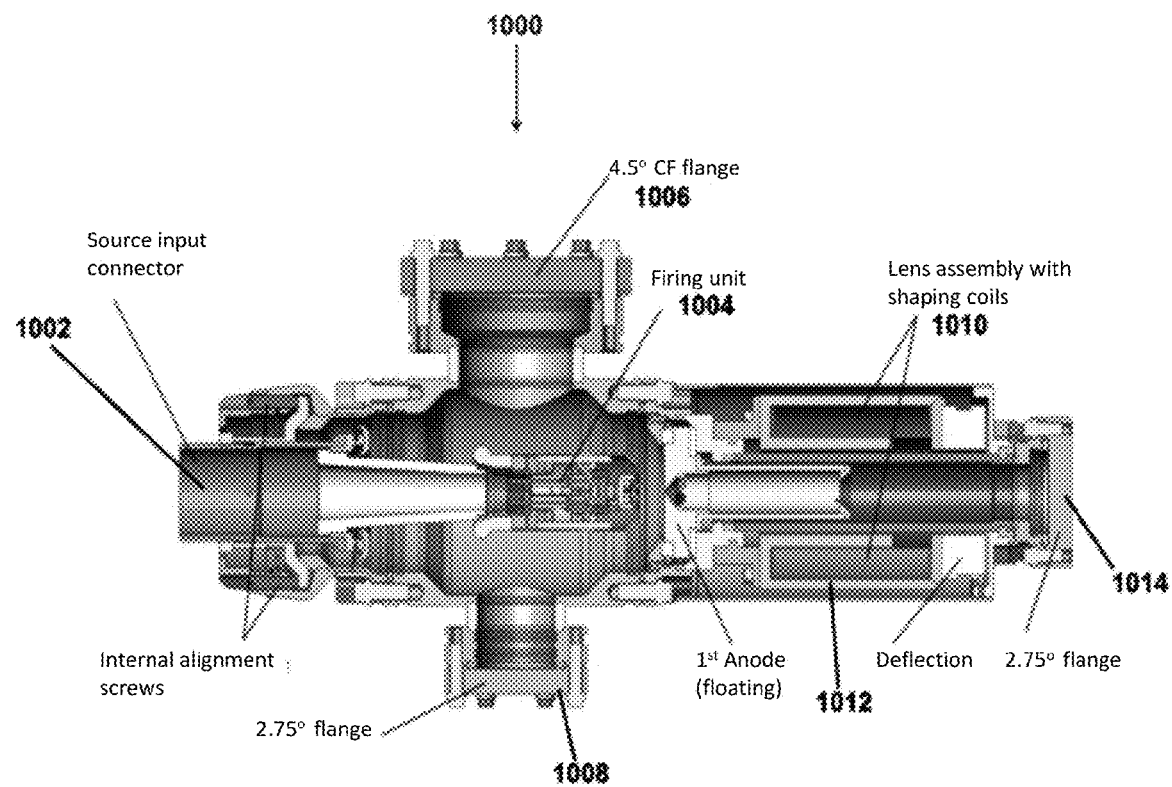
FIG. 16 is a schematic drawing of one embodiment of an electron gun used in one disclosed embodiment.

FIG. 16 is a schematic cross section of a Kimbell Physics electron gun 1000, Model No. EGH-6210. Electron gun 1000 includes a source input connector 1002 for a power supply cable, which provides up to 60 kV to the gun 1000. Gun 1000 includes a firing unit 1004. Unit 1004 includes a lanthanum boride crystal that is heated to a temperature from 1,000 to 2,000° C., resulting in electron emission. An electron grid allows electrons to pass or not, and can be pulsed to provide an electron pulse at a desired time for a desired duration. A pump (not shown) is connected to the electron gun 1000 by flange 1006. A pump is coupled to the gun to help prevent contamination of the electron emitting crystal. Gun 1000 also is connected to an ion gauge (not shown) by flange 1008. The pressure of the gun 1000 is continuously monitored, and in certain working embodiments the pressure is about $4\times10^{-8}$ torr.

Gun 1000 includes a lens assembly 1010. Lens assembly 1010 includes shaping coils 1012. Coils 1012 generate a magnetic field to collimate and focus electrons emitted by the crystal. Certain disclosed embodiments add a second lens assembly to further collimate and focus electrons emitted by the crystal. Electron gun 1000 interfaces with the remaining components by connecting at flange 1014.

Figure 17:
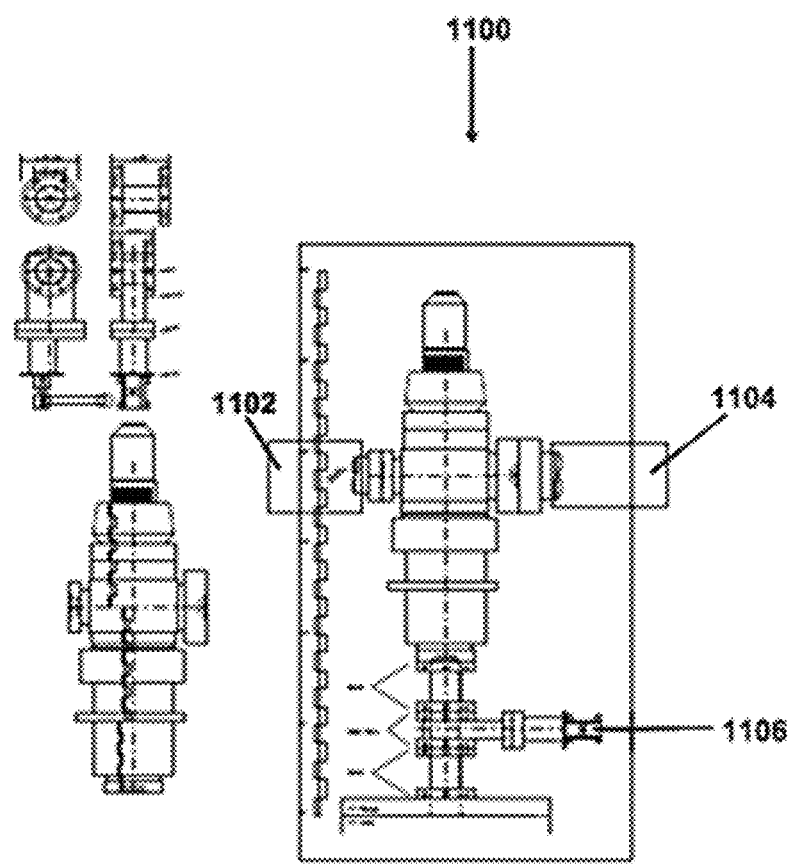
FIG. 17 is a drawing of the electron gun of FIG. 16.

FIG. 17 is a drawing of the electron gun 1100 schematically illustrated in FIG. 16. Gun 1100 includes a vacuum gauge 1102. Gun 1100 also is effectively coupled to pump 1104. Gate valve 1106 allows isolation of the gun 1100 from the other components, such that the $4\times10^{-8}$ torr vacuum can be maintained and still allow operator access to other apparatus components.

Figure 18:
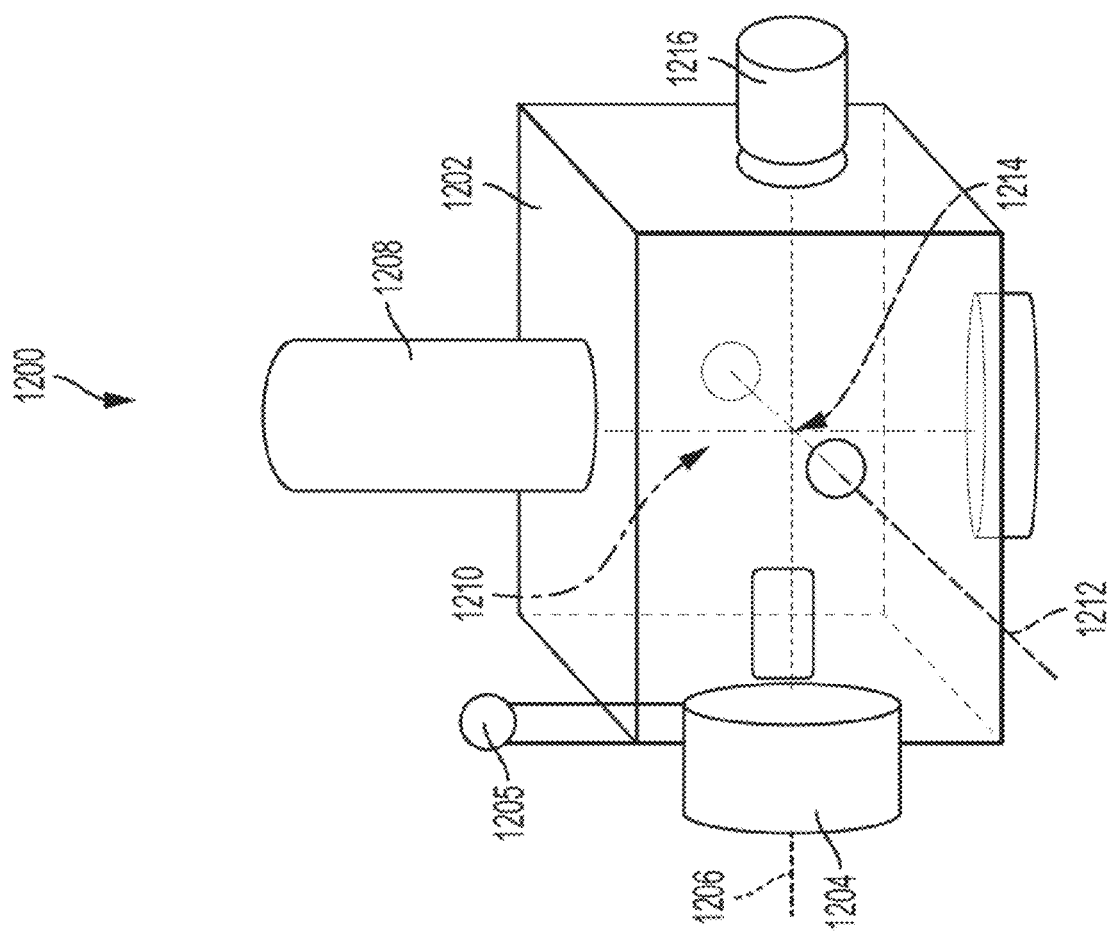
FIG. 18 is a schematic drawing of one embodiment of a diffraction chamber used in one disclosed embodiment.

FIG. 18 is a schematic drawing of one embodiment of a diffraction unit 1200. Diffraction unit 1200 includes a chamber 1202. Ball valve 1204, controlled by valve control 1205, controls passage of a helium doped sample ion beam 1206 into the diffraction chamber 1202. Coupled to the chamber 1202 is electron gun 1208, which emits an electron beam 1210 that enters chamber 1202.

A laser (not shown) is coupled to chamber 1202. An excitation laser can be used to tune the device, an orientation laser can be used to orient sample molecules in the diffraction chamber, or a tunable laser can be used to emit both excitation and orientation beams. The illustrated embodiment shows diffraction chamber 1202 receiving an excitation laser beam 1212. Beams 1206, 1210 and 1212 intersect in a center portion 1214 of chamber 1202.

FIG. 18 illustrates that the unit 1200 includes a photomultiplier tube 1216. FIG. 18 does not illustrate the diagnostic components that typically are coupled to unit 1200 in working embodiments, but instead illustrates a photomultiplier tube 1216 coupled to the unit 1200. Photomultiplier tube 1216 facilitates checking the timing of the unit. For example, a neutral molecule may be embedded into the helium droplet beam, and the doped helium droplets pass through ball valve 1204. The beam is then excited with a tunable laser in the visible region, such as at 600 nanometers, rather than the 1064 nanometers used to align molecules in the chamber 1202. The excitation laser excites the sample molecule to a non-ground state condition; the excited molecule then emits a photon to return to ground state. The photomultiplier tube 1216 detects photons emitted by the excited neutral molecules; photon emission only happens after excitation occurs. Photon emission is almost instantaneous on the operation time scale, such as within a few nanoseconds. This allows determination of when the calibration molecule enters chamber 1202, thereby facilitating timing the intersection of the electron beam and the doped helium droplets.

Figure 19:
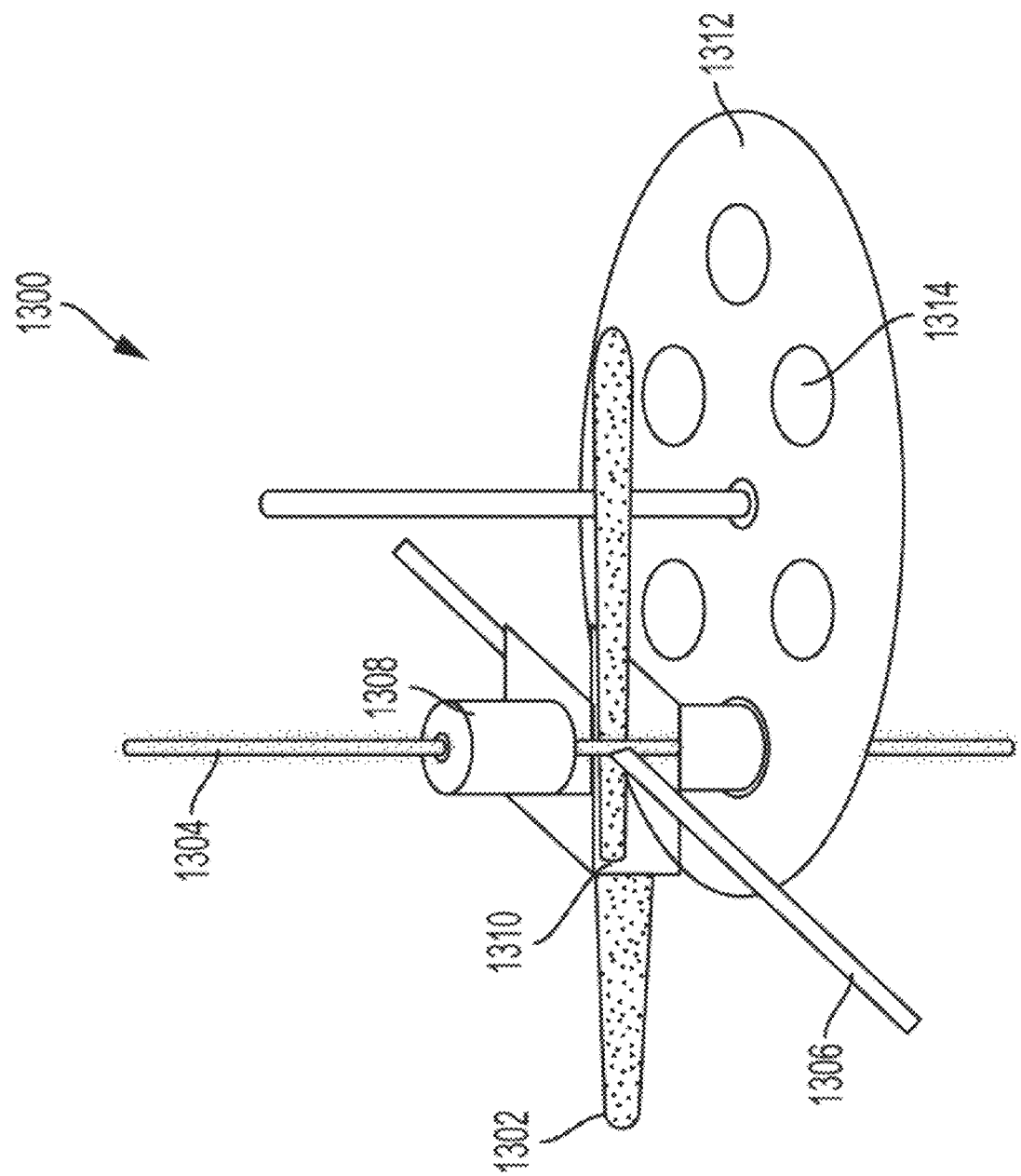
FIG. 19 is a schematic drawing illustrating one embodiment of an alignment wheel for calibrating samples and beam alignment used in one disclosed embodiment.

FIG. 19 illustrates one embodiment of a diffraction unit 1300. Doped helium droplets 1302, exemplified by protein-doped helium droplets, enter the diffraction unit 1300. An electron beam 1304 and an alignment laser beam 1306 also enter the unit 1300. Graphite tube 1308 helps ensure that the electron beam 1304 is clean, concentrated and properly aligned.

Unit 1300 also includes a slit 1310 to minimize spread of the doped helium droplets 1302 entering diffraction zone. Some spread can be tolerated in the unit 1300, but too much spread of the doped helium beam blurs the diffraction image that is produced.

Unit 1300 also includes a wheel 1312 with plural receptacles 1314. A Faraday cup (not shown), for example, can be housed in one of the receptacles 1314. A Faraday cup is used to determine the number of electrons included in the beam 1304. A phosphor screen also can be placed in a receptacle 1314 to image electrons that can be used for correct timing the electron beams—with the doped helium droplets 1302 and the laser beam. A standard TEM sample also can be housed in one of the receptacles 1314.

Figure 25:
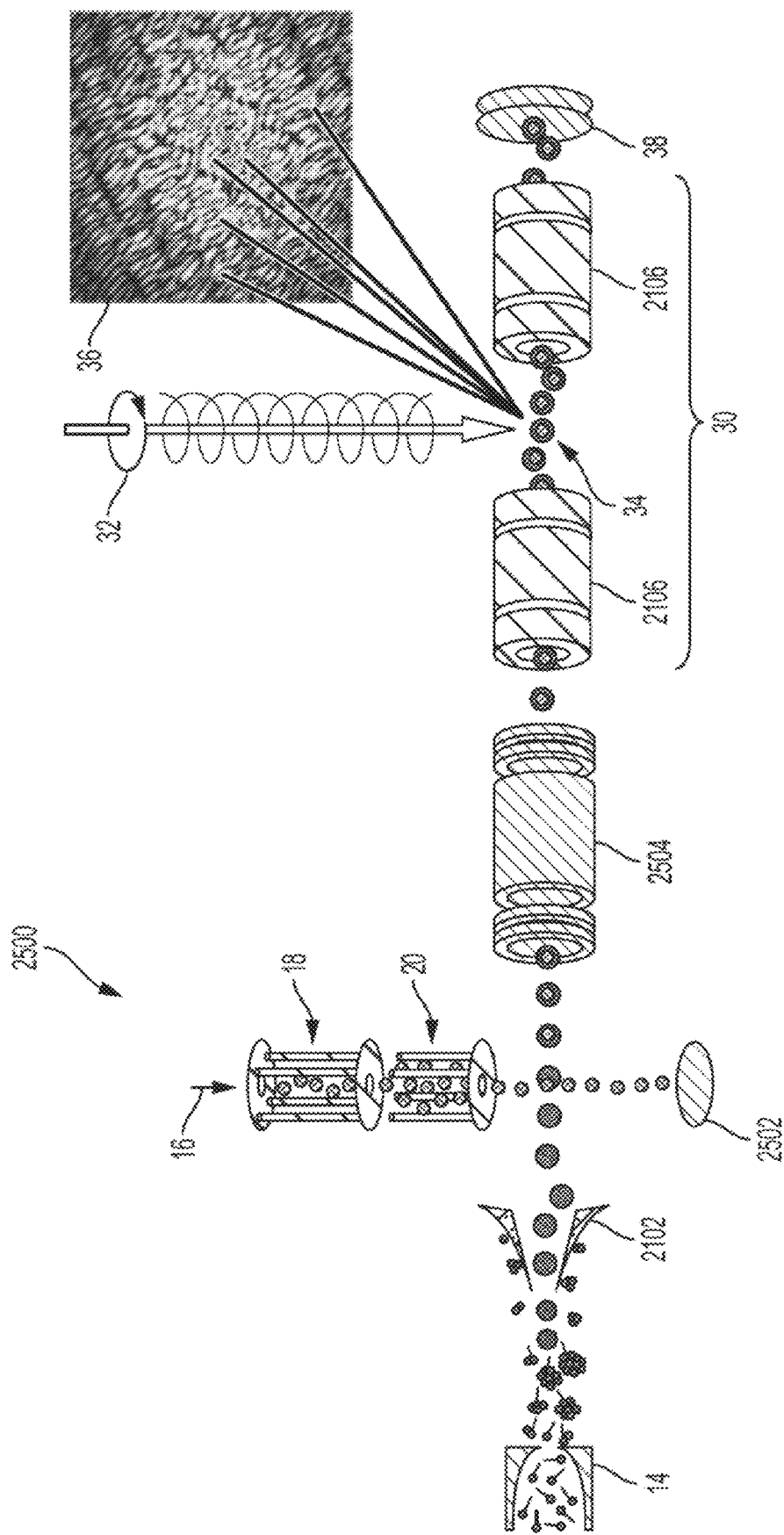
FIG. 25 is a schematic drawing illustrating certain components of an alternative embodiment of an apparatus for determining molecular structure.

FIG. 25 is a schematic drawing of another possible configuration 2500 of the apparatus. Ions from the ESI source 16 are released into the path of the droplet beam, slowed down by the end electrode 2502 facing the ion source, and picked up by the droplets. The size of the ion embedded droplets can be further reduced by a size reducer 2504 downstream via collisions with low pressure helium gases. The ions of appropriate sizes are then chosen by the pulsed electrodes and directed into the next region.

Figure 26:
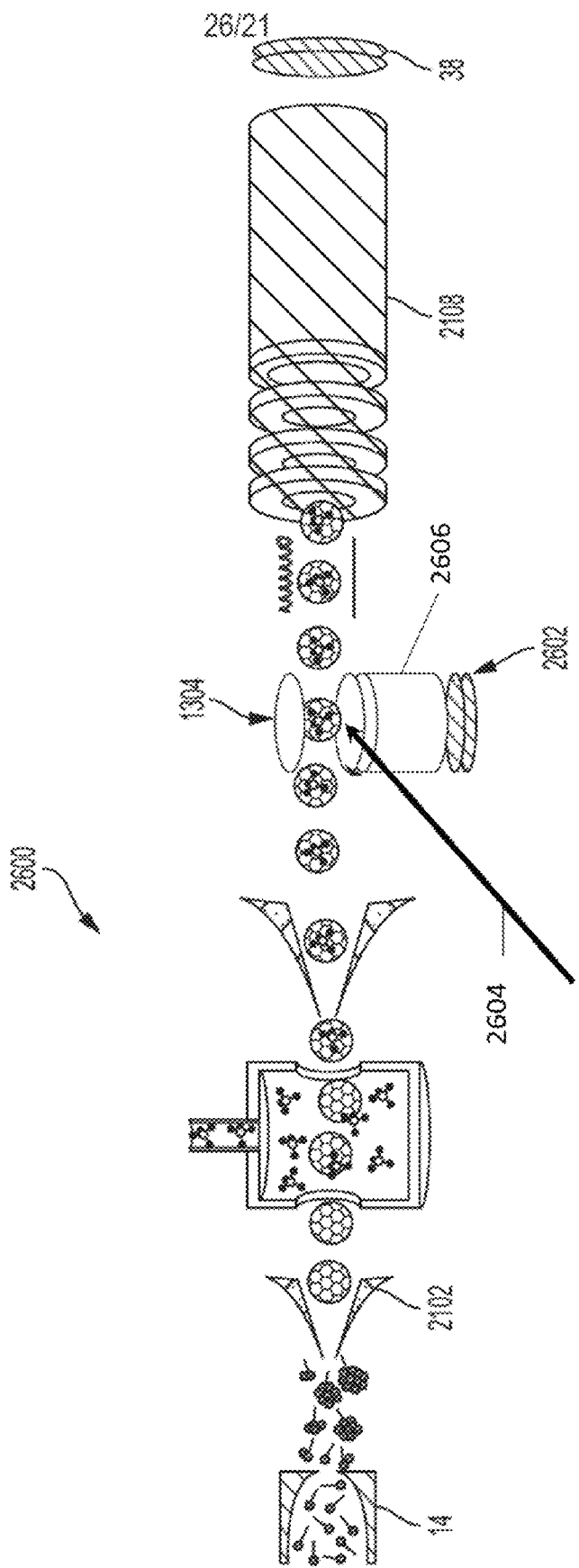
FIG. 26 is a schematic drawing illustrating certain components of a disclosed embodiment of a laser ionization time-of-flight spectrometer for timing determination of doped droplets.

FIG. 26 provides a schematic diagram of a diagnostic configuration of an apparatus 2600 comprising an excitation laser 2604 and two time-of-flight mass spectrometers: one with laser ionization (laser TOF 2108) and on with electron impact ionization (EI-TOF, 2602). The electrodes and short flight tube are attached to one of the receptacles of the wheel 1312 from FIG. 19, while the charged particle detector, i.e., the microchannel plate detector, can be either attached to the flight tube or independently removable via a cable attached to a vacuum fit-through out of the vacuum chamber. The excitation laser 2604 can be routed from the opposite side of the orientation laser so that the two laser beams are collinear but counter-propagating. The excitation laser 2604 can resonantly excite an electronic or vibronic or vibrational transition of the doped ion and non-thermally ejecting the ion out of the droplet beam. The ejected ions are then pushed into the flight tube 2606 for detection. Doped ions, on the other hand, have much larger masses than the ejected ions, and they cannot enter the small entrance of the flight tube in the low field of the electrodes on top of the flight tube. This method is also applicable for detecting neutral doped molecules, since by focusing the excitation laser, resonant or non-resonant ionization of the doped ions can be generated.

VI. Software

Software has been developed to run current working embodiments. Certain embodiments of the software perform the following functions.

1. Initial Start Up and Background—Instrument Monitoring

Diagnostics are continuously run to monitor the overall operating parameters to ensure all components are functional. This includes verifying operation of the roughing pumps. In addition, it is important to control multiple turbopumps. The cryostat is turned on and the temperature of the droplet source is monitored. Power is generated to the electron gun only when the necessary vacuum is achieved. Further, it is important to monitor the differential vacuums throughout the instrument and to determine that the electron gun is in safe operational mode. The laser is monitored to make sure that it is ready for firing. Finally, the imaging system is monitored for proper function and measuring background.

The software provides tuning, alignment, calibration and optimization modes to check for the formation of helium droplets, and the alignment of ion beams in the absence of helium.

2. Alignment and Tuning

The mass spectrometer and ion trap are tuned and calibrated for proper accumulation of protein ions. The optimization of the parameters for the selection and trapping of specific protein ions provides informative data for use with the ion bender and mixing chamber.

3. Calibration of the Image Collection System

Within the diffraction chamber, a staple crystalline sample can be moved into the diffraction zone to provide an accurate calibration of the diffraction image. This diffraction image calibration is used to determine the exact relation between the position on the image in millimeters or pixel numbers and the wave number in Angstrom$^{-1}$ in phase space.

Beam sizes are measured using a linear variable differential transformer (LVDT) device. The profile of each beam can be read from the corresponding detector, including a laser power meter and a Faraday cup. Spatial and temporal overlaps are measured among all three beams, including the electron beam, the laser beam, and the doped droplet beam using a phosphor screen that is coated with different types of phosphorous materials.

The LVDT device allows position measurement with a precision determined by the voltage readout. For example, with a model from Omega LD340-6.0, a distance of 500 micron generates a voltage reading of 1 V. As a result, if the voltage can be read with 1 mV precision, the position measurement can resolve 0.5 micrometer. If the LVDT is attached to a beam blocking object, as the beam blocking object traverses the path of the beam, the transmission would be changed based on the position of the beam blocking object. Typically the beam can be an electron beam, optical beam, ion beam, or any beam to be measured as long as there is a detector that can measure the intensity of the transmitted beam. The beam blocking object can be a simple plate with a sharp edge, and it needs to be opaque for optical beams, or conductive for charged particle beams. A motor can be used to drive the LVDT across the beam. If the measurement is in vacuum, a vacuum compatible motor is needed. The intensity of transmission is typically a sigmoid function, and differentiation of the sigmoid profile reveals the central position and width of the beam.

Figure 22:
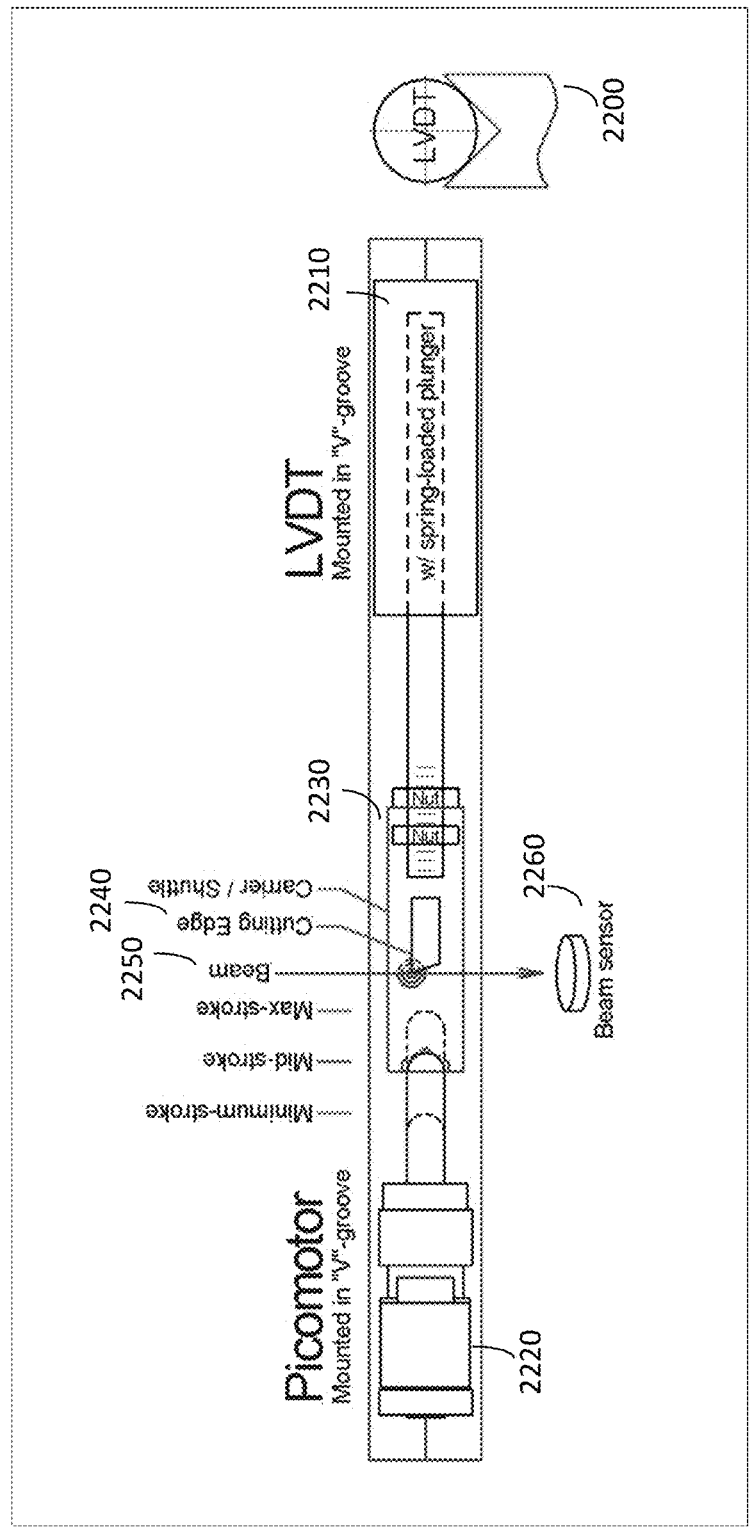
FIG. 22 is a schematic drawing illustrating one embodiment of a linear variable differential transformer.

FIG. 22 is a schematic drawing of one embodiment of an LVDT device, mounted in a V-groove 2200. It contains a LVDT 2210 (Omega, LD340-6.0), a picomotor 2220 (Newport 8302-UHV), and a shuttle 2230 carrying a cutting edge 2240, oriented so that it may cut two perpendicular beams. In FIG. 22 one beam 2250 is shown for illustration. As this beam is cut by the cutting edge the signal from a beam sensor 2260 is reduced. By continuing to advance the shuttle until the signal goes away the position and size of the beam can be determined. The device is contained in a vacuum chamber, and the electrical supply and readout of the transducer are routed out of the vacuum chamber via vacuum feedthroughs.

The LVDT device can be used for determining beam positions and effective beam sizes, as well as determining the focus point of an optical or electrical or magnetic lens. For example, if the corresponding voltage reading of the initial position of the transducer is recorded, the change of the voltage reading can be converted to the displacement of the transducer. To measure the relative positions of two beams for spatial overlap, the position of each can be determined and adjusted until they both correspond to the same central position. For determination of the focal point of a lens, the beam width at different locations along the beam path can be measured, and hence the location corresponding to the smallest beam size, i.e. the focal point, can be determined.

Figure 23:
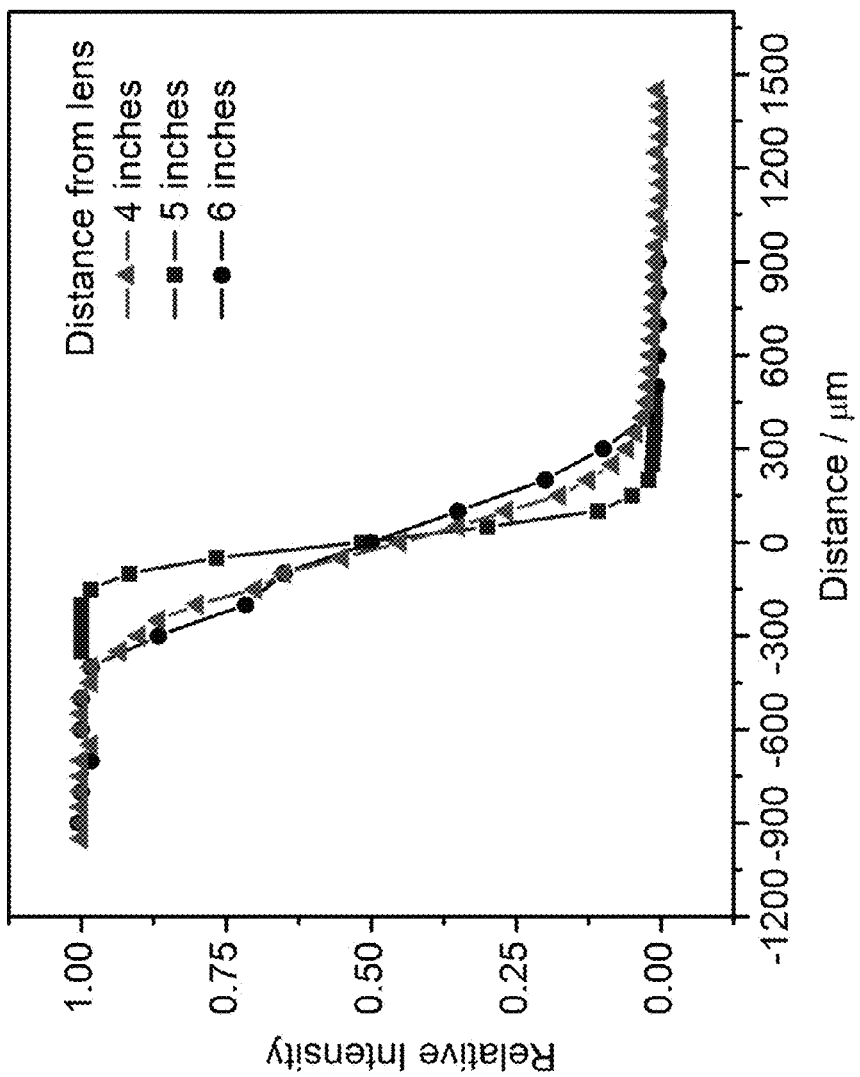
FIG. 23 provides transmission profiles of a focused laser beam measured at three different distances from a focusing lens using a linear variable differential transformer.

FIG. 23 shows the transmission profiles of a focused laser beam that were measured using an LVDT device. The light source was a helium-neon laser with an optical lens placed in the beam path. A light sensitive photodiode was used as the intensity detector of the laser beam. Three measurements at three different locations relative to the lens were performed. The two traces obtained at 4 inches and 6 inches from the lens were almost the same, implying that the focal point of the laser beam should be around 5 inches. The measurement at 5 inches resulted in the sharpest change in transmission, implying a small beam size consistent with the focal point of the optical lens.

Figure 24:
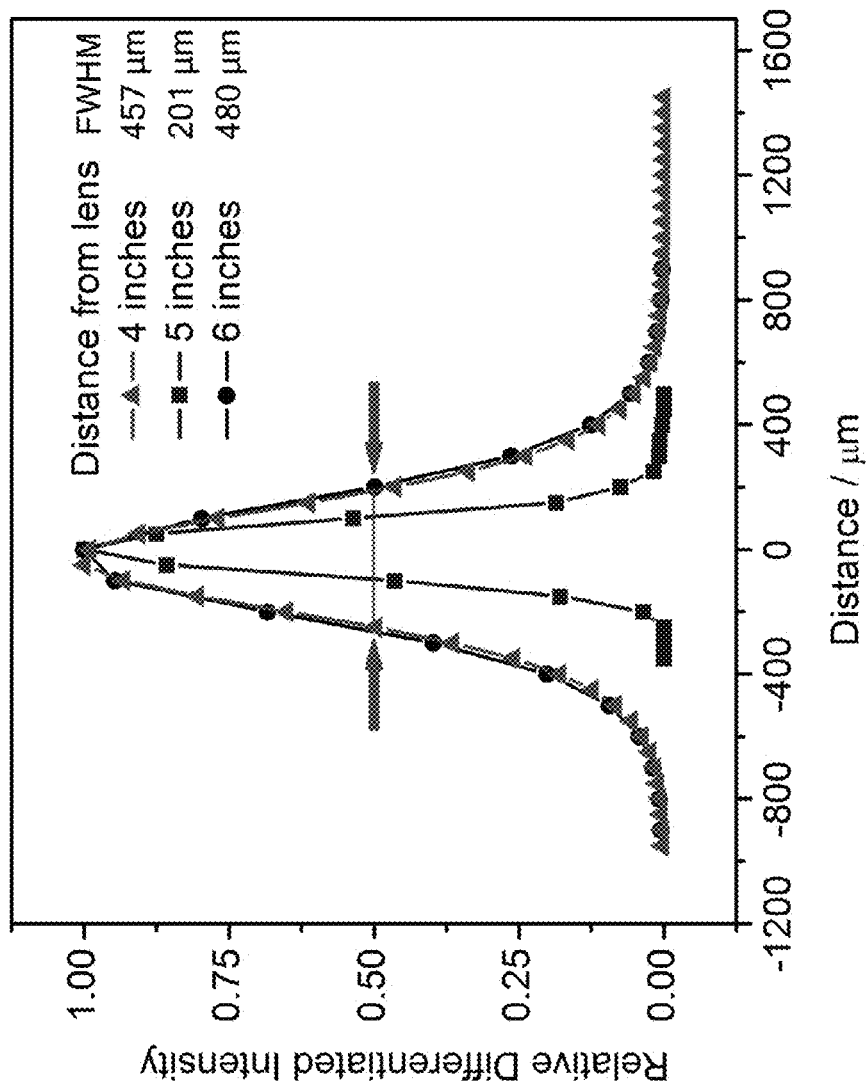
FIG. 24 is a differentiation form of the data provided by FIG. 23, which allows beam size to be determined at each measured distance.

To obtain the size of the beam, the transmission needed to be differentiated, and the results are shown in FIG. 24. The experimental data were fitted with polynomial functions, and the resulting fit was differentiated to show the rate of change of the transmission profile. From these profiles, beam sizes when the LVDT was placed 4 and 6 inches away from the lens were determined as 457 and 480 microns respectively, and 201 microns at 5 inches.

4. Data Collection Sequence

Data collection is divided into two major tasks:
 a) controlling the orientation of the macromolecule with respect to the electron beam by the polarization of the laser; and
 b) collecting and combining diffraction images of the macromolecules to achieve the selected atomic resolution.

The orientation of the macromolecule is determined by 1) the angle between the laser and the droplet beam, and 2) the polarization of the laser beam (the reference frame is arbitrary and determined by the properties of the macromolecule under study)

The angle between the laser and the droplet beam may be altered by changing the path of the laser using mirrors in the plane perpendicular to the electron beam. A single angle can provide a complete data set, but changing the orientation provides redundancy that improves the quality of structures determined.

5. Optional Laser/Droplet Beam Angle Loop

This loop is used if the instrument is designed to allow any angle from 90° to 180°, i.e. from orthogonal to co-linear, to be selected between the orientation laser and the electron beam.

6. Macromolecular Orientation Loop

The laser polarizer angle is moved for image collection from a chosen diffraction projection. The polarizer angle provides important information for turning 2-D electron diffraction images into a three-dimensional array used to extract the electron density maps.

7. Image Collection Loop

This loop controls the following sequence of ten sequential events to collect a single image. The frequency of running through the loop is controlled by how fast the orientation laser can be repeatedly pulsed. With current technology, this rate is 10-20 Hertz.

a) Under computer control, biological molecule ions from an electrospray interface with a quadrupole single stage mass analyzer are directed into the first ion trap. This process uses standard procedures to control the functioning of a mass spectrometer to select ions of a particular mass-to-charge ratio.

b) A packet of biological molecule ions is accumulated in the ion trap, using standard mass spectrometry methods for controlling the quadrupole ion trap. (It is possible to combine both the quadrupole mass analyzer and the ion trap into a single functional unit that can accomplish both purposes. The current configuration is advantageous because it is more flexible for developmental purposes.)

c) The helium droplet valve opens at the appropriate time so that the slow moving helium droplets at 200-400 m/s can arrive in the second ion trap, the cone trap in this case, for effective mixing with the arriving ions from the ESI source.

d) The biological molecule ion packet is expelled into the ion bender. The computer controls the direct current voltages driving an ion bender to focus the protein ion beam along the main axis of the instrument.

e) The entrance gate of the cone trap opens for 100-200 microseconds to cause biological molecule ions to bounce back and forth along the direction of the helium droplets.

f) The exit gate of the cone trap opens for 400 microseconds after the filling of the cone trap and after arrival of the helium droplets. As the helium-embedded biological molecule ions emerge from the cone trap, apply an accelerating voltage to compress and focus the ion packet of doped ions.

In another embodiment illustrated in FIG. 25, steps c)-f) can be replaced by c1)-f1):

c1) The helium droplet valve opens at the appropriate time so that the slow moving helium droplets at 200-400 m/s can encounter the biological molecule ion released from the ion source and arrive in the size reducer component.

d1) The biological molecule ion packet is expelled into the path of the droplet beam and is slowed down and stopped by an electrode facing the ion source.

e1) The doped droplets continue to move into the size reducer component, accelerated by the entrance electrode of the size reducer. Low pressure helium controlled by a fine needle valve collides with the droplets to remove some of the surrounding helium atoms.

f1) The exit of the reducer component further accelerates to compress and focus the packet of doped ions.

g) Optionally, the biological molecule ions may be further focused in the diffraction/orientation chamber using a digital ion trap. In this trap, the computer generates square wave pulses to slow the movement of the ions in a region of 0.1 to 0.2 $mm^3$.

h) The voltage on the electrode right upstream from the diffraction region or the voltage of the digital ion trap is also used to provide an initial orientation of the biological molecule ions via interactions with the dipole moment. This feature assists in orienting the biological molecule along its primary axis just prior to the firing of the orientation laser.

i) The orientation laser and the electron gun are fired at nearly the same time for diffraction. If the electron gun and the droplet beam are synchronized at 20 Hz, while the orientation laser is only fired every other short, i.e. at 10 Hz, automatic toggle of the image on the camera performs direct subtraction of the randomly oriented sample image from the oriented image. This resulting image contains only coherent molecular scattering of the oriented ions, without interference of the surrounding helium atoms of the droplet or background from the atomic scattering of the constituent atoms of the molecular ion. The latter has always been a strong background in standard electron diffraction.

j) The raw image is saved with operating parameters. Initial quality control checking of the image is performed to ensure the instrument is operating as expected.

This is the end of the Image Collection Loop.

8. Image Processing for Each Projection

Each packet of biological molecule ions will produce a 2D image from a particular orientation controlled by the orientation laser. Because the signal intensity for higher resolution data may be particularly low in intensity (involving single electron counting), multiple images from the same orientation are averaged together.

The images can be corrected for distortions and nonlinearities of the detector, using calibration data from known crystal standards that can be positioned in the detector.

The completion of the data collection and image processing sections provides a series of 180 two-dimensional images, each corresponding to a 1 degree rotation of the laser polarization field. The images are symmetric around the laser axis and thus it is not necessary to collect all 360°.

This ends the Macromolecular Orientation Loop and ends Optional Laser/Electron Beam Angle Loop.

9. Phase Extraction and Reconstruction of Electron Density Map

A. Constructing the Reciprocal Space Data Cube

The first step is to transfer the information from the 180 images into a 3-dimensional cube of data elements. The main axis of the laser passes through one of the faces through the center of the cube. Each image is considered as a plane rotated around the main axis defined by the laser, with the plane rotated by the degree by which the laser polarizer has been turned during data collection.

The intensities recorded on each image are distributed among the nearest neighboring data elements in the 3D cube.

The data in the 3D cube contain only the squares of the amplitudes of the scattering factors. If the phases were also known, a simple 3D Fourier transform would convert the data in the 3D cube into a map containing the electron density.

B. Phase Extraction by Oversampling

The phase information is extracted by iteration by first providing a set of randomly chosen phases. This set of chosen phases is combined with the experimentally observed amplitudes from the data cube to calculate an initial electron density map. (This part of the code is shown below).

C. Iterative Phase Determination Loop

1) The electron density map is adjusted so that all the density outside of the biological molecule is zero (since the biological molecule is surrounded by vacuum) and that the electron density inside of the biological molecule is positive and a real number.

2) The adjusted electron density map is then subjected to a Fourier transform to calculate a new set of phases in reciprocal space.

3) These phases are combined with the experimentally determined amplitudes in the 3D cube to then recalculate the electron density map by the inverse Fourier transform.

4) Repeat Step 1 until the final electron density map converges (which typically takes 200 to 4,000 cycles).

This ends the Iterative Phase Determination Loop.

At this point, the final result is an electron density map that is used with many traditional x-ray diffraction programs used for structural refinement to model protein structures into the observed electron density.

The following is code from Matlab that solves the 3D structure (Matlab script that calls Fienup phase extraction function).

```
clear all;
close all;
Dim = 100;
ImageObject=imread('benchmark.bmp', 'bmp');
ImageObject = ImageObject(:, :, 1);
RandomInput = zeros(Dim, Dim, Dim);
for ii = 1:Dim
    RandomInput(:, :, ii) = ImageObject;
end
InitialObject = zeros(2*Dim, 2*Dim, 2*Dim);
InitialObject(1:Dim, 1:Dim, 1:Dim) = RandomInput;
Support1 = double(InitialObject>0);
DiffractionPattern = abs(fftn(InitialObject)).^2;
% [OutPut, ErrorEvolution] = FienupIO3D(DiffractionPattern, Support1);
% imagesc(OutPut(:, :, 1));colorbar
figure
imagesc(InitialObject(:, :, 1));colorbar
```

```
function [OutPut, ErrorEvolution] = FienupIO3D(DiffractionPattern, Support)
% Fan Zhang
% Sept. 2009
% 3D phase retrieval based on Fienup Input Output approach.
[DimX, DimY, DimZ] = size(DiffractionPattern);
FourierAmplitude = sqrt(DiffractionPattern);
InitialInput = rand(size(DiffractionPattern));
OldError = 1;
DeltaError = 0.95;
ErrorEvolution = zeros(200, 1);
ErrorLimit = 1e-10;
beta = 0.9;
NN = 1;
NN_max = 10000;
while and(NN < NN_max, DeltaError > ErrorLimit)
    InitialPhase = fftn(InitialInput)./abs(fftn(InitialInput));
% ScratchObject = real(ifftn(InitialPhase.*FourierAmplitude));
    ScratchObject = real(ifftn(InitialPhase.*FourierAmplitude));
    ScratchSupport = double(real(ScratchObject)>0).*Support;
    Object1 = ScratchObject.*ScratchSupport;
    Object2 = (InitialInput - beta*ScratchObject).*(1-ScratchSupport);
    InitialInput = Object1 + Object2;
    NewError = sum(sum(sum(abs(Object2))))/sum(sum(sum(abs(Object1))));
    DeltaError = abs(NewError - OldError)
    OldError = NewError;
    NN = NN + 1;
    ErrorEvolution(NN) = NewError;
    imagesc(abs(InitialInput(:, :, 1))); drawnow
end
OutPut = abs(InitialInput);
Return.
```

VII. Examples

The following examples illustrate features of particular working embodiments. A person of ordinary skill in the art will appreciate that the scope of the present invention is not limited to the features exemplified by these working examples.

Example 1

FIG. 2 is an electrospray spectrum of the $12^{th}$ charge state of a mutant human superoxide dismutase (SOD1) overexpressed in transgenic mice that causes the mice to develop ALS. The isotope-resolved spectrum of FIG. 2 was collected with a ThermoFisher FTICR within 2 minutes of a 100-μg tissue punch taken from the mouse spinal cord. This result illustrates how an abundant protein can be "purified" directly from tissues in a mass spectrometer free of residual sodium or water adducts, and still retain its two metal ligands (copper and zinc). Since both copper and zinc are positively charged and positioned close to each other, denaturation causes the loss of these metals. These spectra were collected by averaging packets of approximately $10^5$ SOD molecules with each injection taking approximately 50 milliseconds. These data establish that protein packets of high purity can be generated and even isolated directly from tissues and that the disclosed method works with low concentrations of proteins found in vivo.

The data of FIG. 2 contains two forms of SOD (differing only by the absence of zinc in the left peak) as isolated from brain, and illustrates that even a low-resolution quadrupole mass selector can readily separate proteins differing by a single heavy atom for image collection. A significant variable in crystallography is estimating the unknown and variable extent of occupancy for ligand binding. The mass selector can choose only those proteins with ligand bound for further examination to make occupancy an experimentally controlled parameter. Accordingly, structures may be determined from only those macromolecules selected to retain ligands.

Example 2

Figure 20:
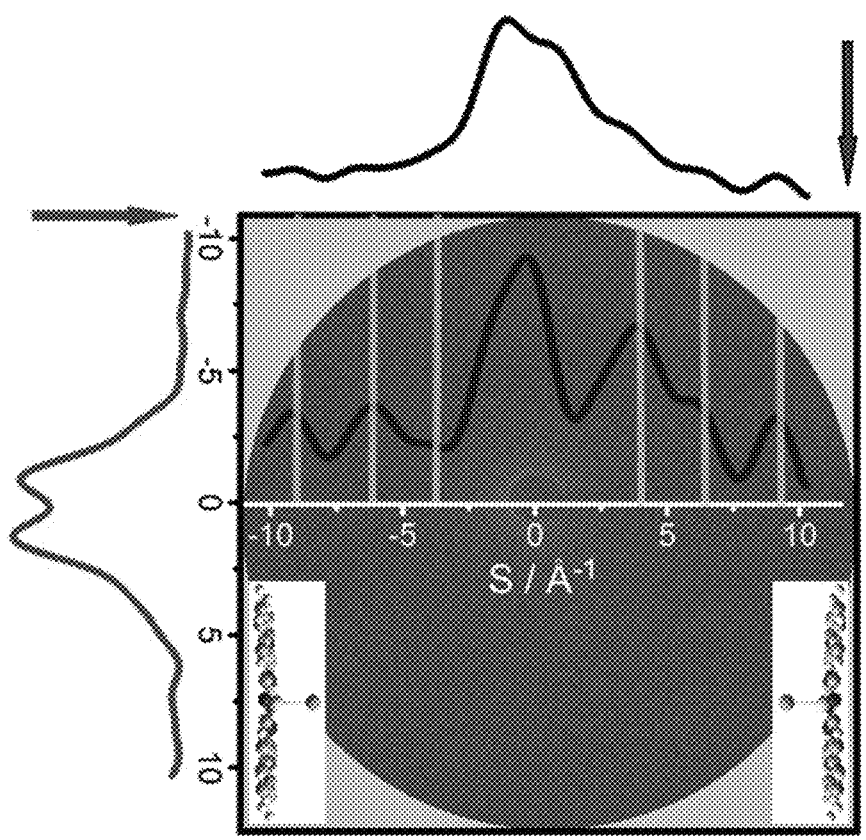
FIG. 20 is an electron diffraction image of laser aligned PcGaCl embedded in superfluid helium droplets. The binning results along both axes are shown outside the image, while the difference is shown in the image box. The vertical lines show the theoretical maxima assuming a bond length of 2.2 Å for GaCl. The asymmetry is due to the filament of the electron gun.

PcGaCl has a smaller polarizability than a protein and thus is more challenging for laser-induced alignment. As shown in FIG. 20, laser-induced alignment of a helium-embedded small molecule has been achieved with disclosed embodiments of the existing apparatus, without the benefit of image-enhancing technologies. The circularly polarized alignment laser propagates along the horizontal direction, resulting in the Ga—Cl pair aligned along the same direction. The diffraction lines thus are vertically oriented. The image's signal-to-noise ratio (black patch of the central box) is still low, but binning along the two axes reveals definitive differences in the diffraction profile. The horizontal integration (shown along the left edge of FIG. 20) contains the superposition of atomic and helium droplet diffraction profiles, while the vertical integration (shown along the top edge of FIG. 20) contains the additional contribution from the interference of Ga and Cl. The peak positions in the difference curve agree with the expected diatomic interference of GaCl with a bond length of 2.2 Å (vertical lines on image). Within the range of detectable momentum transfer, the resolution is 0.8 Å. The asymmetry of the data is due to the optical image from light leaking through the filament of the electron gun. This result establishes the "proof-of-principle" of coherent electron diffraction from laser-aligned molecules embedded in helium droplets. Further improvements in the ion optics and image detection described in the work plan will enable high-resolution images to be achieved.

Example 3

Figure 27:
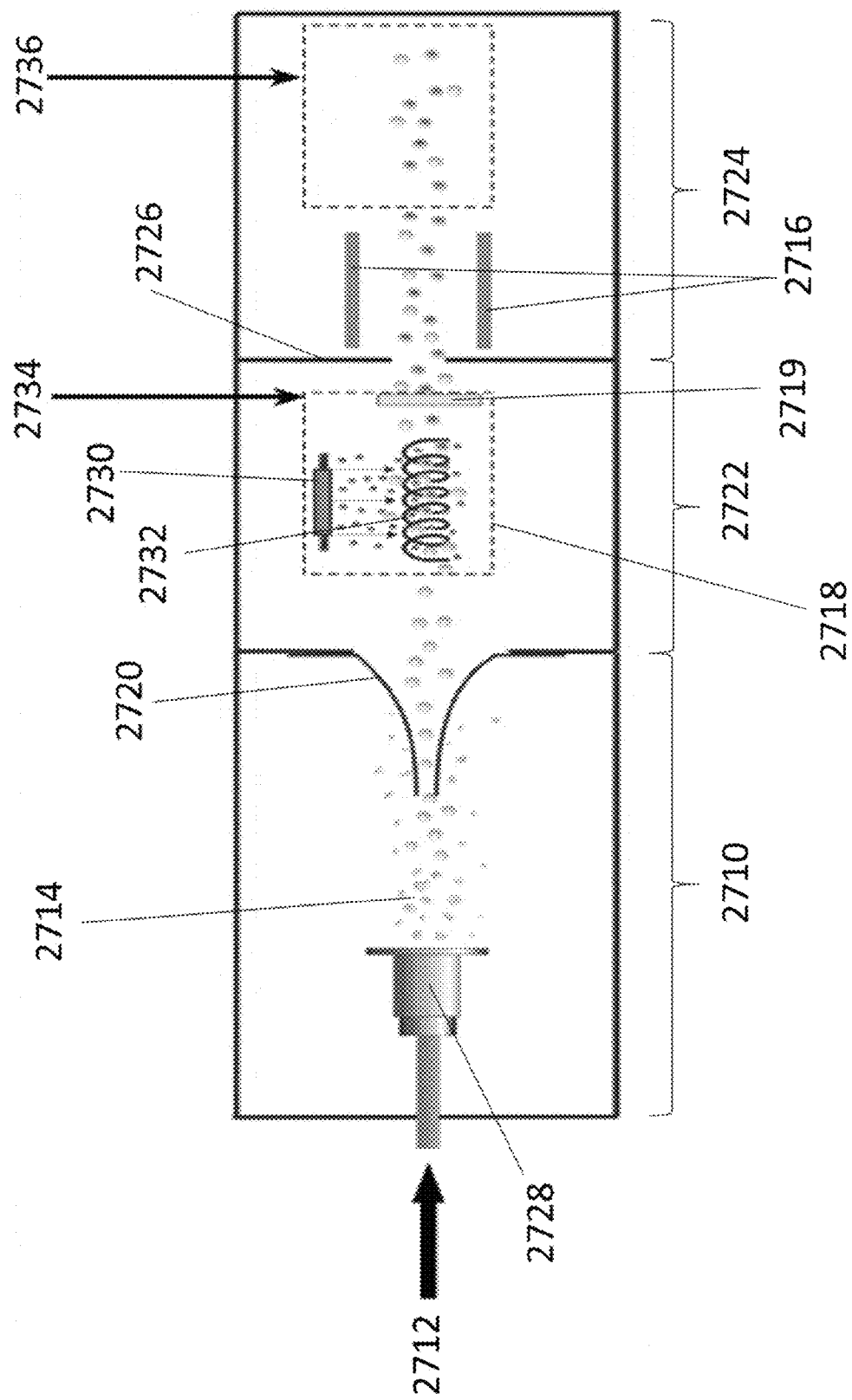
FIG. 27 is a schematic drawing illustrating certain components of a disclosed embodiment for measuring the doping efficiency of ions from a thermionic ion source.

To investigate the doping efficiency of cations in helium droplets, an experiment was designed using singly charged cesium cations ($Cs^+$). FIG. 27 provides a schematic diagram of the experiment. Superfluid helium droplets were generated in the source chamber 2710 from a helium gas source 2712. The droplet beam 2714 passed through the ion source region and arrived ultimately at a copper target detector 2719. The droplet source chamber 2710 and the ion source and analysis chamber 2722 and 2724 were separated by a skimmer 2720. The two regions 2722 and 2724 were separated by a copper plate 2726 with a 1 cm central hole. The droplet source chamber 2710 was pumped by two diffusion pumps (Varian VHS-6 and Edwards Diffstack 160 mm, not shown) and was usually at $4\times10^{-7}/4\times10^{-6}$ torr when the pulsed valve was off/on. The ion source and analysis regions (2722 and 2724) were pumped by a turbo molecular pump (Varian V551, not shown) and was typically at $7\times10^{-7}/4\times10^{-6}$ torr when the pulsed valve was off/on.

A pulsed valve 2728 (Parker Hannifin Corp, Series 99) was used to produce superfluid helium droplets by supersonic expansion of ultrapure (99.999%) helium at about 30-50 bar into vacuum. The pulsed valve 2728 had a homemade nozzle with a diameter of 500 μm. It operated at 10 Hz with a duration of 130-145 μs powered by its own driver (Parker Hannifin Corp, IOTA One). The nozzle was cooled by a closed-cycle helium cryocooler (APF cryogenics, HC-4 MK1, not shown), and it could be set at any temperature above 13 K. The helium droplet beam 2714 was further collimated by a 5 cm long skimmer 2720 of 2 mm in diameter (Beam Dynamics) located 12 cm downstream from the nozzle.

Cesium ions were produced by heating a tungsten filament 2730 coated with a zeolite paste as detailed by Draves et al., J. Chem. Phys., (1990), 93:4589. The filament was a tungsten coil of 3.0 cm in length and 2.0 mm in diameter, and the wire itself was 0.25 mm in diameter. Under normal working conditions, a current of about 2.8 μA was passed through the filament, and the total emission current was 2.8 μA. The ion collector 2732 was a copper grid of 2 cm long and 1 cm in diameter. The grid 2732 was coaxial with the droplet beam 2714 and was biased negative relative to the filament, thereby facilitating the oscillation of cesium ions through the space inside the grid at a constant and defined kinetic energy. The grid was connected to an operational amplifier and a megaOhm resistor (not shown), which converted the ion current into a voltage signal. This current was treated as representative of the total number of available ions for doping, although the true number of ions inside the grid was unknown. Both the grid 2732 and the filament 2730 could be independently biased, and the current on the grid increased with the bias voltage on the grid. Typically when the grid 2732 was at −100 V and the filament 2730 was at 10 V, the voltage signal was about 1.5 V, corresponding to an ion count of $10^{13}$ ions/second on the grid.

The copper target detector 2919 measuring 4 mm×10 mm was attached to an operational amplifier and a gigaOhm resistor (not shown), converting a single charge into a voltage pulse. The copper target 2719 was only sensitive to charged species; hence neutral undoped droplets generated no detectable signal. The ion source and copper target region 2718, comprising the ion source 2730, the grid 2732 and the detector 2719, could be placed in two different positions, shown as positions 2734 and 2736 in the figure, so the group velocity of the droplet beam could be determined by monitoring the different arrival times of the doped droplets on the target. In the analysis region 2724, a set of electrodes 2716 could be used to deflect the charged particles away from the detector, with the intention of resolving the kinetic energy of the charged species. When used for this purpose, the copper target 2719 was placed at position 2736 while the ion source 2730 and 2732 remained at position 2734.

Example 4

Doping Helium Droplets with Cesium Ions

Figure 28:
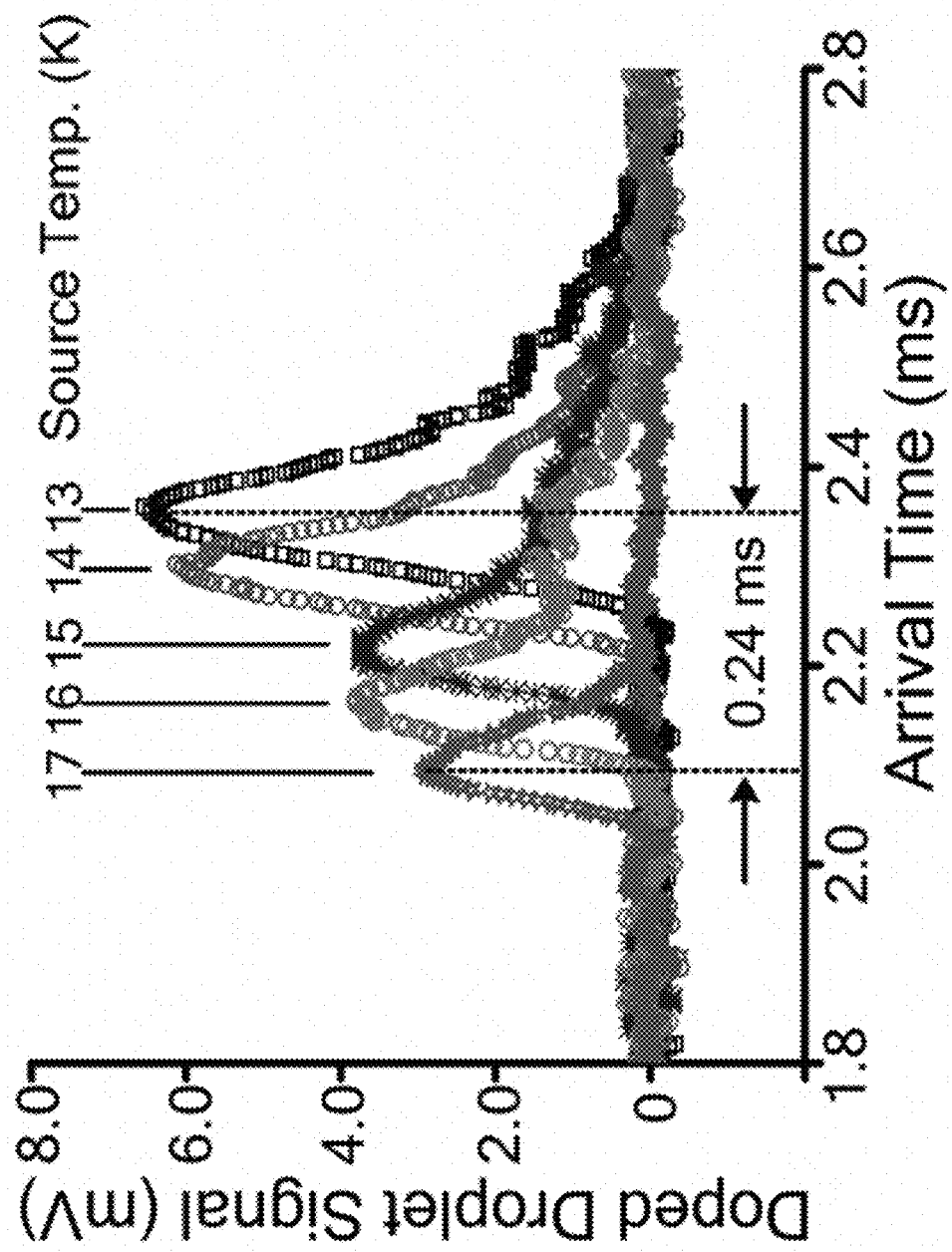
FIG. 28 is a graph of cation doped droplet signal versus arrival time, illustrating the arrival times of droplets at various nozzle temperatures.

FIG. 28 shows the time profile of the detected cesium doped droplet signal under different nozzle temperatures, using the apparatus described in Example 3. Both the magnitude and timing of the ion signal depend on the temperature of the droplet source. FIG. 28 illustrates that with increasing nozzle temperature, and the ion detector in position 1, the ion signal decreased and shifted to an earlier time. Shoulder peaks visible under all different nozzle temperatures were results of the rebound of the pulsed valve. From 13.2 K to 17 K, the arrival time of the ion signal shifts by 0.24 ms and the total signal decreases by over 50%.

Without any acceleration field along the flight path, the arrival time of the doped droplets was determined by the group velocity of the neutral droplet beam. Although the response time of the gigaOhm resister was limited, with sufficient distance between the two measuring points (positions 2734 and 2736 in FIG. 27), the onset of the ion signal could still be used to measure the velocity of the droplet beam. In FIG. 27, position 2734 was 37 cm away from the pulsed valve 2728, and position 2736 was 74 cm away from the pulsed valve. From the difference in the arrival time between the two positions, the droplet speed was determined to be 388 m/s at 14 K and 422 m/s at 17 K. These results were in general agreement with the theoretical speed of an ideal helium gas from a supersonic expansion, which should be 380 m/s at 14 K and 419 m/s at 17 K.

Example 5

Determination of the Effects of Fringe Fields and Space Charges

Figure 29:
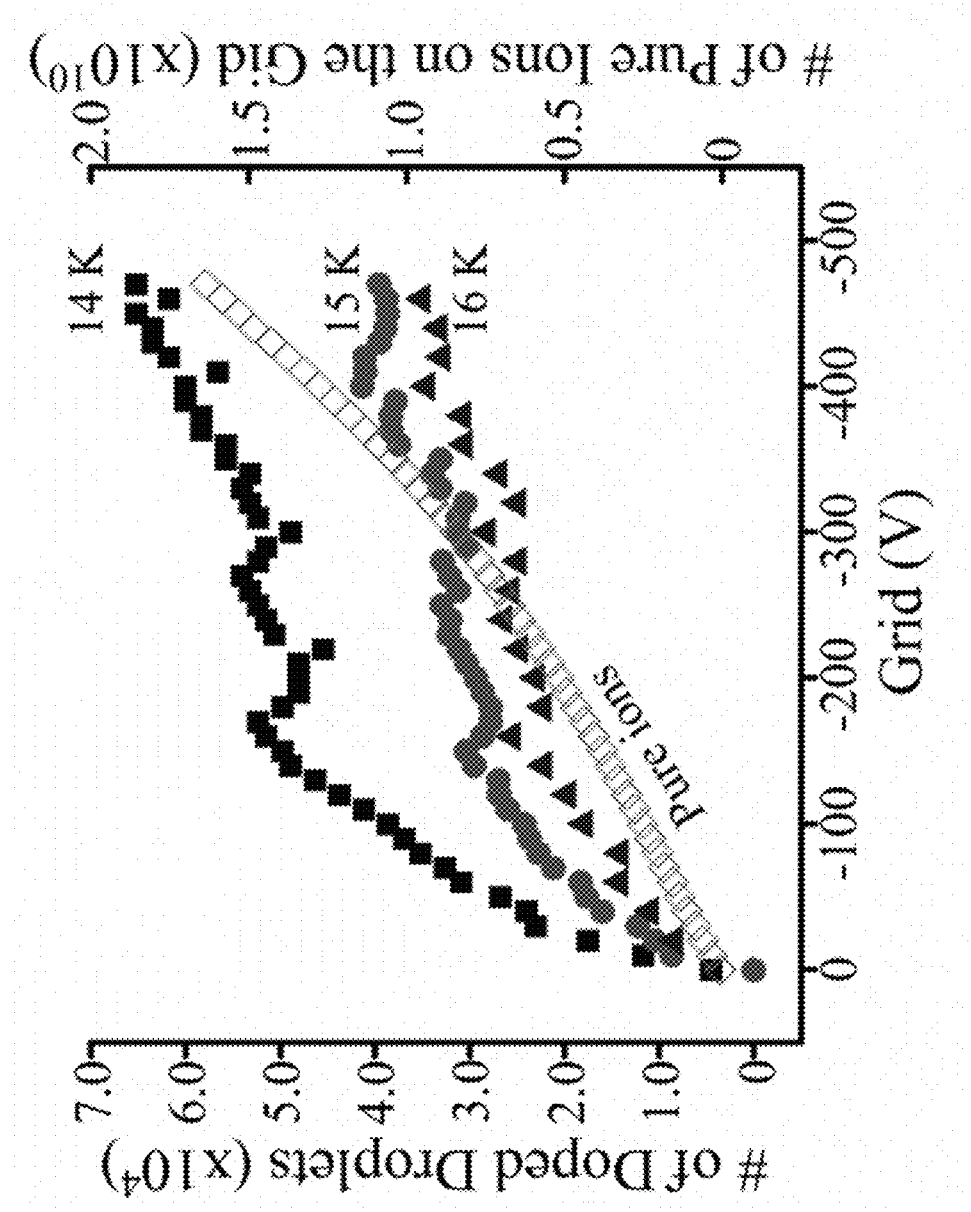
FIG. 29 is a graph showing both the number of doped droplets, and the number of pure ions on the grid, versus grid voltage, illustrating the dependence of both the number of doped droplets (left axis, filled symbols) and the number of ions hitting the grid (right axis, open squares) on the grid voltage at different temperatures of the droplet source.

To quantitatively characterize the doping efficiency, FIG. 29 shows the total number of doped ions and the total number of ions hitting the grid at different grid voltages. While the number of bare ions hitting the grid increased with the grid voltage following a power law, the number of doped droplets also increased but with a clear "bend" when the grid voltage reached −150 V. FIG. 29 also shows that with increasing source temperature, the number of doped droplets also dropped. At 16 K when the grid voltage was −100 V, the number of doped droplets was less than half of that at 14 K.

The bias on the grid in the ion source affected not only the number and movement of bare ions, but also those of doped ions, both as a trapping field and in terms of fringe fields at the exit of the grid downstream from the doping region. The group velocity of the pure droplet beam was 388 m/s at a source temperature of 14 K, and at a grid voltage of −180 V, a doped droplet had to consist of at least $3.2 \times 10^4$ helium atoms to have enough kinetic energy to escape from the negative trapping field of the grid. Downstream, some escaped doped droplets would be affected by the fringe field of the grid thereby veering too far off-axis along the path to the target. Using Lorentz-EM (Integrated Engineering Software, Winnipeg, Manitoba, Canada), a software package specially designed for magnetic analysis and for analysis of charged particle trajectories in the presence of electric and magnetic fields, this fringe effect was simulated, and a cutoff size of about $10^5$ helium atoms per droplet was obtained. Below this value a doped ion would fail to arrive at the target. Experimentally, the actual cutoff size was probably an order of magnitude even bigger, at about $10^6$ atoms/droplet, as will be discussed in the following. As the grid voltage increased, the cutoff size also increased. Additionally, FIG. 29 also appears to show that the number of bare ions traveling into the grid also increased. The increase in the number of doped ions, however, slowed down at the "bend" when the grid voltage was more than −150 V.

One possible factor that can damp the growth of the doped ion signal at higher grid bias voltages is the space charge limit. In FIG. 29, the number of ions hitting the grid is on the order of $10^{10}$, and given the fact that the volume inside the grid was a few cubic centimeters, this value is way above the space charge limit. The actual number of ions inside the grid should then be much smaller, on the order of $10^7$. Thus once the space charge limit was reached, further increase in the grid bias would only have the limited effect of increasing the effective volume for ion retention, and the increase in the number of bare ions for doping would be at a much lower rate. On the other hand, the cutoff size would increase with increasing bias, preventing small doped ions from reaching the detector. The change in the number of doped ions was then determined by the balanced effect of the cutoff size and the doping volume. The "bend" in FIG. 3 could be the point where the space charge limit was reached, and the slow rise after −150 V was the predominant effect of the increasing doping volume with increasing grid bias.

With reference to the "bend" in the observed ion counts of FIG. 3, if it is assumed that the total number of bare ions in the doping region was limited by the space charge at a grid bias of −150 V, the absolute doping efficiency should be on the order of 5‰ at a source temperature of 14 K. On the other hand, if the "bend" was not representative of the space charge limit, then the actual doping efficiency should be higher.

Example 6

Droplet Size Distribution—Deflector Test

Figure 30:
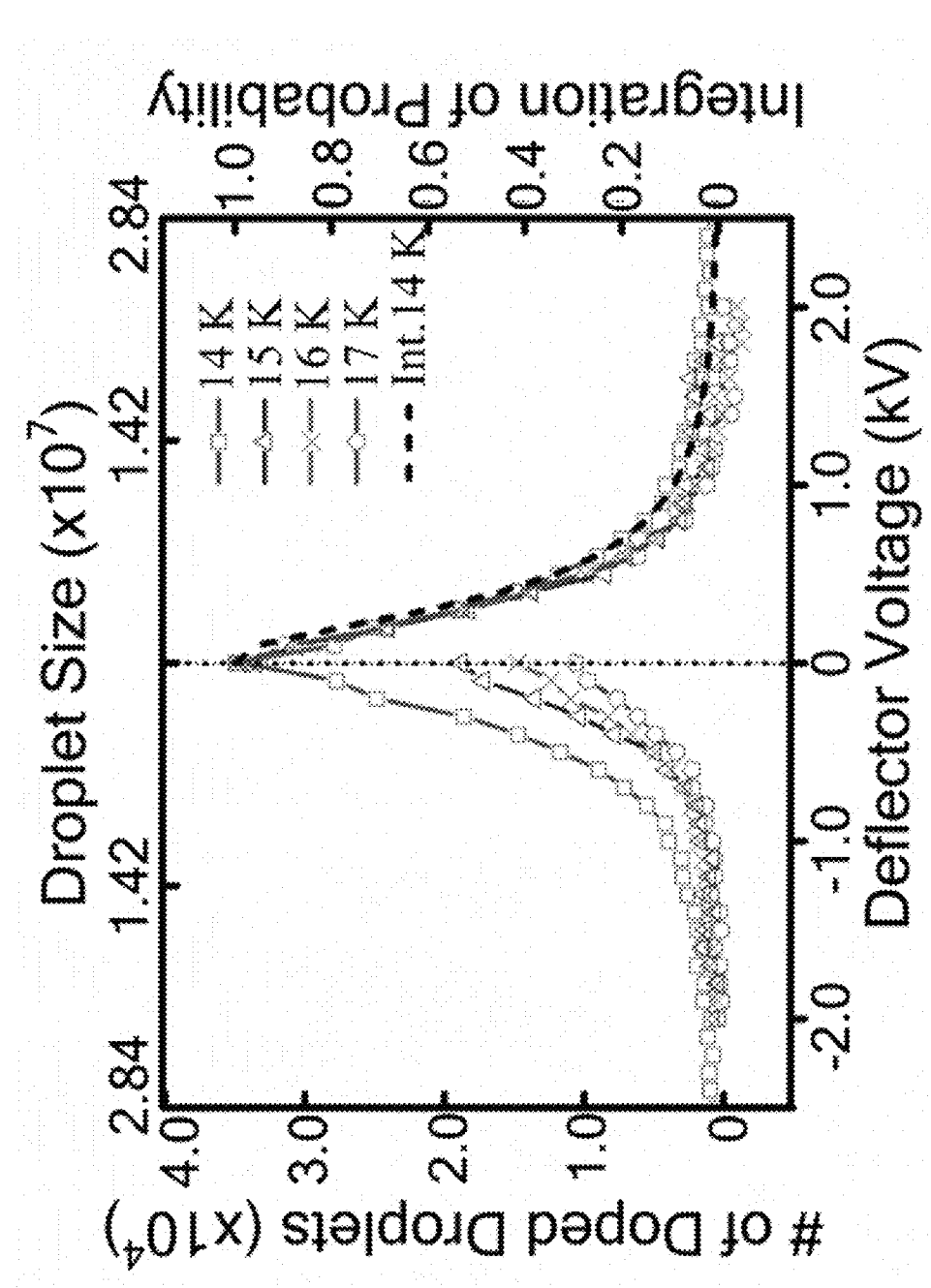
FIG. 30 is a graph showing both the number of doped droplets, and the integration of probability, versus both deflector voltage and droplet size, illustrating the absolute number of doped droplets arriving at the target under different deflection voltages (left panel), and the normalized ion signal.

To determine the size distribution of the doped droplets, a set of deflectors to steer the doped droplet beam away from the detector was initially used. As the voltage on the deflector increased, small doped droplets were driven away from the detector, thus a correlation between the detected doped droplets and a lower size limit was established at each deflection voltage. In FIG. 27, the deflector electrodes 2716 were 40 mm long and were separated by 40 mm. These electrodes were positioned 38 mm downstream from the ion source, and the detector (4 mm along the deflection direction) was located 60 mm downstream from the deflectors. During the experiment, one of the deflector electrodes was grounded, while the other was biased from −2200 V to 2200 V. The left axis of FIG. 30 shows the number of doped droplets arriving at the target under different deflection voltages (bottom axis), and the top axis shows the corresponding lower mass limit for the detected droplets. At −300 V, the signal dropped to 54% of that without the deflection voltage. The corresponding lower mass limit for the doped droplets arriving at the detector was $4.3 \times 10^6$ helium/droplet.

The source temperature of the pulsed valve determines the average size of the droplet beam, which in turn affects the doping efficiency. After doping, it was anticipated that perhaps the size distribution of the resulting doped droplet should also reflect this difference. To emphasize the size distribution at different source temperatures, the right-hand axis of FIG. 30 illustrates the normalized ion signal determined by setting the maximum ion intensity under a fixed nozzle temperature to unity. Surprisingly, all traces overlap. It was therefore concluded that within the temperature range of 14 and 17 K, the doped droplets had a similar size distribution, independent of the initial nozzle temperature.

Figure 31:
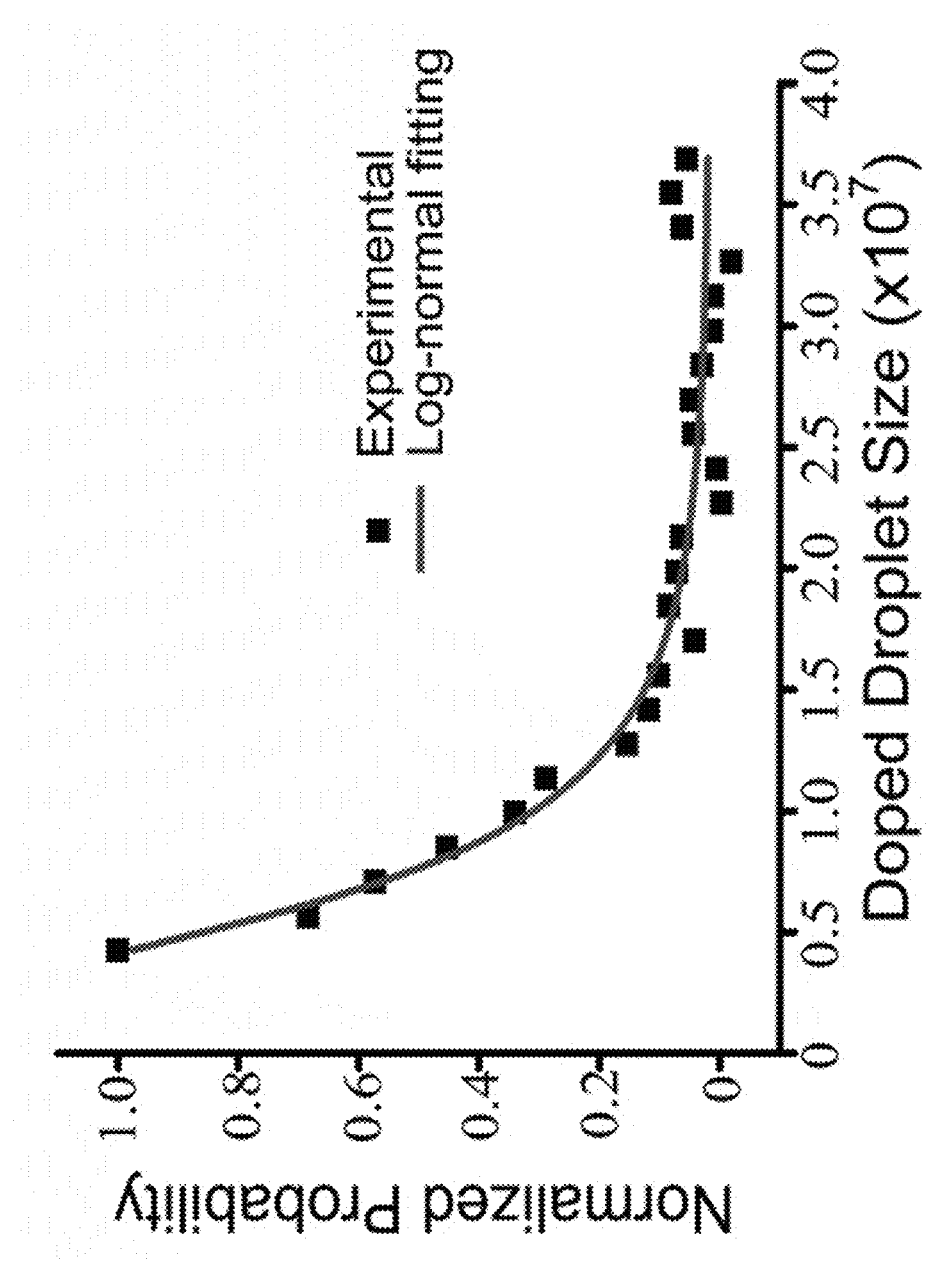
FIG. 31 is a graph of normalized probability versus doped droplet size illustrating the size distribution of doped droplets at a source temperature of 14 K.

It has previously been suggested that the size distribution from a continuous superfluid helium droplet source can be modelled using a log-normal function when the nozzle temperature is higher than 14 K, $$P_N(N) = \left(N\sigma\sqrt{2\pi}\right)^{-1} \exp\left[\frac{-(\ln N - \mu)^2}{2\sigma^2}\right], \quad (1)$$

where $P_N(N)$ is the probability of a droplet consisting of N helium atoms, and the parameters $\sigma$ and $\mu$ are the standard deviation and the mean of ln N. The size distribution of the doped droplets could be obtained by differentiating the number of doped droplets arriving at the detector by the corresponding minimum droplet size (the top axis of FIG. 30). In FIG. 31, black squares represent the resulting differentiation from the experimental data at 14 K (FIG. 30), and the continuous trace is a log-normal fit to the experimental data. The mean size from this fitting was $7 \times 10^6$ helium/droplet. Similar treatments of data from other source temperatures also resulted in similar size distributions and mean sizes. The resulting values of $\sigma$ and $\mu$ were about 0.77 and 15.45. These values were then used to calculate the number of doped droplets at each deflection voltage by integrating Eq. 1 from the lower mass limit determined from the experimental geometry to infinity, and the result is shown by the dashed line of FIG. 30 labelled "Int. 14 K". This trace overlapped with the experimental data. Although it was known that in the range of the current source temperatures (≥14 K), neutral helium droplets followed a log-normal function, the doping process did not appear to alter this size distribution substantially. However, the consistency in size and distribution within the temperature range also implied that the size distribution of the doped droplets was insensitive to the initial size distribution of the neutral droplet beam. This could be due to the small limited temperature range of the cryostat, and the fact that only the tail part of a log-normal distribution was fitted to the curve. Previously, a similar conclusion was obtained within the temperature range of 14 K to 18 K.

Example 7

Droplet Size Distribution—Energy Filter Experiment

Another possible approach to determine the size distribution of doped droplets is to introduce an energy filter using a biased mesh. If the doped droplets move at a constant group velocity, different sizes will have different kinetic energies, and only ions with sufficient kinetic energies can pass through the biased retardation electrode. For this purpose, the deflector electrodes were replaced with a planar electrode that had a circular hole of 38 mm in diameter. The hole was covered with a fine mesh of 50×50 mesh plain and 0.025 mm in wire diameter. To further shield the copper target from the field of the retardation electrode, another coarse mesh of 16×16 mesh plain and 0.25 mm in wire diameter was placed 2 mm in front of the copper target. The planar electrode and detector were positioned 142 cm downstream from the ion source.

Figure 32:
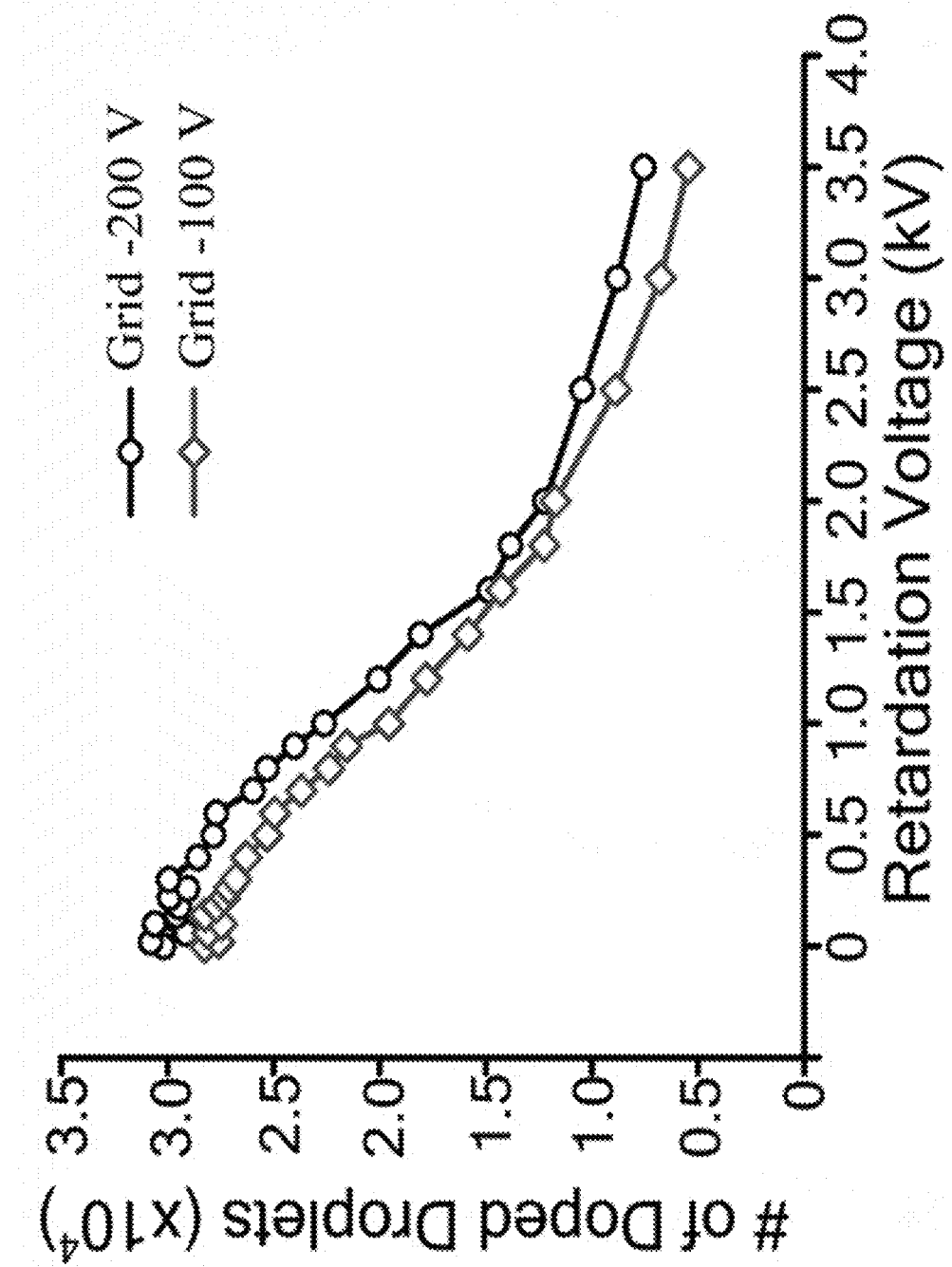
FIG. 32 is a graph of number of doped droplets versus retardation voltage illustrating the number of doped droplets that pass through a retardation electrode.

FIG. 32 shows the variation of the ion signal as a function of the voltage on the retardation electrode when the source temperature was 14.5 K. The experiment was performed under two different voltages on the grid of the ion source, −200 V and −100 V, and in both cases, the trend was the same. The uncertainty of each data point was about 10%, so the "bend" in the experimental data at a retardation voltage of 1500 V when the grid voltage was −200 V was most likely due to a variation in the experimental condition. From FIG. 32, even when the retardation voltage reaches 3500 V, there were still more than 28% of the doped droplets reaching the target, and the corresponding droplet size is $1.1 \times 10^6$ helium/droplet.

Figure 33:
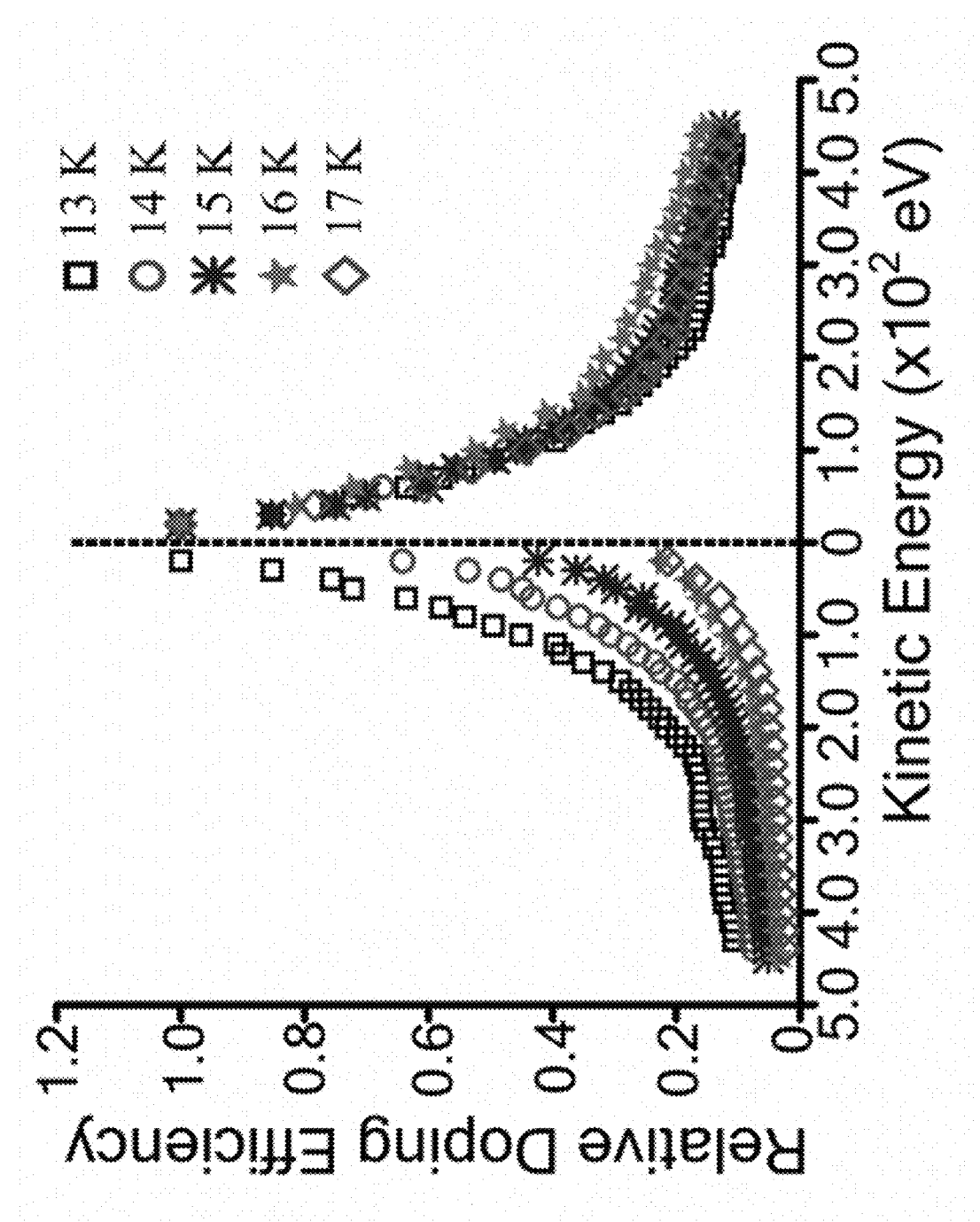
FIG. 33 is a graph of relative doping efficiency versus kinetic energy illustrating the relative doping efficiency at different kinetic energies and source temperatures.

A mean size of doped droplets was obtained from FIG. 33. When the grid in the ion source was biased at −200 V, the ion signal dropped to 54% of its peak value at a retardation voltage of 1500 V. Assuming a group velocity of 390 m/s for each droplet, each helium atom in the droplet had a kinetic energy of 3.18 meV, and to obtain a total kinetic energy of 1500 V, the corresponding size of the doped droplet was $4.4 \times 10^5$ helium/droplet. Thus it was concluded that about 54% of the doped droplets were larger than $4.4 \times 10^5$ helium/droplet.

The average size of doped droplets from this retardation experiment was about one tenth of that from the deflector experiment (FIG. 30). One factor for this discrepancy could be the position of the detector: in this experiment, the detector was placed 68 cm further downstream from the ion source. Continued evaporation due to collisions with ambient molecules in the flight path would result in a decreased droplet size. At a vacuum level of $4 \times 10^{-6}$ torr and a source temperature of 14 K, the average radius of a droplet was about 17 nm, and the average collision rate was $3 \times 10^5$/s. If each collision consumed about 42 helium atoms by evaporation, the total loss of helium atoms after a path length of 68 cm was $2.2 \times 10^4$. This value was too small to account for the one order of magnitude decrease in droplet size from this energy filter experiment. Similarly, radiative heating in the high vacuum chamber should also be limited. Another possibility was the additional collisions between the small doped droplets stopped in the path of the larger droplets at the retardation electrode (the fine mesh). Since this effect was size dependent, particularly detrimental to large sized droplets, it could play a significant role in reducing the average size of the droplet beam from this retardation experiment.

Example 8

Relative Doping Efficiency

To determine the absolute doping efficiency, the ratio of the total number of doped droplets and the total number of ions in the doping region has to be determined. The absolute number of doped droplets is affected by the temperature of the droplet source and by the grid voltage of the ion source. Without a bias voltage on the grid of the ion source, only thermal ions were present around the region of the filament, and no doping was observable when the source temperature of the droplet beam was above 14 K. As the bias on the grid increased, more ions were pulled into the region of the droplet for doping, and more doped ions were observable. However, the number of ions in the doping region was limited by the space charge effect while the measured current on the grid was not.

To avoid the above difficulties, a relative doping efficiency was defined by setting the ratio of doped ions to the ions on the grid to unity at a kinetic energy (grid voltage) of −20 V and a source temperature of 14 K. This choice of the kinetic energy corresponded to the lowest bias when doped ions were observable at all source temperatures between 14 K and 17 K. The left side of FIG. 33 shows the relative doping efficiency at different kinetic energies and different source temperatures. At a fixed source temperature, the size distribution of the droplet beam was fixed. With the increase in grid voltage, the absolute number of doped ions increased, but the relative doping efficiency actually decreased. With the increase in source temperature, the droplet distribution shifted to smaller sizes, and the relative doping efficiency also decreased. However, if the maximum of each trace was renormalized, as shown on the right side of FIG. 33, all traces overlap. This result implied that lowering the source temperature uniformly increased the doping efficiency, with no effect on the final size distribution of the doped droplets.

The decrease in doping efficiency with increasing grid voltage shown in FIG. 33 demonstrated the adverse effect of kinetic energy of the bare ions for doping. However, the situation was complicated by the fact that bare ions could oscillate in and out of the grid during the doping process. In FIG. 27, the grid of the ion source attracted the emitted $Cs^+$ ions into the field free central region where the droplet beam traversed. Without collision with a droplet, a cation could pass through the grid and move towards the chamber wall before turning back. This oscillatory motion under different grid voltages was simulated using Lorentz-EM. Within the duration of the droplet beam (200 μs), the number of round trips of a $Cs^+$ ion passing through the centre of the grid was 15, a value essentially independent of the grid voltage. Also, higher energy ions were more prone to be affected by fringe fields, possibly because of their deeper penetration into the outside region of the grid. Even though they had a higher frequency of oscillation, their stable oscillatory periods were limited. It was therefore concluded that the rapid decrease in the relative doping efficiency with grid voltage on the left of FIG. 33 was indeed the adverse effect of kinetic energy.

The physical origin of the decreasing doping efficiency with increasing kinetic energy was puzzling. If it was assumed the "bend" in FIG. 29 at a bias of −150 V was truly related to the space charge effect, the drop in the doping efficiency beyond −150 V could be ignored, because the number of available ions for doping remained more or less constant instead of increasing as shown in FIG. 29. However, a clear drop between −20 V and −150 V was still evident. When the kinetic energy varied from 20 eV to 100 eV, the velocity of the cesium ions varied from 5000 m/s to 10000 m/s, and the doping efficiency dropped by 60%.

The decrease in the relative doping efficiency from 14 K to 17 K was explained from the numerical analysis. The binding energy of each helium atom was about 5 cm$^{-1}$ in a droplet. To cool down a single Cs$^+$ ion, with a kinetic energy of 400 eV, would take more than 10$^6$ helium atoms with a minimum droplet radius of 20 nm. To further escape the potential well of the grid at −400 V, the cooled ion had to retain another 10$^6$ helium atoms (see Example 5). The total number of droplets in this size range from a pure droplet beam was obtained by integrating Eq. 1 in the appropriate size range. Assuming the same gas flux, the theoretical number of droplets at 17 K was about 1.8 times of that at 14 K. This meant that if all droplets larger than 10$^6$ had the same probability of doping, there should be 1.8 times more ions at 17 K than at 14 K. On the other hand, if the lower limit of integration was changed from 10$^6$ to 10$^7$, the calculation revealed that the total number of droplets for pickup at 17 K was only ¼ of that at 14 K. This value was in agreement with the experimental observation where the number of doped ions at 17 K was about ⅓ of that at 14 K. Therefore, the lower relative doping efficiency at higher nozzle temperatures was most likely due to the lack of viable sized droplets.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for determining molecular structure, comprising:
    producing substantially solvent-free sample ions from a sample;
    cooling the sample ions;
    introducing the cooled sample ions into a diffraction zone;
    orienting a first cooled sample ion to produce a first oriented sample ion in the diffraction zone;
    collecting a diffraction image from the first oriented sample ion;
    orienting a second cooled sample ion in the diffraction zone;
    collecting a second image from the second cooled sample ion; and
    determining molecular structure using collected sample ion images.

2. The method according to claim 1, further comprising using at least a third cooled sample ion.

3. The method according to claim 1, wherein cooling the sample ions comprises cooling with a cooled ion trap, a superfluid, or a combination thereof.

4. The method according to claim 1, wherein the sample comprises macromolecules, nano-crystals of macromolecules, fragments of macromolecules, clusters of macromolecules, complexes of macromolecules, nanostructures of organic compounds, nanostructures of inorganic compounds, or combinations thereof.

5. The method according to claim 4, wherein the macromolecules are proteins, nucleic acids, carbohydrates or lipids.

6. The method according to claim 1, wherein producing sample ions comprises using electrospray ionization, matrix assisted laser desorption ionization, a mass spectrometer, or a combination thereof.

7. The method according to claim 4, further comprising purifying macromolecules according to mass prior to cooling, purifying macromolecules according to conformation prior to cooling, or purifying macromolecules according to mass and conformation prior to cooling.

8. The method according to claim 3, wherein the sample ions are cooled to a temperature of greater than absolute zero to less than about 50 K.

9. The method according to claim 1, wherein the diffraction image is produced by x-ray diffraction or an electron beam.

10. The method according to claim 1, wherein the sample ions are oriented using a direct current electric field and a laser.

11. The method according to claim 1, further comprising orienting plural sample ions within about 1° for a period of from 5 ns to 50 μs.

12. The method according to claim 10, further comprising changing elliptical polarization of the laser to simultaneously rotate the sample ions to obtain diffraction from multiple orientations.

13. The method according to claim 5, further comprising:
    orienting packets of sample ions comprising from about 10$^2$ to about 10$^4$ macromolecules for a selected period of time; and
    collecting diffraction images from these packets in a pulsed mode or continuous mode.

14. The method according to claim 4, further comprising cooling the macromolecules or macromolecular ions in superfluidic helium and constraining the macromolecules or macromolecular ions embedded in the superfluidic helium in about a 0.1 mm$^3$ region in crossing paths of an alignment laser beam and an electron beam.

15. The method according to claim 10, further comprising:
    (i) using a rotating polarization prism to rotate sample ions stepwise around a primary axis of polarizability;
    (ii) periodically changing elliptical polarization of an alignment laser, or a combination thereof;
    (iii) minimizing radiation damage to sample ions by replacing sample ions every laser pulse and cooling the sample ions to a temperature greater than 0 K to about 50 K;
    (iv) a combination thereof.

16. The method according to claim 1, further comprising accumulating data from multiple packets of sample ions oriented substantially identically.

17. The method according to claim 1, further comprising producing a diffraction image that is a simple sum of continuous images of electron scattering from each ion in the diffraction zone.

18. The method according to claim 15, further comprising:
    collecting diffraction data from a first packet of sample ions at a first orientation;
    changing laser polarization to orient a second packet of sample ions by a predictable amount to a second orientation; and
    collecting diffraction data from the second packet of sample ions.

19. An apparatus for determining molecular structure, comprising:
 a source of sample ions;
 an ion chiller;
 an orientation laser for orienting cooled ions in a diffraction zone; and
 an imaging system to produce diffraction images of oriented sample ions in the diffraction zone.

20. The apparatus according to claim 19, wherein the imaging system comprises an x-ray diffraction system, an electron diffraction system, or both.

21. The apparatus according to claim 19, wherein the ion chiller comprises a source of superfluidic helium droplets or a cooled ion trap.

22. The apparatus according to claim 19, wherein the apparatus further comprises electrodes upstream of the orientation laser to produce a direct current field for preliminary orientation of ions, a mass analyzer, an orientation and diffraction chamber, an analytical section downstream of the diffraction zone, an electron gun, an ion trap, an alignment laser that generates polarized infrared light, or a combination thereof.

23. The apparatus according to claim 19, wherein the source of sample ions comprises an electrospray ionization source, a mass spectrometer, a sample purifying section, or a combination thereof.

24. The apparatus according to claim 23, wherein the apparatus comprises the sample purifying section, and the sample purifying section comprises a mass analyzer, an ion drift tube, deflector electrodes, an ion bender, an ion trap, a helium sample ion trap, or a combination thereof.

25. The apparatus according to claim 22, where the orientation and diffraction chamber is coupled in series to a helium ion trap.

26. The apparatus according to claim 22, wherein the analytical section includes an ion bender and mass detector, a helium droplet detector, a time-of-flight component upstream of a fast ion gauge, a multichannel plate detector, or a combination thereof.

27. The apparatus according to claim 19, wherein the diffraction zone comprises a pulsed electron beam, a pulsed laser beam, and a pulsed ion beam; the orientation laser further comprises a polarizer and at least one phase retarder; or both.

28. The apparatus according to claim 21, further comprising:
 (i) a pulsed helium droplet valve having an opening time of about 10-20 microseconds, capable of withstanding pressures up to about 100 atmospheres, and operating at frequencies of several thousand Hertz, or a continuous cooled nozzle;
 (ii) an analytical wheel comprising plural receptacles for housing at least one device selected from a Faraday cup to determine the number of electrons included in an electron beam, a phosphor screen to detect electrons to time an electron beam and its intersection with doped helium droplets and the orientation laser, a standard transmission electron microscopy (TEM) sample for calibration, or a time-of-flight mass spectrometer;
 (iii) a cold head coupled to the helium droplet source to pre-cool high pressure helium gas in the droplet source to a desired temperature of from greater than 0 K to about 20 K;
 (iv) a series of electrodes upstream of the diffraction zone to separate pure helium droplets, bare ions and helium droplets doped with sample ions before each proceeds into the diffraction zone;
 (v) a cryogenic helium nozzle cooled to 0 to 20 K that allows adjusting temperature of the helium nozzle to determine helium droplet size distribution; or
 (vi) a combination thereof.

29. The apparatus according to claim 19, further comprising:
 a cooled ion trap or a source of superfluidic helium droplets;
 two or more electrodes to produce a direct current electric field for preliminary orientation of the sample ions upstream of the orientation laser;
 an electron source for electron diffraction imaging; and
 a recorder to record the images.

30. A device for determining size and overlap of plural beams, comprising:
 a linear variable differential transformer (LVDT);
 a motorized linear displacement actuator;
 a shuttle comprising a cutting edge; and
 an intensity detector for each of the plural beams.

* * * * *

UNITED STATES PATENT AND TRADEMARK OFFICE
CERTIFICATE OF CORRECTION

Page 1 of 1

PATENT NO. : 9,279,778 B2
APPLICATION NO. : 14/610980
DATED : March 8, 2016
INVENTOR(S) : Joseph Beckman et al.

It is certified that error appears in the above-identified patent and that said Letters Patent is hereby corrected as shown below:

In the Specification:

The paragraph at column 1, line 17,

"This invention was made with government support the National Institutes of Health, under Grant No. RC1 GM092054. The government has certain rights in the invention."

should read

--This invention was made with government support under Grant No. CHE-0827182 awarded by National Science Foundation and Grant No. GM-092054 awarded by National Institutes of Health. The government has certain rights in the invention.--

Signed and Sealed this
Third Day of May, 2016

Michelle K. Lee
*Director of the United States Patent and Trademark Office*